United States Patent
Pernia et al.

(10) Patent No.: US 12,223,643 B2
(45) Date of Patent: Feb. 11, 2025

(54) MACHINE-LEARNING SYSTEM FOR DIAGNOSING DISORDERS AND DISEASES AND DETERMINING DRUG RESPONSIVENESS

(71) Applicant: Sanford Burnham Prebys Medical Discovery Institute, La Jolla, CA (US)

(72) Inventors: Cameron Pernia, Cambridge, MA (US); Heather Tolcher, Houston, TX (US); Evan Y. Snyder, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 502 days.

(21) Appl. No.: 17/616,461

(22) PCT Filed: May 29, 2020

(86) PCT No.: PCT/US2020/035331
§ 371 (c)(1),
(2) Date: Dec. 3, 2021

(87) PCT Pub. No.: WO2020/247273
PCT Pub. Date: Dec. 10, 2020

(65) Prior Publication Data
US 2022/0237786 A1  Jul. 28, 2022

Related U.S. Application Data

(60) Provisional application No. 62/856,631, filed on Jun. 3, 2019.

(51) Int. Cl.
*G06T 7/00* (2017.01)
*G06N 20/20* (2019.01)
(Continued)

(52) U.S. Cl.
CPC .......... *G06T 7/0012* (2013.01); *G06N 20/20* (2019.01); *G06V 10/774* (2022.01);
(Continued)

(58) Field of Classification Search
CPC ......... G06T 7/0012; G06T 2207/20081; G06T 2207/30024; G06N 20/20; G06N 20/00;
(Continued)

(56) References Cited

U.S. PATENT DOCUMENTS

2013/0132311 A1  5/2013  Liu et al.
2015/0104528 A1*  4/2015  Fisher .................... A61K 33/14
424/722
(Continued)

FOREIGN PATENT DOCUMENTS

EP          2878602 A1      6/2015
WO    WO-2016036565 A1    3/2016
(Continued)

OTHER PUBLICATIONS

Lee, Han-Kyu et al. "Three Dimensional Human Neuro-Spheroid Model of Alzheimer's Disease Based on Differentiated Induced Pluripotent Stem Cells." PloS one vol. 11,9 e0163072. Sep. 29, 2016, doi: 10.1371/journal.pone.0163072 (Year: 2016).*
(Continued)

*Primary Examiner* — Matthew C Bella
*Assistant Examiner* — Janice E. Vaz
(74) *Attorney, Agent, or Firm* — WILSON SONSINI GOODRICH & ROSATI

(57) ABSTRACT

Described are platforms, systems, and methods for screening patients. In one aspect, a computer-implemented method comprises: receiving, from a cellular imaging device, image data comprising calcium kinetic features of neuronal cultures derived from a patient; processing the image data through a machine-learning model to determine a diagnosis
(Continued)

for the patient based on the calcium kinetic features, the machine-learning model trained using neuronal calcium data; and providing the diagnosis a user interface.

15 Claims, 45 Drawing Sheets

(51) Int. Cl.
    *G06V 10/774*     (2022.01)
    *G06V 10/776*     (2022.01)
    *G06V 20/69*     (2022.01)
    *G16C 20/70*     (2019.01)
    *G16H 70/40*     (2018.01)

(52) U.S. Cl.
    CPC .......... *G06V 10/776* (2022.01); *G06V 20/693* (2022.01); *G06V 20/698* (2022.01); *G16C 20/70* (2019.02); *G16H 70/40* (2018.01); *G06T 2207/20081* (2013.01); *G06T 2207/30024* (2013.01)

(58) Field of Classification Search
    CPC .. G06V 10/774; G06V 10/776; G06V 20/693; G06V 20/698; G16C 20/70; G16H 70/40; G16H 50/20; G16H 50/70; G01N 2800/304; G01N 33/5058; A61P 25/00
    See application file for complete search history.

(56) References Cited

U.S. PATENT DOCUMENTS

| | | | |
|---|---|---|---|
| 2015/0301030 A1* | 10/2015 | Eggan | G01N 33/5023 435/29 |
| 2016/0040230 A1 | 2/2016 | Akeson et al. | |
| 2018/0268942 A1* | 9/2018 | Kamali-Zare | G06T 17/10 |
| 2020/0165680 A1* | 5/2020 | Bahado-Singh | G16B 20/20 |

FOREIGN PATENT DOCUMENTS

| | | |
|---|---|---|
| WO | WO-2018106713 A1 | 6/2018 |
| WO | WO-2020247273 A1 | 12/2020 |

OTHER PUBLICATIONS

Rita, R. Romito-DiGiacomo et al. "Effects of Alzheimer's Disease on Different Cortical Layers: They Role of Intrinsic Differences in AB Susceptibility." Journal of Neuroscience Aug. 8, 2007, 27 (32) 8496-8504; DOI: https://doi.org/10.1523/JNEUROSCI.1008-07.2007 (Year: 2007).*
Tobe et al., Probing the lithium-response pathway in hiPSCs implicates the phosphoregulatory set-point for a cytoskeletal modulator in bipolar pathogenesis. PNAS 114(22):E4462-E4471 (2017). (Year: 2017).*
McDonough et al., Assay of calcium transients and synapses in rat hippocampal neurons by kinetic image cytometry and high-content analysis: an in vitro model system for postchemotherapy cognitive impairment. Assay and Drug Development Technologies 15(5):220-236 (2017). (Year: 2017).*
Eugene AR, Masiak J, Eugene B. Predicting lithium treatment response in bipolar patients using gender-specific gene expression biomarkers and machine learning. F1000Res. Apr. 18, 2018;7:474. doi: 10.12688/f1000research.14451.3. (Year: 2018).*
McDonough et al., Assay of calcium transients and synapses in rat hippocampal neurons by kinetic image cytometry and high-content analysis: an in vitro model system for postchemotherapy cognitive impairment. Assay and Drug Development Technologies 15(5):220-236 (2017).
PCT/US2020/035331 International Search Report and Written Opinion dated Aug. 10, 2020.
Tobe et al., Probing the lithium-response pathway in hiPSCs implicates the phosphoregulatory set-point for a cytoskeletal modulator in bipolar pathogenesis. PNAS 114(22):E4462-E4471 (2017).
Uchida et al. Semaphorin3A signalling is mediated via sequential Cdk5 and GSK3beta phosphorylation of CRMP2: implication of common phosphorylating mechanism underlying axon guidance and Alzheimer's disease. Genes Cells 10:165-179 (2005).
Yamashita et al. Regulation of spine development by semaphorin3A through cyclin-dependent kinase 5 phosphorylation of collapsin response mediator protein 1. J Neurosci 27:12546-12554 (2007).

* cited by examiner

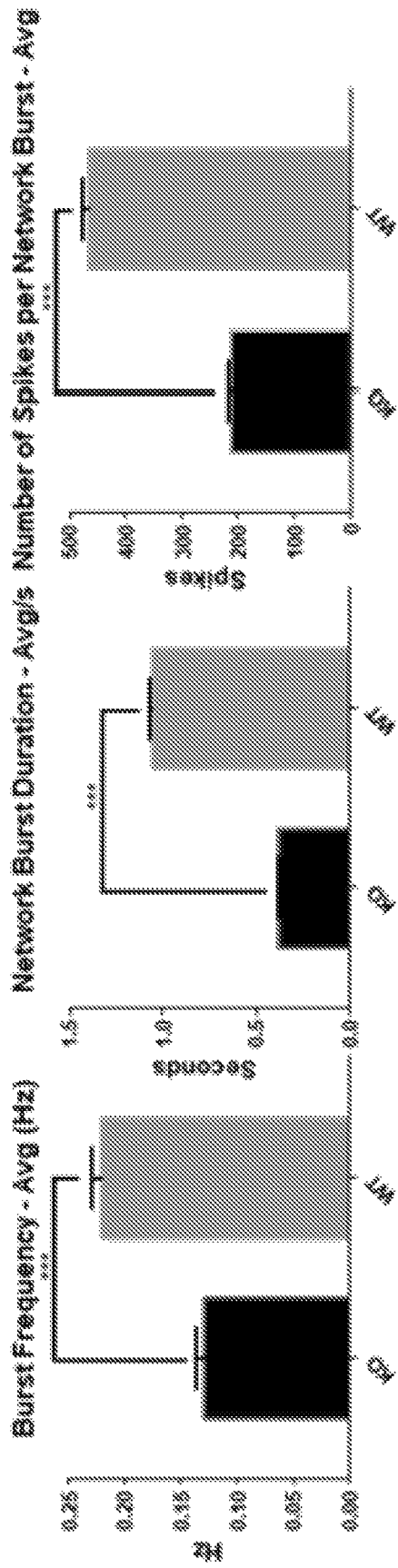

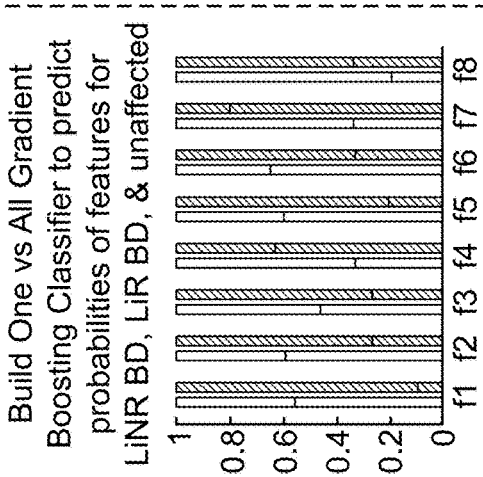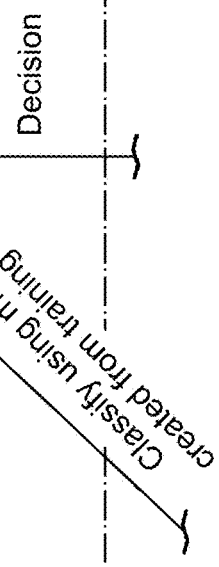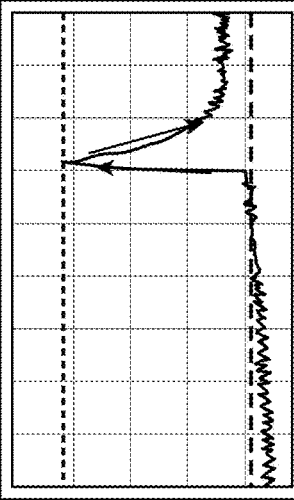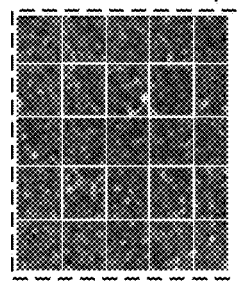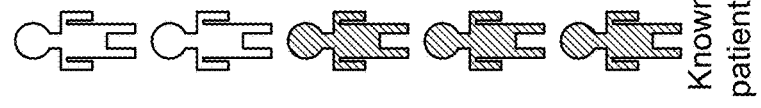
FIG. 8D $$T_c^* = \{t : \bar{x}_t(c) \in ((\bar{x}_t(c) > \bar{x}_{t\pm 2}(c)) \cap (\bar{x}_t(c) > \alpha_c))\}$$

$$P = \{\bar{x}_t : \bar{x}_t > \bar{x}_{t-2} \text{ and } \bar{x}_t > \bar{x}_{t+2}\}, \text{ with } \alpha = \max_{\bar{x}_t \in P}$$

$$\beta_\tau = \begin{cases} 0 & \varnothing = \{\bar{x}_t : t \in \tau\} \cap P_* \\ 1 & \text{otherwise} \end{cases} \qquad \beta_\tau = \sum_{\bar{x}_t \in P_*}$$

$$S_\tau(c) = \begin{cases} 0 & T_c^* \cap \tau = \varnothing \\ 1 & \text{otherwise} \end{cases} \qquad S_\tau = \sum_{\substack{\beta_\tau(c) \geq 1 \\ c \in C}}$$

$T_c^*$ = set of time stamps during which a cell has a strong peak  $P$ = Set of counted peaks
$\alpha_c$ = threshold for counting a peak  $\beta_\tau$ = Synchrony counting threshold
$S_\tau$ = Synchrony score

FIG. 9A

MACHINE-LEARNING SYSTEM FOR DIAGNOSING DISORDERS AND DISEASES AND DETERMINING DRUG RESPONSIVENESS

CROSS-REFERENCE TO RELATED APPLICATIONS

This application is the U.S. National Stage application of International Application No. PCT/US2020/035331, filed May 29, 2020, and claims the benefit of U.S. Provisional Patent Application No. 62/856,631 filed on Jun. 3, 2019. Priority is claimed pursuant to 35 U.S.C. § 119. The above noted patent application is incorporated by reference as if set forth fully herein.

BACKGROUND

The subject matter of machine learning includes the study of computer modeling of learning processes in their multiple manifestations. In general, learning processes include various aspects such as the acquisition of new declarative knowledge, the devilment of motor and cognitive skills through instruction or practice, the organization of new knowledge into general, effective representations, and the discovery of new facts and theories through observation and experimentations. Implanting such capabilities in computers has been a goal of computer scientist since the inception of the computer era. However, solving this problem has been, and remains, a most challenging goal in artificial intelligence (AI). Unlike human based decision, decision assistance systems embedded with machine learning algorithms are corruption free as thus are reliable. Achieving an understanding of historical data, the identification of trends, seasonal patterns, anomalies, emerging patterns, is time-consuming and prone to errors. Machine learning algorithms efficiently learn rules thus enabling the identification of these signals and provide accurate predictions on future outcomes.

SUMMARY

The most common, lethal, and societally impactful mental illness is bipolar disorder (BPD). BPD is a neuropsychiatric disease affecting 2.6 percent of the adult population. BPD is a chronic illness, characterized by oscillatory episodes of mania and depression, and is historically viewed as a mood disorder along with major depressive disorder. Although BPD has an approximately 80 percent heritability rate and genome-wide association studies (GWAS) have connected several chromosomal regions with BPD researchers have been unable to find a single gene anomaly that manifests the disease. The current understanding in the field is that BD is likely a complex polygenic disorder that manifests as a confluence of genetic mutations.

Alzheimer's disease is a progressive disorder that causes brain cells to waste away (degenerate) and die. Alzheimer's disease is the most common cause of dementia—a continuous decline in thinking, behavioral and social skills that disrupts a person's ability to function independently.

Parkinson's disease is a progressive nervous system disorder that affects movement. Symptoms start gradually, sometimes starting with a barely noticeable tremor in just one hand. Tremors are common, but the disorder also commonly causes stiffness or slowing of movement.

BPD is the most fatal psychiatric disease due to a high suicide rate, and little is known regarding its underlying pathology. The National Institute of Mental Health (NIHM) has found 69 percent of BPD patients are misdiagnosed initially and more than one-third remained misdiagnosed for 10 years or more. Moreover, according to the NIHM, BPD patients can go through years of drugs trials before finding efficacious treatment options, which has a high financial and quality of life cost. Moreover, according to the World Health Organization (WHO), BPD is the 6th most impactful disease worldwide for reducing economic productivity.

Currently there is no reliably safe or predictably efficacious therapy for treating BPD. However, through a combinatorial approach, taking advantage of human induced pluripotent stem cells (hiPSCs)-derived neurons, animal models and human tissues, development of the described classification system has demonstrated that the "lithium-response pathway" in BPD governs the phosphorylation and activation of collapsin response mediator protein 2 (CRMP2), a key cytoskeleton regulator, particularly for dendrites and dendritic spines. Moreover, development of the described classification system has shown that neuronal CRMP2 activity reduction causes hyperactive neuronal signaling that creates hypofunctional neuronal networks, which are tractable to characteristic patterns predictive of the disease. The described classification system may also be employed to diagnose diseases such as Alzheimer's disease and Parkinson's disease.

The "inactive:active" setpoint for CRMP2 is higher in BPD. Lithium treatment normalizes active CRMP2 levels together with spine morphology and function. Comparing transgenic mice with endogenous, absent, and constitutively active CRMP2, has shown that CRMP2 activity impacts neuronal signaling kinetics and protein regulation. Specifically, BD-like transgenic CRMP2 neurons have hyperactive calcium activity, while having hypofunctional neuronal-network signaling, implying BPD is a disorder more of "neurodevelopment" than "mood," as was previously categorized in the DSM-IV. Furthermore, a machine learning classifier trained on neuronal calcium data, as employed by the described classification system, can successfully diagnose if an individual has BPD, and can determine if the individual will respond clinically to lithium. Collectively, this work illuminates long sought-after findings in BPD pathology, insights into brain function at large, novel targets for future neuropsychiatric therapeutics, and the first ever in vitro diagnostic BPD assay.

Currently there is no therapeutic for BPD for which efficacy or safety is predictable. Lithium carbonate remains the gold standard for stabilizing BPD mania and has been shown to reduce the risk of suicide, albeit only approximately 35 percent of patients respond to lithium treatment (Li-R BPD). The distinction is so stark, that BD patients are classified as either lithium responsive or lithium non-responsive (Li-NR BPD), suggesting Li-NR and Li-R BPD are pathogenically distinct phenocopies. For decades, the precise mechanism of action of lithium for BPD has been elusive despite a large body of work supporting a diversity of plausible hypotheses and directions.

Development of the described classification system has shown that that lithium acts upon CRMP2 when regulating BPD behavior. The canonical roles of CRMP2 have been primarily understood as regulating neurite growth and axonal transport. Research has found many CRMP2 binding partners are associated with neurite organization including actin, tubulin, dynein, and kinesin-1. CRMP2 activity is predominantly regulated by post-translational modification via kinases and phosphatases, inactive when phosphorylated at Threonine-514 (CRMP2-pT514). For CRMP2's importance in normal CNS development and function, there is not much epidemiological evidence connecting the gene to behavior modifying diseases.

The described classification system can accurate diagnose BPD clinically and can be used to predict best drug treatments. The described classification system may also be employed as a functional screening platform for identifying novel BPD therapeutics.

In one aspect, disclosed herein are classification systems comprising a user interface; a cellular imaging device; one or more processors; and a computer-readable storage device coupled to the one or more processors and having instructions stored thereon which, when executed by the one or more processors, cause the one or more processors to perform operations comprising: receiving, from the cellular imaging device, image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to the user interface. In some embodiments, the operations comprise: processing the image data through the machine-learning model to determine if the patient will respond to a treatment for BPD. In some embodiments, the treatment comprises Lithium carbonate for BPD. In some embodiments, the operations comprise: processing the image data through the machine-learning model to determine a drug responsiveness of patient. In some embodiments, the diagnosis comprises whether the patient is lithium responsive or lithium non-responsive. In some embodiments, the machine-learning model comprises at least one of a linear regression, a naive bayes, a random forest, a one versus all, support vector classifier module, or a k-nearest neighbor (KNN) algorithm. In some embodiments, the machine-learning model comprises a gradient boosting classifier to prevent over fitting and not to over bias the machine-learning model. In some embodiments, the neuronal calcium data is acquired from in vitro neural cultures. In some embodiments, the in vitro neural cultures are derived from hiPSC isolated from BPD individuals and unaffected healthy human controls. In some embodiments, the neuronal calcium data comprises calcium kinetic features. In some embodiments, the calcium kinetic features comprise basal calcium level, peak calcium transience, and calcium event frequency. In some embodiments, the calcium kinetic features comprise at least one of calcium event influx, calcium event efflux, or calcium event amplitude. In some embodiments, down sampling is employed during training of the machine-learning model. In some embodiments, the neuronal calcium data comprises data points, and wherein training the machine-learning model includes separating the data points by cell line and disease type. In some embodiments, a portion of the neuronal calcium data is employed to train the machine-learning model and a remaining portion of the neuronal calcium data is employed to test the machine-learning model once trained. In some embodiments, testing the trained machine-learning comprises pulling lithium chloride (LiCl) treated and untreated data points from the remaining portion of the neuronal calcium data. In some embodiments, the portion of the neuronal calcium data comprises 70 percent of the data for training, and wherein the remaining portion of the neuronal calcium data comprises 30 percent of the data for validation. In some embodiments, the portion of the neuronal calcium data comprises 80 percent of the data for training, and wherein the remaining portion of the neuronal calcium data comprises 20 percent of the data for validation.

In some embodiments, the cellular imaging device comprises an IC200 Kinetic Image Cytometer, and wherein the image data is generated through calcium imaging performed with the IC200 Kinetic Image Cytometer and a calcium sensitive dye Fluo-4 AM. In some embodiments, the image data comprises intracellular calcium level traces. In some embodiments, the neuronal cultures comprise CRMP2-knock out (KO), CRMP2-knock in (KI), and WT E16.5 primary hippocampal neurons. In some embodiments, the neuronal cultures are derived from blood samples from the patient. In some embodiments, the diagnosis is for BPD. In some embodiments, the diagnosis is for Alzheimer's disease or Parkinson's disease.

In another aspect, disclosed herein are non-transitory computer-readable storage media coupled to one or more processors and having instructions stored thereon which, when executed by the one or more processors, cause the one or more processors to perform operations comprising: receiving image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to a user interface. In some embodiments, the operations comprise: processing the image data through the machine-learning model to determine if the patient will respond to a treatment for BPD. In some embodiments, the treatment comprises Lithium carbonate for BPD. In some embodiments, the operations comprise: processing the image data through the machine-learning model to determine a drug responsiveness of patient. In some embodiments, the diagnosis comprises whether the patient is lithium responsive or lithium non-responsive. In some embodiments, the machine-learning model comprises at least one of a linear regression, a naive bayes, a random forest, a one versus all, support vector classifier module, or a KNN algorithm. In some embodiments, the machine-learning model comprises a gradient boosting classifier to prevent over fitting and not to over bias the machine-learning model. In some embodiments, the neuronal calcium data is acquired from in vitro neural cultures. In some embodiments, the in vitro neural cultures are derived from hiPSC isolated from BPD individuals and unaffected healthy human controls. In some embodiments, the neuronal calcium data comprises calcium kinetic features. In some embodiments, the calcium kinetic features comprise basal calcium level, peak calcium transience, and calcium event frequency. In some embodiments, the calcium kinetic features comprise at least one of calcium event influx, calcium event efflux, or calcium event amplitude. In some embodiments, down sampling is employed during training of the machine-learning model. In some embodiments, the neuronal calcium data comprises data points, and wherein training the machine-learning model includes separating the data points by cell line and disease type. In some embodiments, a portion of the neuronal calcium data is employed to train the machine-learning model and a remaining portion of the neuronal calcium data is employed to test the machine-learning model once trained. In some embodiments, testing the trained machine-learning comprises pulling LiCl treated and untreated data points from the remaining portion of the neuronal calcium data. In some embodiments, the portion of the neuronal calcium data comprises 70 percent of the data for training, and wherein the remaining portion of the neuronal calcium data comprises 30 percent of the data for validation. In some embodiments, the portion of the neuronal calcium data comprises 80 percent of the data for training, and wherein the remaining portion of the neuronal calcium data comprises 20 percent of the data for validation. In some embodiments, the image data is generated through calcium imaging performed with an IC200 Kinetic Image Cytometer and a calcium sensitive dye Fluo-4 AM. In some embodiments, the image data comprises intracellular calcium level traces. In some embodiments, the neuronal cultures comprise CRMP2-KO, CRMP2-KI, and WT E16.5 primary hippocampal neurons. In some embodiments, the neuronal cultures are derived from blood samples from the patient. In some embodiments, the diagnosis is for BPD. In some embodiments, the diagnosis is for Alzheimer's disease or Parkinson's disease.

In another aspect, disclosed herein are computer-implemented methods for patient screening comprising: receiving, from a cellular imaging device, image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to a user interface. In some embodiments, the method comprises: processing the image data through the machine-learning model to determine if the patient will respond to a treatment for BPD. In some embodiments, the treatment comprises Lithium carbonate for BPD. In some embodiments, the method comprises: processing the image data through the machine-learning model to determine a drug responsiveness of patient. In some embodiments, the diagnosis comprises whether the patient is lithium responsive or lithium non-responsive. In some embodiments, the machine-learning model comprises at least one of a linear regression, a naive bayes, a random forest, a one versus all, support vector classifier module, or a KNN algorithm. In some embodiments, the machine-learning model comprises a gradient boosting classifier to prevent over fitting and not to over bias the machine-learning model. In some embodiments, the neuronal calcium data is acquired from in vitro neural cultures. In some embodiments, the in vitro neural cultures are derived from hiPSC isolated from BPD individuals and unaffected healthy human controls. In some embodiments, the neuronal calcium data comprises calcium kinetic features. In some embodiments, the calcium kinetic features comprise basal calcium level, peak calcium transience, and calcium event frequency. In some embodiments, the calcium kinetic features comprise at least one of calcium event influx, calcium event efflux, or calcium event amplitude. In some embodiments, down sampling is employed during training of the machine-learning model. In some embodiments, the neuronal calcium data comprises data points, and wherein training the machine-learning model includes separating the data points by cell line and disease type. In some embodiments, a portion of the neuronal calcium data is employed to train the machine-learning model and a remaining portion of the neuronal calcium data is employed to test the machine-learning model once trained. In some embodiments, testing the trained machine-learning comprises pulling LiCl treated and untreated data points from the remaining portion of the neuronal calcium data. In some embodiments, the portion of the neuronal calcium data comprises 70 percent of the data for training, and wherein the remaining portion of the neuronal calcium data comprises 30 percent of the data for validation. In some embodiments, the portion of the neuronal calcium data comprises 80 percent of the data for training, and wherein the remaining portion of the neuronal calcium data comprises 20 percent of the data for validation. In some embodiments, the cellular imaging device comprises an IC200 Kinetic Image Cytometer, and wherein the image data is generated through calcium imaging performed with the IC200 Kinetic Image Cytometer and a calcium sensitive dye Fluo-4 AM. In some embodiments, the image data comprises intracellular calcium level traces. In some embodiments, the neuronal cultures comprise CRMP2-KO, CRMP2-KI, and WT E16.5 primary hippocampal neurons. In some embodiments, the neuronal cultures are derived from blood samples from the patient. In some embodiments, the diagnosis is for BPD. In some embodiments, the diagnosis is for Alzheimer's disease or Parkinson's disease.

In some embodiments, the described classification systems can successfully diagnose if an individual has bipolar disorder (BPD), and can determine if the individual will respond clinically to a bipolar disorder (BPD) treatment. In some embodiments, the BPD treatment is selected from the group consisting of mood stabilizers, antipsychotics, antidepressants, antidepressant-antipsychotics, anti-anxiety medications, and combinations thereof. In some embodiments, the described classification systems can successfully diagnose if an individual has bipolar disorder (BPD), and can determine if the individual will respond clinically to a mood stabilizer. In some embodiments, the mood stabilizer is selected from the group consisting of lithium (e.g., Lithobid), valproic acid (e.g., Depakene), divalproex sodium (e.g., Depakote), carbamazepine (e.g., Tegretol, Equetro, and Carbatrol), lamotrigine (e.g., Lamictal), and combinations thereof. In some embodiments, the described classification systems can successfully diagnose if an individual has bipolar disorder (BPD), and can determine if the individual will respond clinically to an antipsychotic medication. In some embodiments, the antipsychotic medication is selected from the group consisting of olanzapine (e.g., Zyprexa), risperidone (e.g., Risperdal), quetiapine (e.g., Seroquel), aripiprazole (e.g., Abilify), ziprasidone (e.g., Geodon), lurasidone (e.g., Latuda), asenapine (e.g., Saphris), and combinations thereof. In some embodiments, the described classification systems can successfully diagnose if an individual has bipolar disorder (BPD), and can determine if the individual will respond clinically to an antidepressant medication. In some embodiments, the antidepressant medication is selected from the group consisting of citalopram (e.g., Celexa), escitalopram (e.g., Lexapro), fluoxetine (e.g., Prozac, Sarafem, Selfemra, and Prozac Weekly), fluvoxamine (e.g., Luvox), paroxetine (e.g., Paxil, Paxil CR, and Pexeva), sertraline (e.g., Zoloft), vortioxetine (e.g., Trintellix and Brintellix), vilazodone (e.g., Viibryd). In some embodiments, the described classification systems can successfully diagnose if an individual has bipolar disorder (BPD), and can determine if the individual will respond clinically to an antidepressant-antipsychotic medication. In some embodiments, the antidepressant-antipsychotic medication is selected from the group consisting of olanzapine/fluoxetine (e.g., Symbyax), amitriptyline/perphenazine (e.g., Duo-Vil, Etrafon, Triavil, or Triptafen), aripiprazole/sertraline (e.g., ASC-01), flupentixol/melitracen (e.g., Deanxit, Placida, Franxit, Anxidreg, and Danxipress), tranylcypromine/trifluoperazine (e.g., Parstelin, Parmodalin, Jatrosom N, and Stelapar), and combinations thereof. In some embodiments, the described classification systems can successfully diagnose if an individual has bipolar disorder (BPD), and can determine if the individual will respond clinically to an anti-anxiety medication. In some embodiments, the anti-anxiety medication is selected from the group consisting of benzodiazepines (e.g., diazepam, alprazolam, clonazepam, and lorazepam), beta-blockers (e.g., Acebutolol (Sectral), Atenolol (Tenormin), Betaxolol (Kerlone), Bisoprolol (Zebeta, Ziac), Carteolol (Cartrol), Carvedilol (Coreg), Labetalol (Normodyne, Trandate), Metoprolol (Lopressor, Toprol-XL), Nadolol (Corgard), Nebivolol (Bystolic), Penbutolol (Levatol), Pindolol (Visken), Propanolol (Inderal), Sotalol (Betapace), and Timolol (Blocadren)), buspirone (e.g., BuSpar), selective serotonin reuptake inhibitors (SSRIs) (e.g., Paxil (paroxetine), Prozac (fluoxetine), Zoloft (sertraline) and Lexapro (escitalopram)), serotonin-norepinephrine reuptake inhibitors (SNRIs) (e.g., Effexor (venlafaxine), Cymbalta (duloxetine), and Pristiq (desvenlafaxine)), and tricyclic antidepressants (e.g., Tofranil (imipramine), Elavil (amitriptyline), Pamelor (nortriptyline) and Anafranil (clomipramine))).

In some embodiments, the described classification systems can successfully diagnose if an individual has Alzheimer's disease (AD), and can determine if the individual will respond clinically to an Alzheimer's disease (AD) treatment. In some embodiments, the Alzheimer's disease (AD) treatment is selected from the group consisting of cholinesterase inhibitors (e.g., donepezil (Aricept), rivastigmine (Exelon), and galantamine (Razadyne)), memantine (e.g., Namenda), and combinations thereof.

In some embodiments, the described classification systems can successfully diagnose if an individual has Parkinson's disease (PD), and can determine if the individual will respond clinically to a Parkinson's disease (PD) treatment. In some embodiments, the PD treatment is selected from the group consisting of carbidopa-levodopa (e.g., Lodosyn), carbidopa-levodopa infusion (e.g., Duopa), dopamine agonists (e.g, pramipexole (Mirapex), ropinirole (Requip), rotigotine (Neupro), and apomorphine (Apokyn)), MAO B inhibitors (e.g., selegiline (Eldepryl and Zelapar), rasagiline (Azilect) and safinamide (Xadago)), catechol O-methyltransferase (COMT) inhibitors (e.g., entacapone (Comtan) and tolcapone (Tasmar)), anticholinergics (e.g., benztropine (Cogentin) and trihexyphenidyl), amantadine, and combinations thereof.

It is appreciated that methods in accordance with the present disclosure can include any combination of the aspects and features described herein. That is, methods in accordance with the present disclosure are not limited to the combinations of aspects and features specifically described herein, but also may include any combination of the aspects and features provided.

The details of one or more embodiments of the present disclosure are set forth in the accompanying drawings and the description below. Other features and advantages of the present disclosure will be apparent from the description and drawings, and from the claims.

BRIEF DESCRIPTION OF THE DRAWINGS

A better understanding of the features and advantages of the present subject matter will be obtained by reference to the following detailed description that sets forth illustrative embodiments and the accompanying drawings of which:

FIG. 4A depicts a histogram of burst frequency average of hippocampal neuron cultures;

FIG. 4B depicts a histogram of network burst duration average of hippocampal neuron cultures;

FIG. 4C depicts a histogram of number of spikes per network burst average of hippocampal neuron cultures;

FIG. 9A depicts an equation for quantifying synchrony within a network of neurons, the equation quantifies the percentage of neurons in a network have calcium events simultaneously;

DETAILED DESCRIPTION

Figure 1:
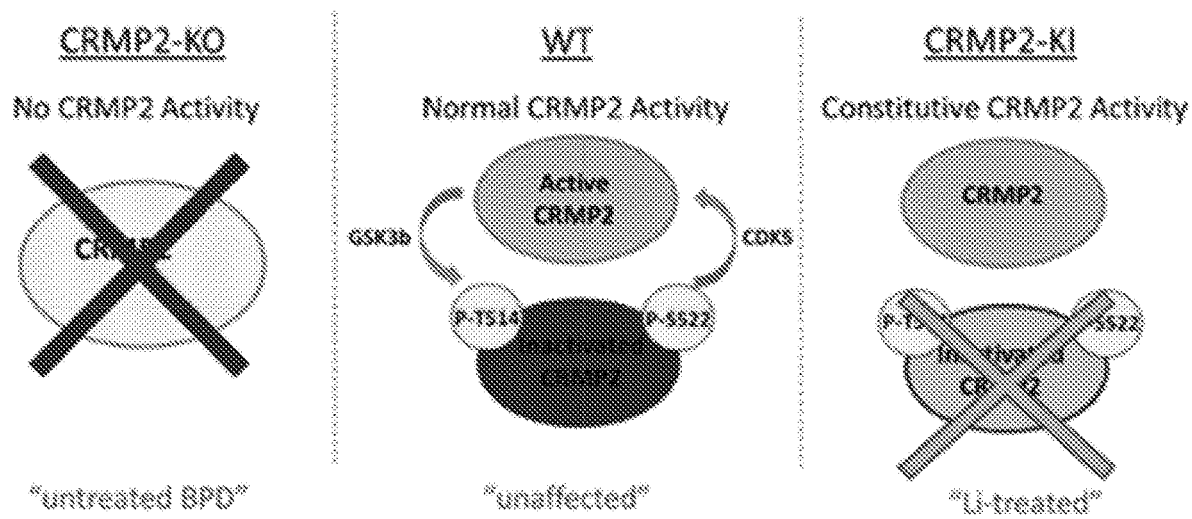
FIG. 1 depicts a diagram explaining the different BPD states each transgenic CRMP2 mouse lines recapitulates.

Described herein, in certain embodiments, are systems for classification systems comprising a user interface; a cellular imaging device; one or more processors; and a computer-readable storage device coupled to the one or more processors and having instructions stored thereon which, when executed by the one or more processors, cause the one or more processors to perform operations comprising: receiving, from the cellular imaging device, image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to the user interface.

Also described herein, in certain embodiments, are non-transitory computer-readable storage media coupled to one or more processors and having instructions stored thereon which, when executed by the one or more processors, cause the one or more processors to perform operations comprising: receiving, from a cellular imaging device, image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to a user interface.

Also described herein, in certain embodiments, are computer-implemented methods for patient screening comprising: receiving, from a cellular imaging device, image data comprising calcium kinetic features of neuronal cultures derived from a patient; processing the image data through a machine-learning model to determine a diagnosis for the patient based on the calcium kinetic features, the machine-learning model trained using neuronal calcium data; and providing the diagnosis to a user interface.

Certain Definitions

Unless otherwise defined, all technical terms used herein have the same meaning as commonly understood by one of ordinary skill in the art to which this disclosure belongs.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "real-time" refers to transmitting or processing data without intentional delay given the processing limitations of a system, the time required to accurately obtain data and images, and the rate of change of the data and images. In some examples, "real-time" is used to describe the presentation of information obtained from components of embodiments of the present disclosure.

System Overview

In some embodiments, the described classification system includes supervised machine learning classification models that can diagnose BPD in patients, as well as predict whether the patient will respond clinically to lithium. In some embodiments, the described classification system employs calcium imaging kinetics data. In some embodiments, the imaging kinetics data is generated in a laboratory. In some embodiments, the described classification system employs five models based off linear regression, naïve Bayes, random forest, one versus all, and KNN algorithms. In some embodiments, KNN is the most accurate model. In some embodiments, the described classification system employs data acquired from in vitro neural cultures derived from human induced pluripotent stem cells isolated from BPD individuals.

In some embodiments, the described classification system trains a machine learning model with BPD neuronal calcium kinetic features such as Basal calcium level, Peak calcium transience, Calcium event amplitude, and Calcium event frequency. In some embodiments, additional calcium kinetic features are employed to train the model, such as calcium event influx, and calcium event efflux.

In some embodiments, the described classification system uses patient derived neuronal cultures. In some embodiments, the calcium kinetics of the neuronal cultures are imaged and the specific calcium kinetic features are analyzed and processed with a trained machine learning model. In some embodiments, the described classification system uses patient blood sample (vs iPSC) for generating the neural cultures for diagnostic analysis.

FIG. 1 depicts a diagram explaining the different BPD states each transgenic CRMP2 mouse lines recapitulates based of previously published mouse behavioral, and the level of CRMP2 activity in each mouse strain.

Figure 2:
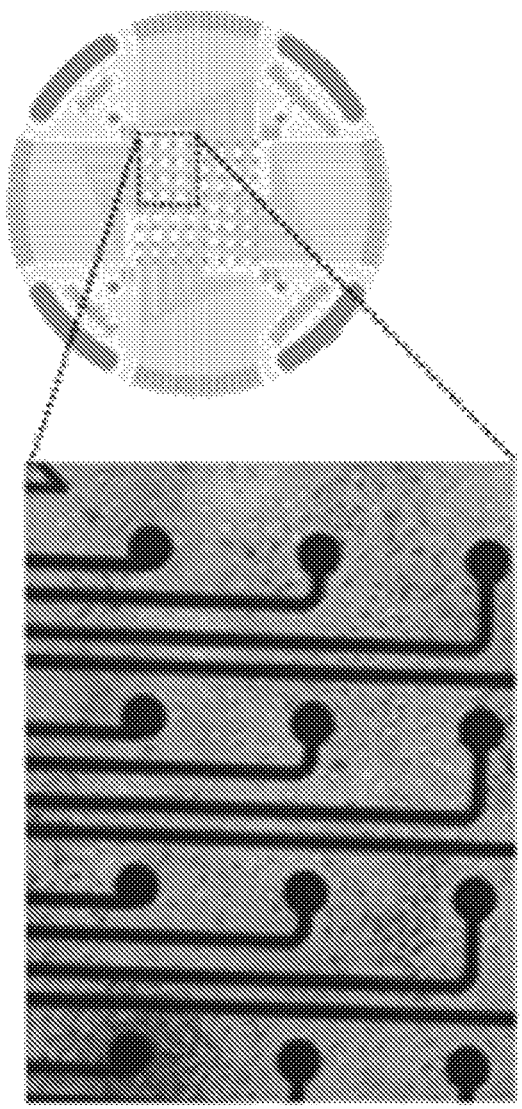
FIG. 2 depicts a diagram of a multi-electrode array (MEA) well from Axion Biosystems.

FIG. 2 depicts a diagram of a multi-electrode array (MEA) well from Axion Biosystems. As depicts each well of a 12-well plate includes 64 electrodes to record continuous voltage potential of neurons seeded on top of the electrode. The magnified view is a 10× micrograph of a primary hippocampal culture, seeded on top of MEA well.

Figure 3:
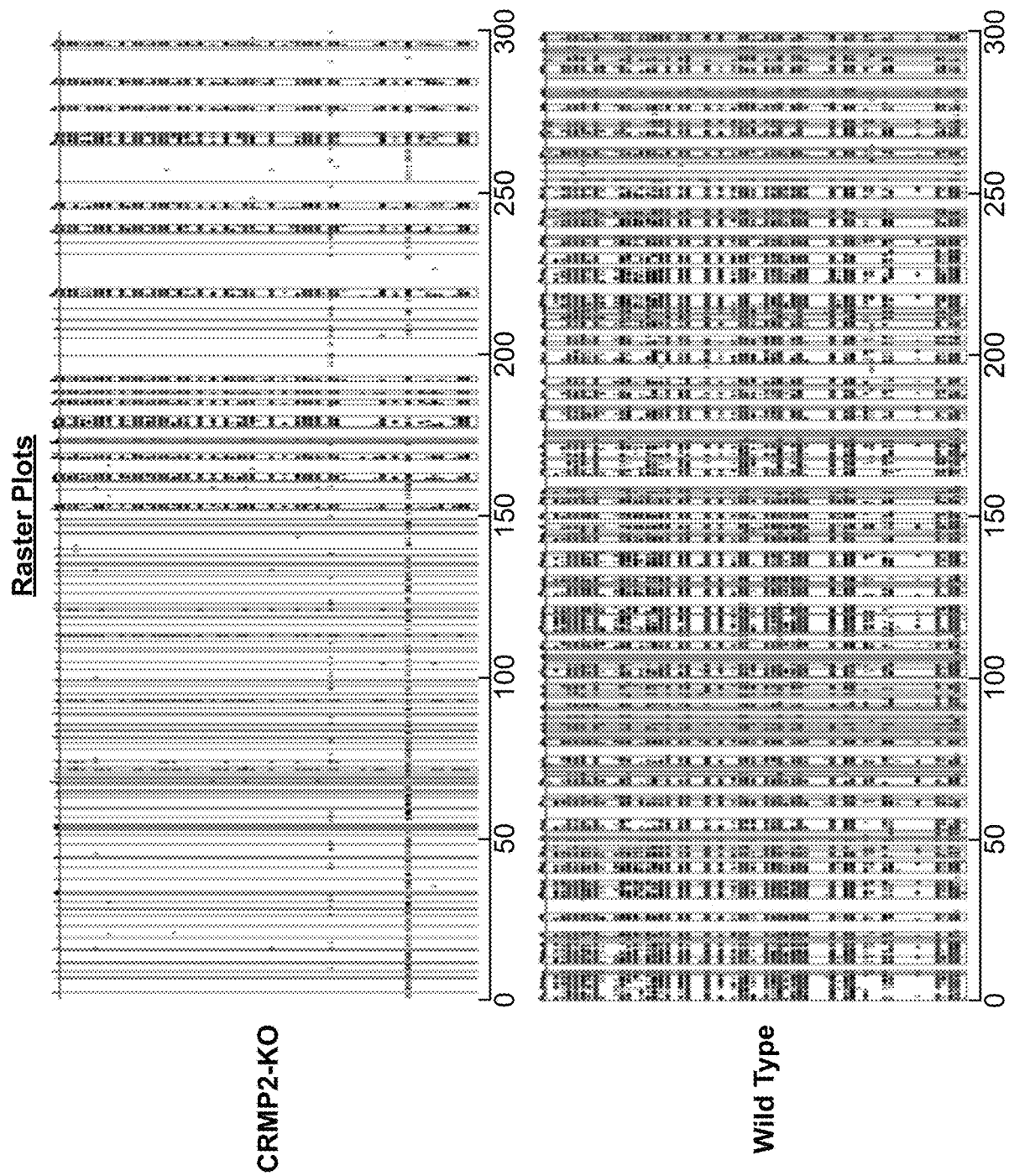
FIG. 3 depicts a representative raster plots of spontaneous MEA signaling behavior.

FIG. 3 depicts a representative raster plots of spontaneous MEA signaling behavior over 5 minutes of genetically paired CRMP2-KO and WT primary hippocampal cultures; CRMP2-KO neurons exhibit less signaling than WT neurons. As depicted, black dashes represent single action potentials (e.g., spikes), blue represents multi-neuronal network signaling event spikes, purple represents synchronized spikes from multiple neurons.

FIG. 4A depicts a histogram of burst frequency average of hippocampal neuron cultures. As depicted, burst frequency is a measure of how often individual spikes of a single neuron can be grouped into bursts, to evaluate action potential activity.

FIG. 4B depicts a histogram of network burst duration average of hippocampal neuron cultures. As depicted, network burst duration is a measure of the length of time for bursting activity that occurs both within a small time period and simultaneously across multiple neurons.

FIG. 4C depicts a histogram of number of spikes per network burst average of hippocampal neuron cultures. In some embodiments, the number of network spikes is a quantity of spikes during a neuronal network signaling event. One way ANOVA, error bars are SEM, n<600 network burst per group and n=268 active neurons analyzed per group ($*p \leq 0.05$; $p \leq 0.01$; $*p \leq 0.001$).

Figure 5A:
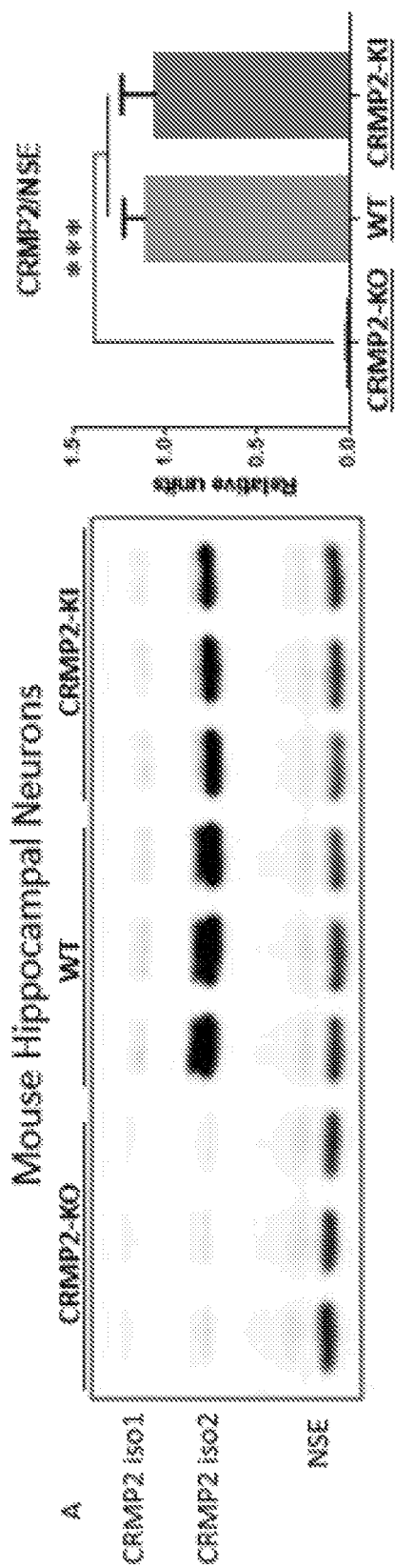
FIG. 5A depicts a representative western blot and quantification of CRMP2 protein levels in WT, CRMP2-KO, and CRMP2-KO mouse primary hippocampal neurons.

FIG. 5A depicts a representative western blot and quantification of CRMP2 protein levels in WT, CRMP2-KO, and CRMP2-KO mouse primary hippocampal neurons. In some embodiments, CRMP2-KO neurons have negligible levels of CRMP2, while CRMP2-KI neurons have levels similar to WT.

Figure 5B:
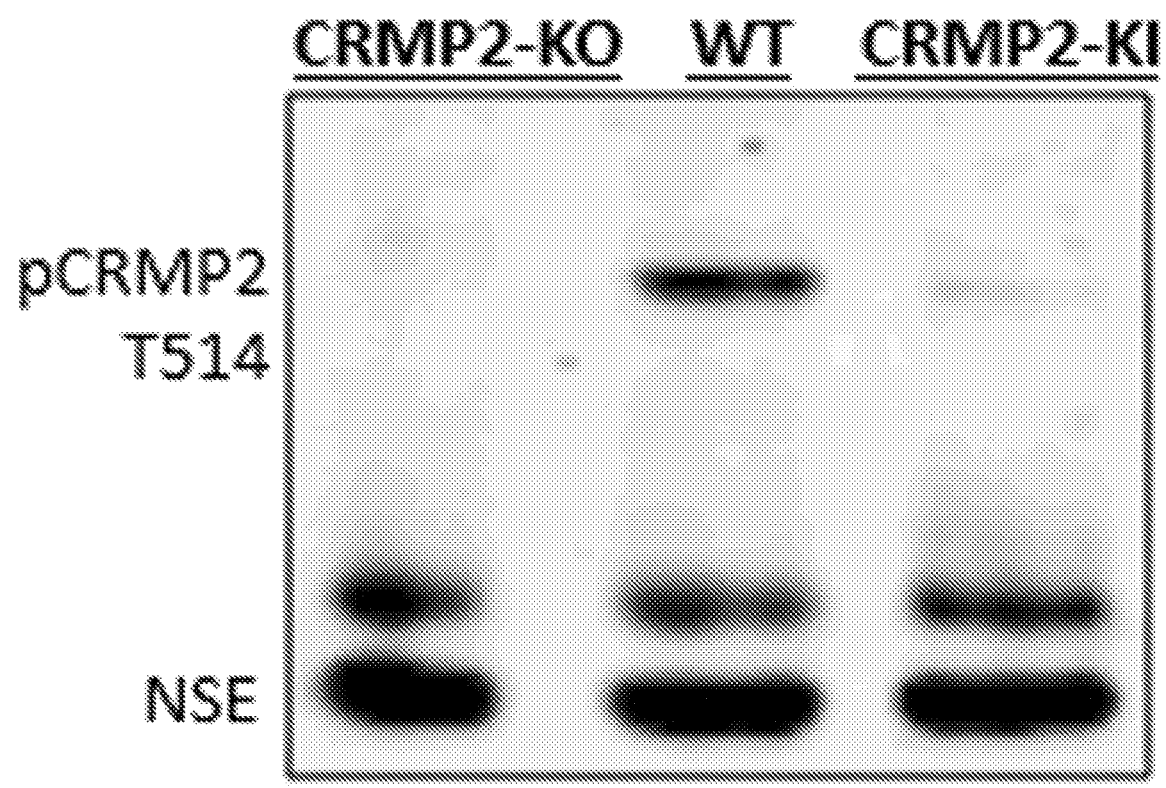
FIG. 5B depicts representative western blot of pCRMP2-T514 levels in WT, CRMP2-KO, and CRMP2-KO mouse primary hippocampal neurons.

FIG. 5B depicts representative western blot of pCRMP2-T514 levels in WT, CRMP2-KO, and CRMP2-KO mouse primary hippocampal neurons. Both CRMP-KO and CRMP2-KI neurons lack the phosphorylated form of CRMP2 at Theonine-514.

Figure 5C:
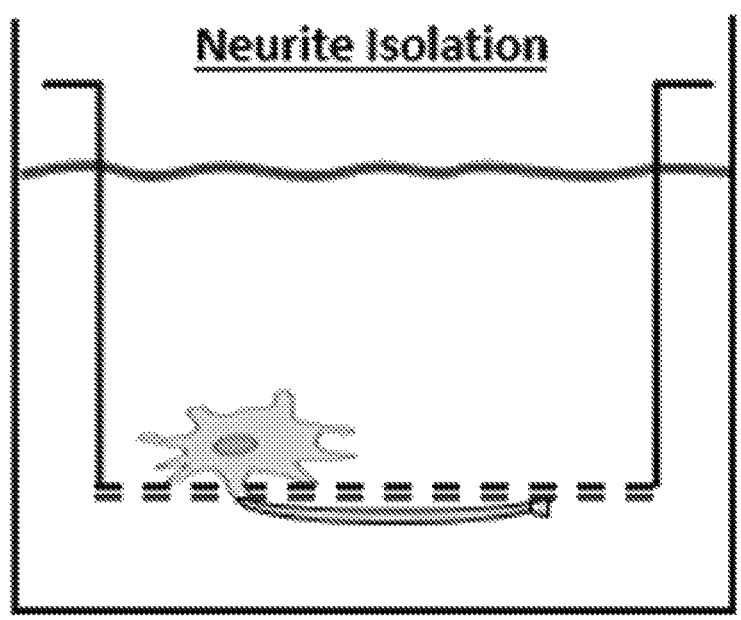
FIG. 5C depicts a diagram of method for isolating neurites from in vitro cultures.

FIG. 5C depicts a diagram of method for isolating neurites from in vitro cultures. In some embodiments, the bottom of well-insert with 3.0 um pores is coated with laminin (red) which attracts neurites to grow spatially separated from soma of neurons.

Figure 5D:
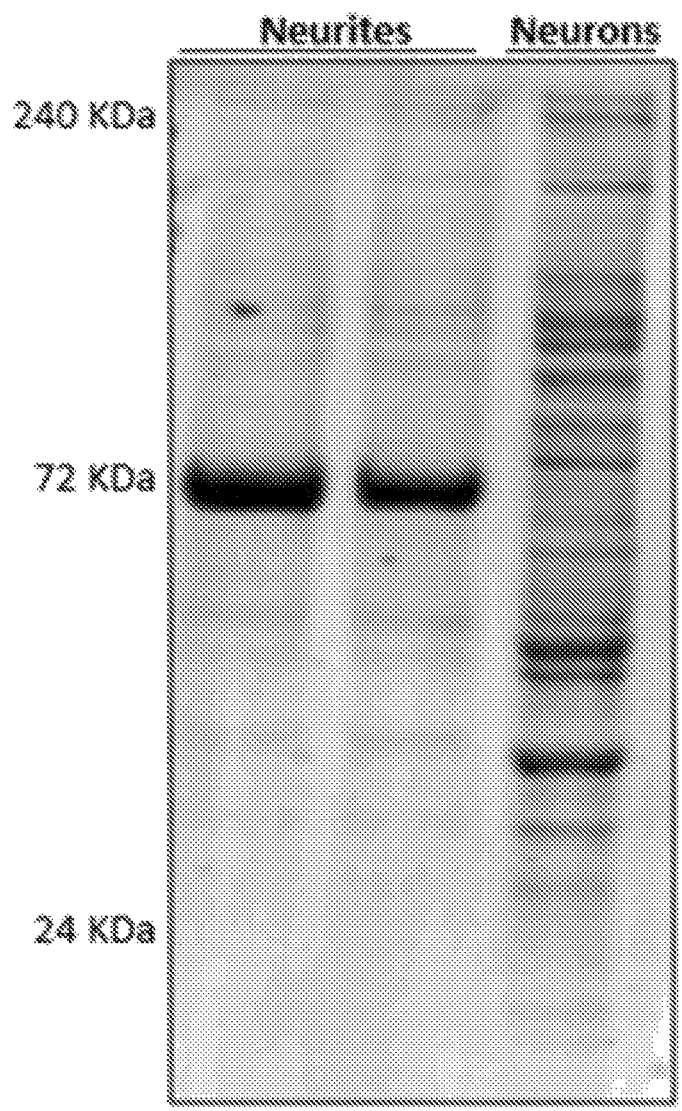
FIG. 5D depicts a Coomassie stain representative of SDS-PAGE gel containing whole proteome isolated from neurite isolation replicates and whole neurons from the same primary hippocampal cultures.

FIG. 5D depicts a Coomassie stain representative of SDS-PAGE gel containing whole proteome isolated from neurite isolation replicates and whole neurons from the same primary hippocampal cultures. In some embodiments, the gel demonstrates neurite proteome is distinct from whole neurons, and that the neurite isolation protocol is repeatable.

Figure 5E:
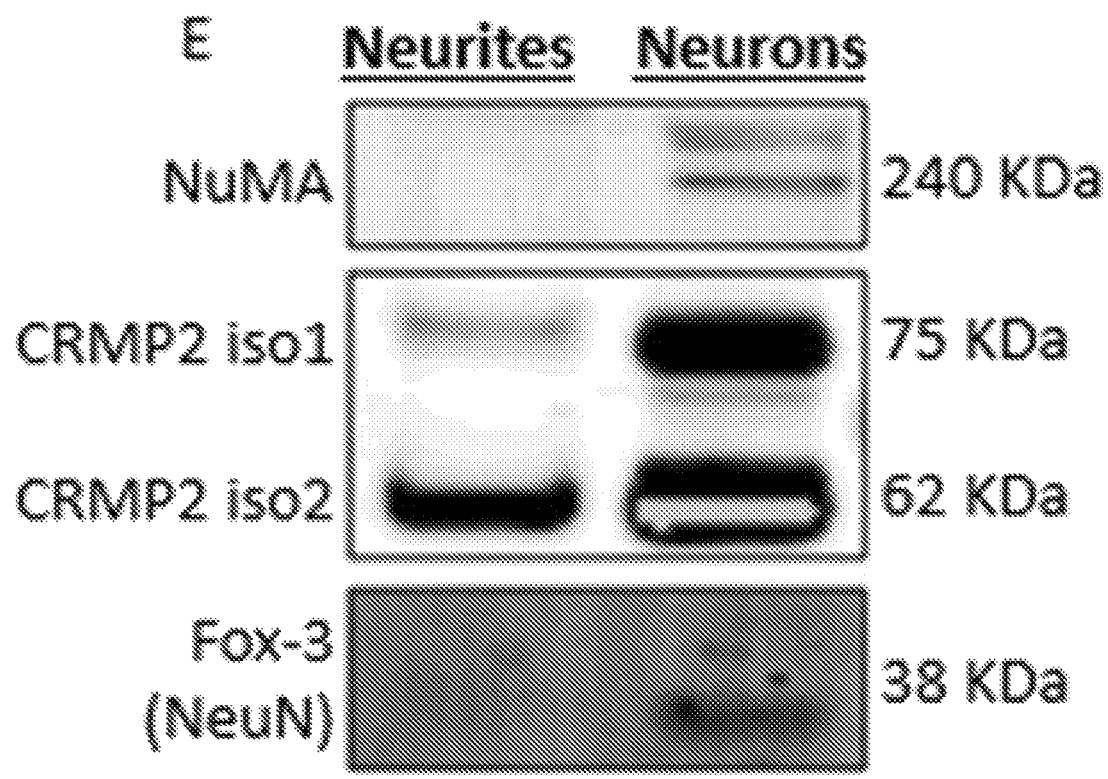
FIG. 5E depicts a representative western blots of nuclear proteins Fox-3 (NeuN) and Nuclear Mitotic Apparatus (NuMA)

FIG. 5E depicts a representative western blots of NeuN and NuMA, demonstrating nuclei and associated proteins are excluded in the isolated neurites. In some embodiments, CRMP2 is present in isolated neurites.

Figure 5F:
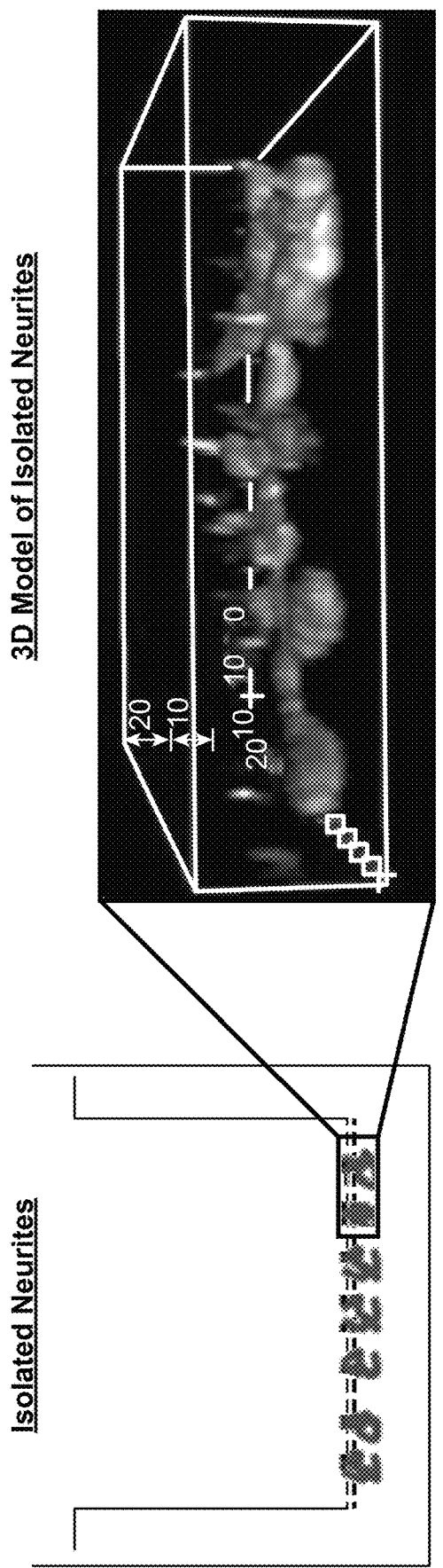
FIG. 5F depicts a Diagram and three dimensional (3D) reconstruction of imaged isolated neurites stained with Tuj1.

FIG. 5F depicts a Diagram and 3D reconstruction of imaged isolated neurites stained with Tuj1.

Figure 6A:
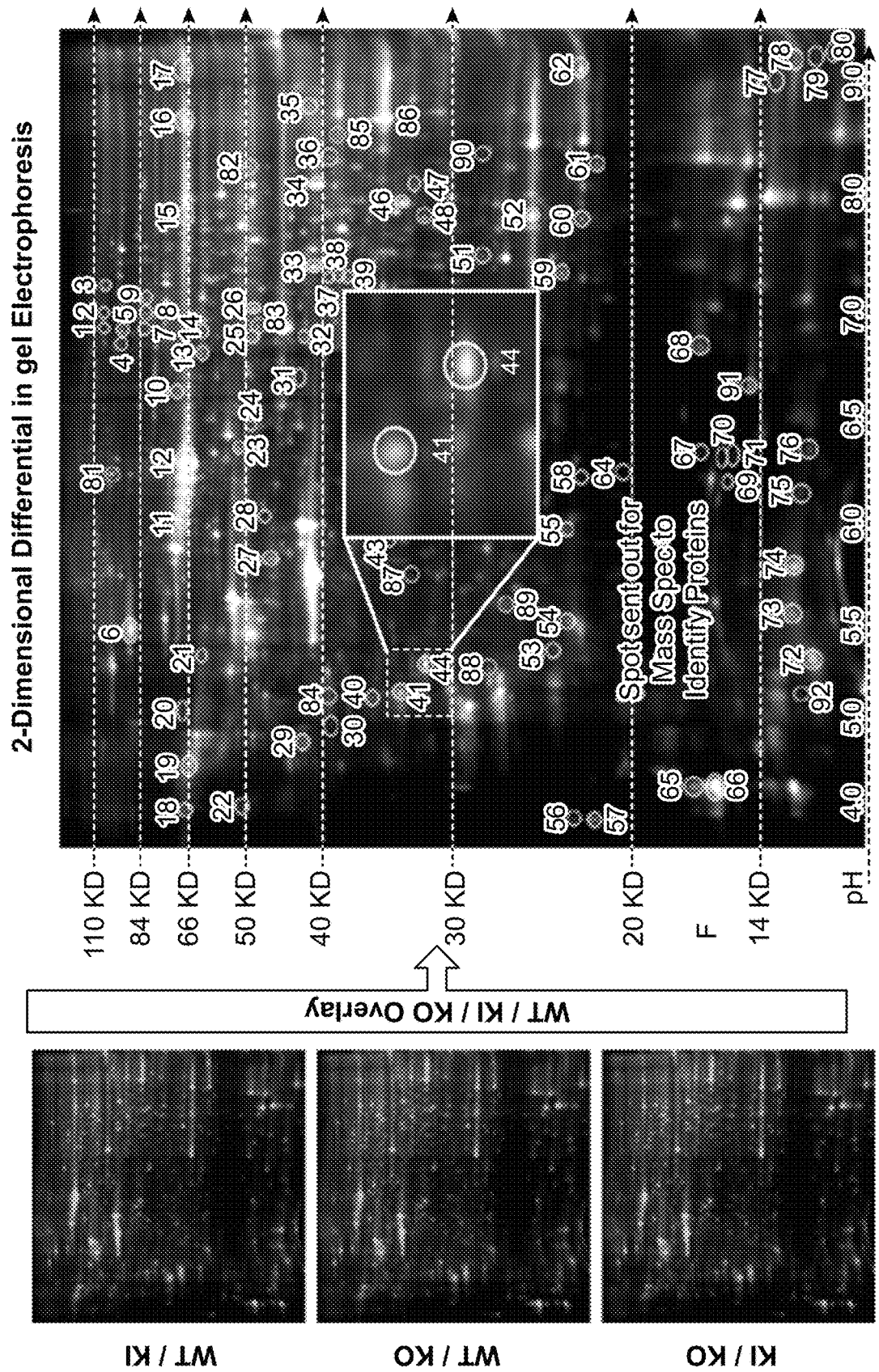
FIG. 6A depicts differential proteomic analysis by two-dimensional (2D) differential in gel electrophoresis (2D-DIGE) of neurites isolated from WT, CRMP2-KO, and CRMP-KI primary hippocampal neurons.

FIG. 6A depicts differential proteomic analysis by 2D-DIGE of neurites isolated from WT, CRMP2-KO, and CRMP-KI primary hippocampal neurons. In some embodiments, neurite proteomes from WT (stained with Cy2), CRMP2-KI (stained with Cy3), and CRMP2-KO (stained with Cy5) were compared in the same gel, with proteins separated based on their molecular weight, charge, and degree of enrichment under each condition. In some embodiments, in an overlay of the images of each proteome regions where the proteome is shared between all three backgrounds are white, while protein differentially altered by CRMP2 activity are colored either blue (WT), green (CRMP2-KI), or red (CRMP2-KO) depending on which source the protein is more abundant in. Differential protein spots (encircled white) were picked and identified via mass spectrometry.

Figure 6B:
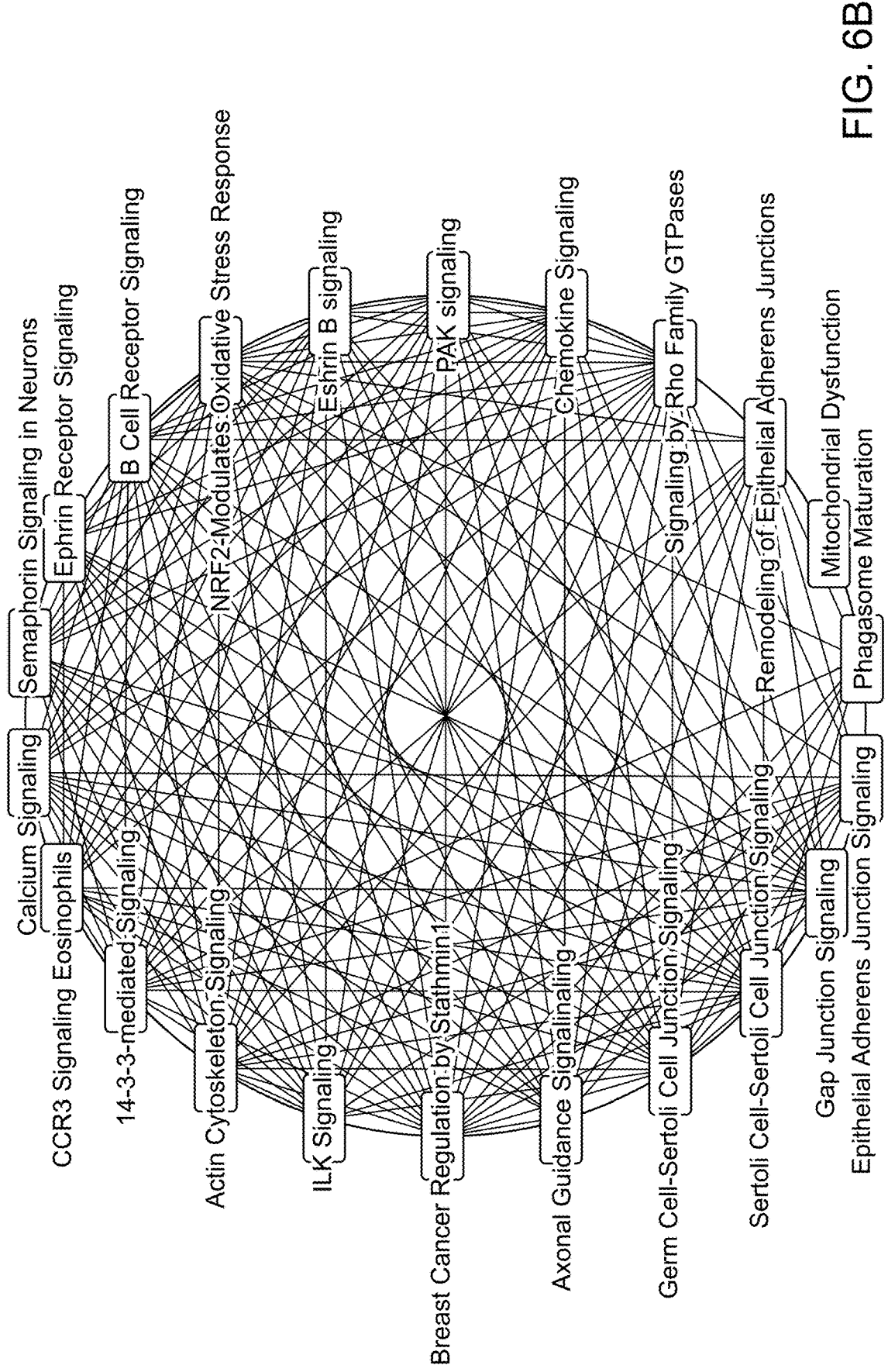
FIG. 6B depicts an unbiased canonical pathway map constructed from the proteins identified by the 2D-DIGE using Ingenuity-IPA analysis.

FIG. 6B depicts an unbiased canonical pathway map constructed from the proteins identified by the 2D-DIGE using Ingenuity-IPA analysis, which are neurites proteins regulated by CRMP2. In some embodiments, calcium signaling is predicted to be a major pathway impacted by CRMP2 associated neurite proteins.

Figure 6C:
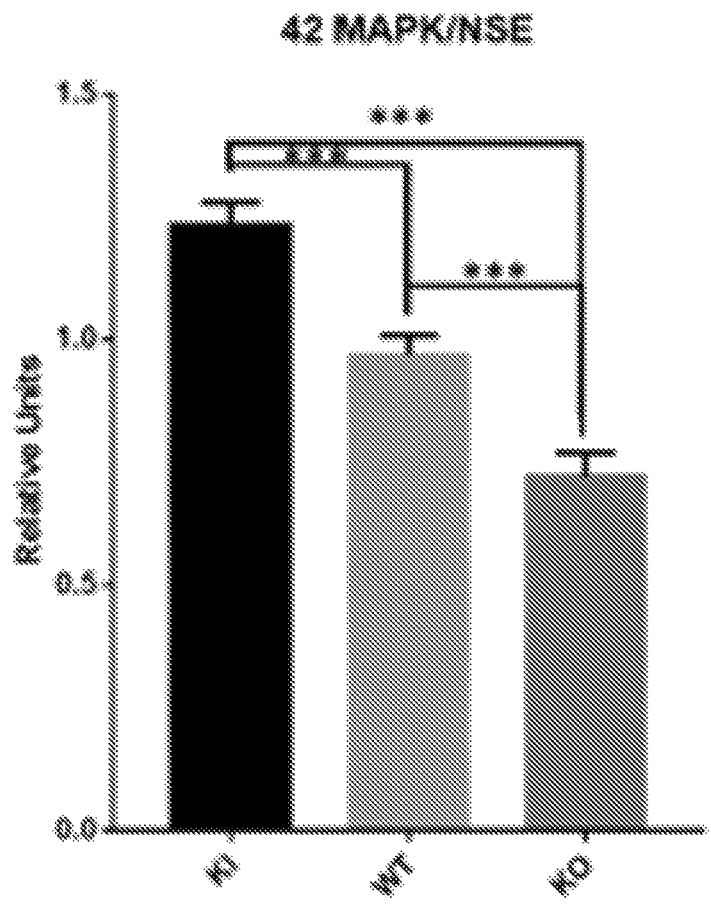
FIG. 6C depicts a histogram of Mitogen-activated protein kinases (MAPK)

FIG. 6C depicts a histogram of MAPK, a protein identified in the 2D-DIGE and subsequential bioinformatic analysis, levels in CRMP2-KI, WT, and CRMP2-KO mouse primary hippocampal neurites, measured from western blots via densitometry. Neural Specific Enolase (NSE) has used as a neuronal loading control, n of 6 per group, one way ANOVA, error bars are SEM ($*p \leq 0.05$; $p \leq 0.01$; $*p \leq 0.001$).

Figure 6D:
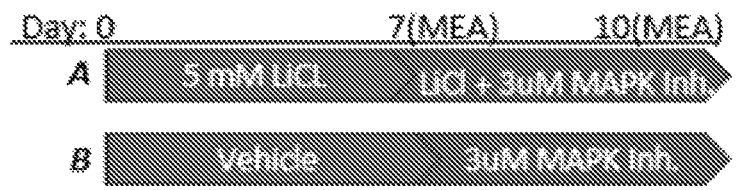
FIG. 6D depicts a diagram detailing the design and timeline of a MAPK inhibitor impact on neuronal network signaling as measured via MEA with hiPSC derived neural cultures.

FIG. 6D depicts a diagram detailing the design and timeline of a MAPK inhibitor (Pyrazolylpyrrole) impact on neuronal network signaling as measured via MEA with hiPSC derived neural cultures. In some embodiments, group A is treated with 5 mM LiCl and has its signaling recorded at day seven, and afterwards is treated with 3 uM Pyrazolylpyrrole for three days until observed on MEA at day 10. In some embodiments, Group B is treated with vehicle and has its signaling recorded at day seven, and afterwards is treated with 3 uM Pyrazolylpyrrole for three days until observed on MEA at day 10.

Figure 6E:
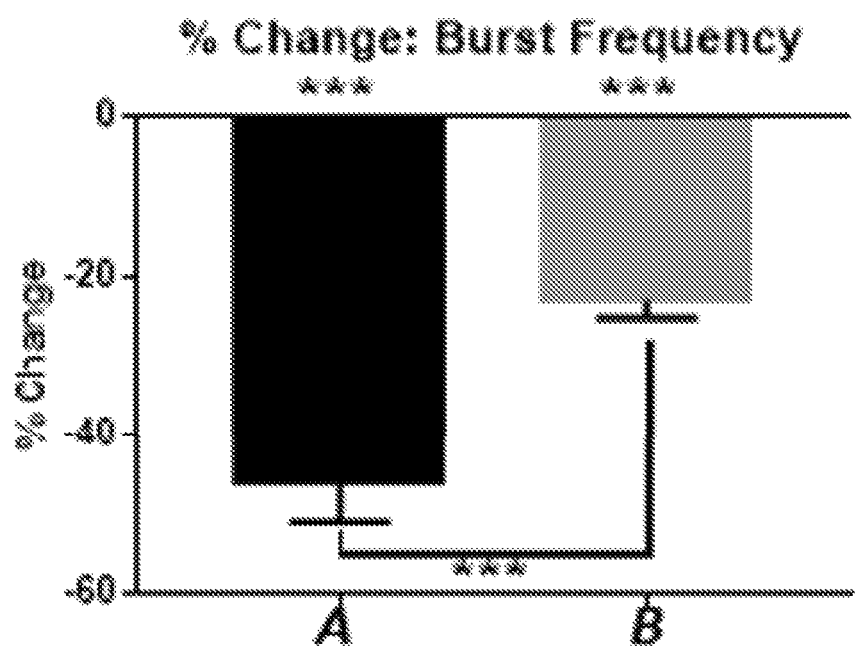
FIGS. 6E-F depict quantifications on the impact of MAPK inhibition on neuronal network signaling dynamics.
Figure 6F:
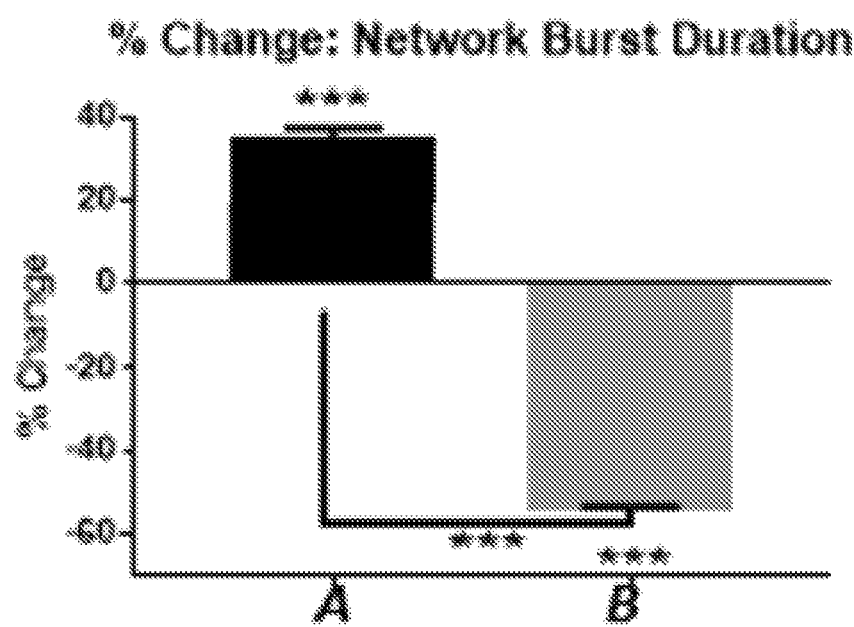

FIGS. 6E-F depict quantifications on the impact of MAPK inhibition on neuronal network signaling dynamics, histograms are of the percent change from day seven to day 10 for burst frequency, network burst duration, and number of spikes per network burst respectively. One way ANOVA, error bars are SEM, n<150 network burst per group and n=80 active electrodes analyzed per group ($*p \leq 0.05$; $p \leq 0.01$; $*p \leq 0.001$).

Table 1 includes quantifications for each form of tubulin protein. Table 1 includes 59 neurite-proteins impacted by CRMP2 activity, as identified by the 2D-DIGE and subsequent mass spectrometry. Gray labeled proteins were elevated increased in CRMP2-KI versus WT neurites, orange labeled proteins were elevated increased in CRMP2-KI versus CRMP2-KO neurites. In some embodiments, Tubulin proteins identified via mass spectrometry share the same fold changes because they were from the same spot of the 2D-DIGE gel, preventing proper fold change.

TABLE 1

| Ingenuity ID | Symbol | Entrez Gene Name | Location | Fold Increase(s) | Type(s) |
| --- | --- | --- | --- | --- | --- |
| ACOT1_MOUSE | Acot1 | acyl-CoA thioesterase 1 | Cytoplasm | WT/KO = 5.67<br>KI/KO = 5.24 | enzyme |
| PPAC_MOUSE | ACP1 | acid phosphatase 1 | Cytoplasm | WT/KO = 3.09<br>KI/KO = 2.78 | phosphatase |
| ACTG_MOUSE | ACTG1 | actin gamma 1 | Cytoplasm | KI/KO = 2.12<br>WT/KO = 1.65 | other |
| AKCL2_MOUSE | AKR1E2 | aldo-keto reductase family 1 member E2 | Cytoplasm | WT/KO = 4.16 | enzyme |
| ANXA5_MOUSE | ANXA5 | annexin A5 | Plasma Membrane | KI/WT = 1.87 | transporter |

TABLE 1-continued

| Ingenuity ID | Symbol | Entrez Gene Name | Location | Fold Increase(s) | Type(s) |
|---|---|---|---|---|---|
| CALM1_MOUSE | Calm1 (includes others) | calmodulin 1 | Nucleus | KO/KI = 5.09 KI/WT = 2.64 | other |
| CALL3_MOUSE | CALML3 | calmodulin like 3 | Cytoplasm | KO/KI = 3.01 KI/WT = 1.83 | other |
| CALU_MOUSE | CALU | calumenin | Cytoplasm | WT/KO = 2.68 KI/KO = 2.09 | other |
| COF1_MOUSE | CFL1 | cofilin 1 | Nucleus | WT/KO = 2.10 KI/KO = 2.02 | other |
| COF2_MOUSE | CFL2 | cofilin 2 | Extracellular Space | WT/KO = 2.10 KI/KO = 2.02 | other |
| KCRB_MOUSE | CKB | creatine kinase B | Cytoplasm | KI/KO = 5.24 WT/KO = 5.67 | kinase |
| CNN2_MOUSE | CNN2 | calponin 2 | Cytoplasm | WT/KO = 3.64 KI/KO = 2.49 | other |
| COX5A_MOUSE | COX5A | cytochrome c oxidase subunit 5A | Cytoplasm | WT/KO = 3.63 KI/KO = 3.04 | enzyme |
| CYB5B_MOUSE | CYB5B | cytochrome b5 type B | Cytoplasm | WT/KO = 3.03 KI/KO = 2.04 | enzyme |
| DPYL2_MOUSE | CRMP2 | dihydropyrimidinase like 2 (collapsin response mediator protein-2) | Cytoplasm | WT/KO = 11.58 KI/KO = 9.4 | enzyme |
| ERP29_MOUSE | ERP29 | endoplasmic reticulum protein 29 | Cytoplasm | KI/KO = 1.94 WT/KO = 1.66 | transporter |
| FABP7_MOUSE | FABP7 | fatty acid binding protein 7 | Cytoplasm | WT/KO = 3.63 KI/KO = 3.04 | transporter |
| FIS1_MOUSE | FIS1 | fission, mitochondrial 1 | Cytoplasm | KI/WT = 2.04 | other |
| FRIL1_MOUSE | FTL | ferritin light chain | Cytoplasm | WT/KO = 4.05 KI/KO = 3.42 | enzyme |
| GFAP_MOUSE | GFAP | glial fibrillary acidic protein | Cytoplasm | WT/KO = 2.44 KI/KO = 2.41 | other |
| LGUL_MOUSE | GLO1 | glyoxalase 1 | Cytoplasm | KI/WT = 1.53 | enzyme |
| GLNA_MOUSE | GLUL | glutamate-ammonia ligase | Cytoplasm | KI/KO = 2.12 WT/KO = 1.65 | enzyme |
| GPDM_MOUSE | GPD2 | glycerol-3-phosphate dehydrogenase 2 | Cytoplasm | WT/KO = 4.65 KI/KO = 2.05 | enzyme |
| GSTA4_MOUSE | Gsta4 | glutathione S-transferase, alpha 4 | Other | KI/WT = 1.61 | enzyme |
| HDGF_MOUSE | HDGF | heparin binding growth factor | Extracellular Space | WT/KO = 2.31 KI/KO = 1.72 | growth factor |
| H2A1H_MOUSE | HIIST1H2AH | histone cluster 1 H2A family member h | Nucleus | KI/WT = 1.66 | other |
| H2B3B_MOUSE | HIIST3H2BB | histone cluster 3 H2B family member b | Nucleus | KI/WT = 2.04 | other |
| HMCS1_MOUSE | HMGCS1 | 3-hydroxy-3-methylglutaryl-CoA synthase 1 | Cytoplasm | WT/KO = 2.30 KI/KO = 2.09 | enzyme |
| HSP7C_MOUSE | HSPA8 | heat shock protein family A (Hsp70) member 8 | Cytoplasm | WT/KO = 4.65 KI/KO = 2.05 | enzyme |
| IBP2_MOUSE | IGFBP2 | insulin like growth factor binding protein 2 | Extracellular Space | WT/KO = 1.76 KI/KO = 1.50 | other |
| LEG1_MOUSE | LGALS1 | galectin 1 | Extracellular Space | WT/KO = 2.49 KI/KO = 2.18 | other |
| MK01_MOUSE | MAPK1 | mitogen-activated protein kinase 1 | Cytoplasm | KI/WT = 1.56 | kinase |
| MK03_MOUSE | MAPK3 | mitogen-activated protein kinase 3 | Cytoplasm | KI/WT = 1.56 | kinase |
| MARCS_MOUSE | Marcks | myristoylated alanine rich protein kinase C substrate | Plasma Membrane | WT/KO = 5.31 KI/KO = 1.94 | other |
| PA1B2_MOUSE | PAFAH1B2 | platelet activating factor acetylhydrolase 1b catalytic subunit 2 | Cytoplasm | KO/WT = 2.11 KI/KO = 2.38 | enzyme |
| PRDX1_MOUSE | PRDX1 | peroxiredoxin 1 | Cytoplasm | WT/KO = 2.53 KI/KO = 2.54 | enzyme |
| PRDX5_MOUSE | PRDX5 | peroxiredoxin 5 | Cytoplasm | KI/WT = 2.04 | enzyme |
| PRPS2_MOUSE | PRPS2 | phosphoribosyl pyrophosphate synthetase 2 | Cytoplasm | WT/KO = 1.76 KI/KO = 1.50 | kinase |
| PSIP1_MOUSE | PSIP1 | PC4 and SFRS1 interacting protein 1 | Nucleus | WT/KO = 2.31 KI/KO = 1.72 | transcription regulator |
| PS86_MOUSE | PSM86 | proteasome subunit beta 6 | Nucleus | KI/WT = 1.53 | peptidase |

TABLE 1-continued

| Ingenuity ID | Symbol | Entrez Gene Name | Location | Fold Increase(s) | Type(s) |
|---|---|---|---|---|---|
| PSME1_MOUSE | PSME1 | proteasome activator subunit 1 | Cytoplasm | KO/WT = 2.11<br>KI/KO = 2.38 | other |
| PTMA_MOUSE | Ptma (includes others) | prothymosin alpha | Nucleus | KO/WT = 15.6<br>KO/KI = 11.4 | other |
| RLA1_MOUSE | Rplp1 (includes others) | ribosomal protein, large, P1 | Nucleus | KO/KI = 5.09<br>KO/WT = 1.96 | other |
| RSPH1_MOUSE | RSPH1 | radial spoke head 1 homolog | Nucleus | KO/KI = 1.89<br>KO/WT = 1.94 | other |
| SAT2_MOUSE | SAT2 | spermidine/spermine N1-acetyltransferase family member 2 | Plasma Membrane | WT/KO = 4.05<br>KI/KO = 3.42 | enzyme |
| SMD3_MOUSE | SNRPD3 | small nuclear ribonucleoprotein D3 polypeptide | Nucleus | KI/WT = 1.66 | other |
| STMN1_MOUSE | STMN1 | stathmin 1 | Cytoplasm | WT/KO = 2.03<br>KI/KO = 2.12 | other |
| TAGL_MOUSE | TAGLN | Transgelin | Cytoplasm | WT/KO = 2.53<br>KI/KO = 2.54 | other |
| TKT_MOUSE | TKT | Transketolase | Cytoplasm | WT/KO = 4.16<br>KI/KO = 1.75 | enzyme |
| TPM1_MOUSE | Tpm1 | tropomyosin 1, alpha | Plasma Membrane | WT/KO = 2.57<br>KI/KO = 1.87 | other |
| TPM2_MOUSE | Tpm2 | tropomyosin 2, beta | Cytoplasm | WT/KO = 2.31<br>KI/KO = 1.72 | other |
| TBB5_MOUSE | TUBB | tubulin beta class I* | Cytoplasm | WT/KO = 4.39<br>KI/KO = 1.85 | other |
| TBB1_MOUSE | TUBB1 | tubulin beta 1 class VI* | Cytoplasm | WT/KO = 4.39<br>KI/KO = 1.85 | other |
| TBB2B_MOUSE | TUBB2B | tubulin beta 2B class Iib* | Cytoplasm | WT/KO = 4.39<br>KI/KO = 1.85 | other |
| TBB3_MOUSE | TUBB3 | tubulin beta 3 class III* | Cytoplasm | WT/KO = 4.39<br>KI/KO = 1.85 | other |
| TBB4A_MOUSE | TUBB4A | tubulin beta 4A class Iva* | Cytoplasm | WT/KO = 4.39<br>KI/KO = 1.85 | other |
| TBB4B_MOUSE | TUBB4B | tubulin beta 4B class Ivb* | Cytoplasm | WT/KO = 4.39<br>KI/KO = 1.85 | other |
| TBB6_MOUSE | TUBB6 | tubulin beta 6 class V* | Cytoplasm | WT/KO = 4.39<br>KI/KO = 1.85 | other |
| VIME_MOUSE | VIM | vimentin | Cytoplasm | WT/KO = 2.57<br>KI/KO = 1.87 | other |

Figure 7A:
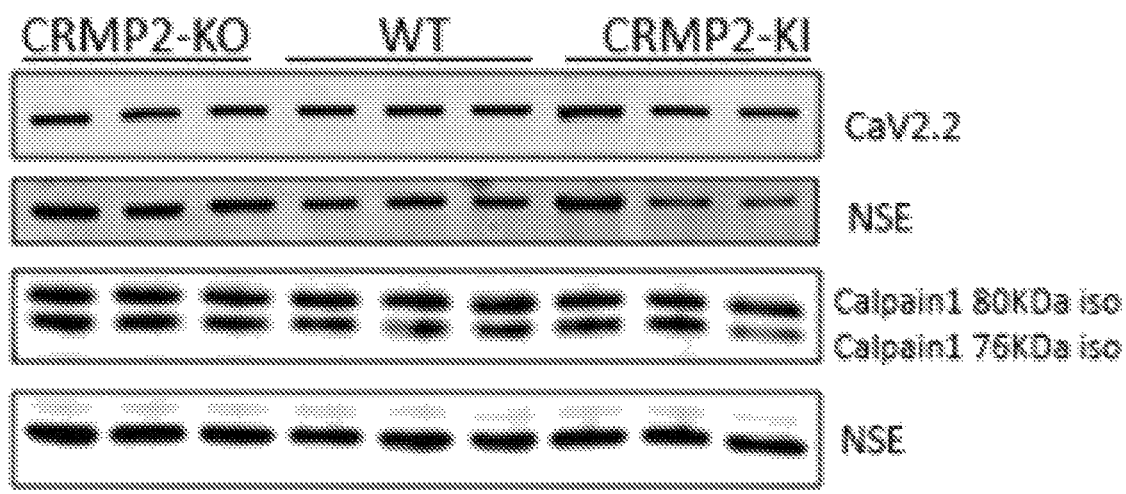
FIG. 7A depicts CRMP2's impact on neuronal calcium function.

FIG. 7A depicts CRMP2's impact on neuronal calcium function. A Western Blot of CaV2.2 and calpain1 protein levels in CMRMP2-KI, WT, and CRMP2-KO mouse primary hippocampal neurites.

Figure 7B:
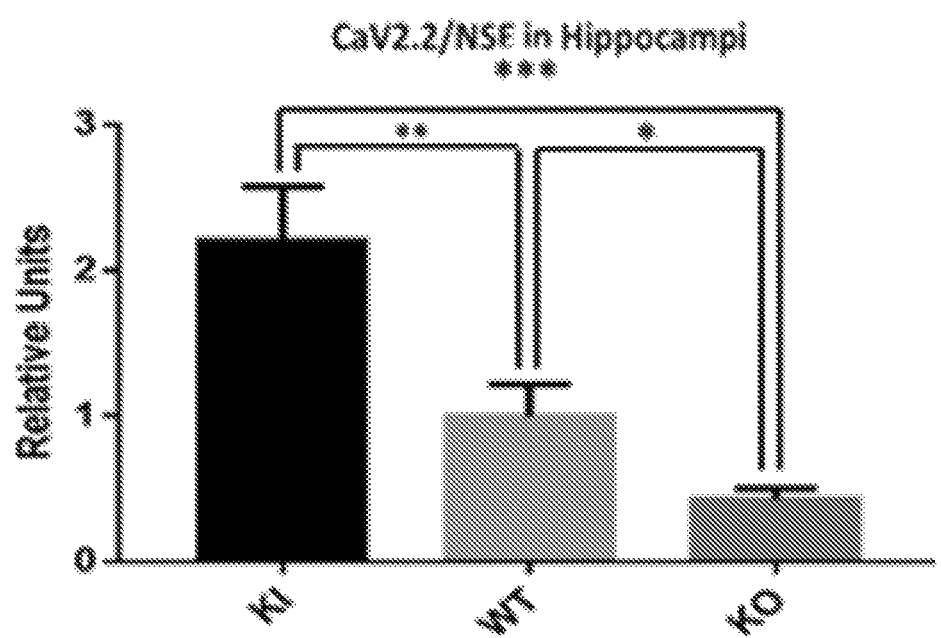
FIG. 7B depicts a histogram of Cav2.2 in CMRMP2-KI, WT, and CRMP2-KO mouse primary hippocampal neurons, measured via densitometry.

FIG. 7B depicts a histogram of Cav2.2 in CMRMP2-KI, WT, and CRMP2-KO mouse primary hippocampal neurons, measured via densitometry.

Figure 7C:
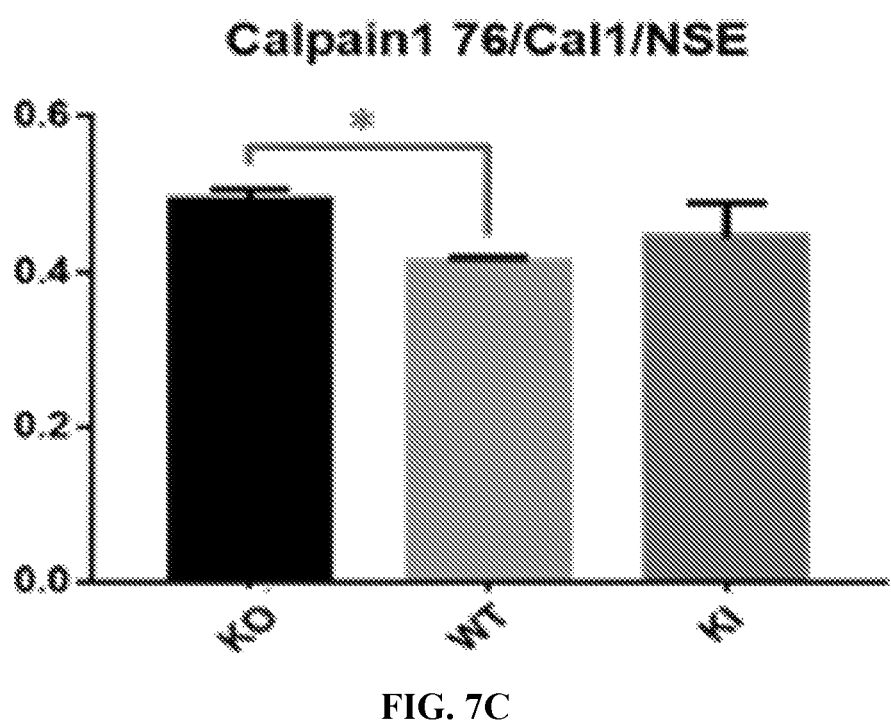
FIG. 7C depicts a histogram of activated calpain levels in CMRMP2-KI, WT, and CRMP2-KO mouse primary hippocampal neurons.

FIG. 7C depicts a histogram of activated calpain levels in CMRMP2-KI, WT, and CRMP2-KO mouse primary hippocampal neurons, which is determined by the ratio of the 76 KDa band over 80 Kda band of calpain, measured via densitometry. Neural Specific Enolase (NSE) has used as a neuronal loading control, n of 6 per group, one way ANOVA, error bars are SEM ($*p \leq 0.05$; $p \leq 0.01$; $*p \leq 0.001$).

Figure 7D:
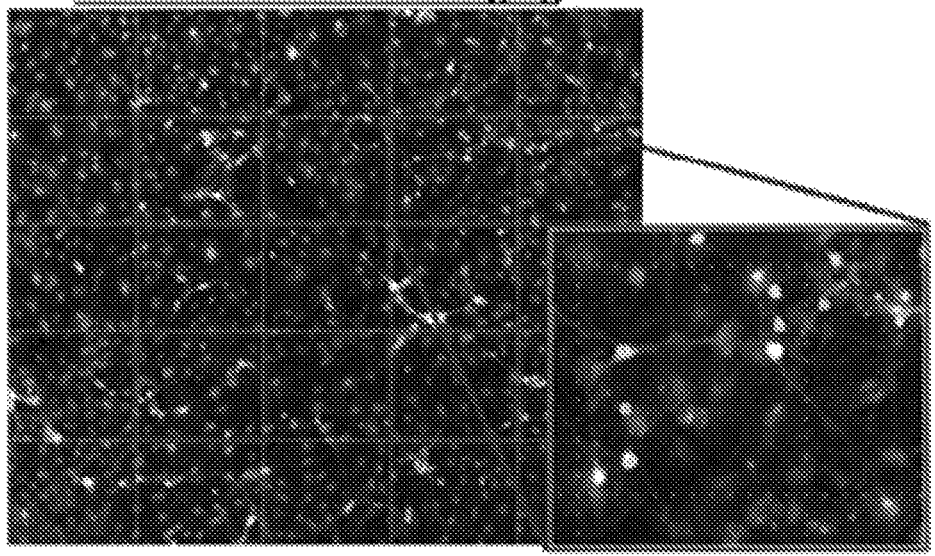
FIG. 7D depicts a representative image from IC200 Kinetic Image Cytometer Flou-4AM calcium imaging of mouse primary hippocampal cultures.

FIG. 7D depicts a representative image from IC200 Kinetic Image Cytometer (Vala Sciences, Inc.) Flou-4AM calcium imaging (30 seconds at 30 frame per second) of mouse primary hippocampal cultures, each field of view had four selected quadrants (red boxes) where neurons were traced in ImageJ (yellow circles), which fluorescent intensity were measure as an equivalent for intracellular calcium levels.

Figure 7E:
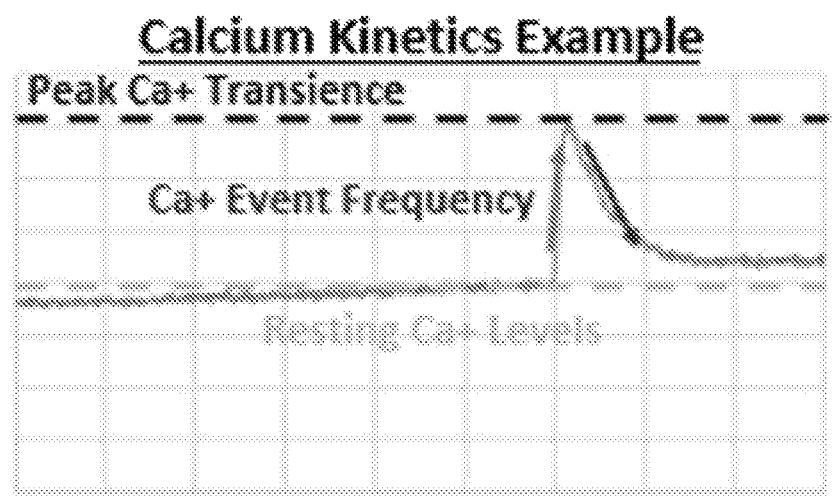
FIG. 7E depicts an example of a single neuron's calcium kinetics.

FIG. 7E depicts an example of a single neuron's calcium kinetics trace (Flou-4AM intensity) from ImageJ analysis. Multiple calcium signaling phenomena are capable of being quantified from this approach, peak calcium transience during a calcium event, frequency of calcium events, relative basal calcium levels, rate of calcium influx during an event, and rate of calcium efflux during an event.

Figure 7F:
FIG. 7F depicts Representative calcium trace examples.

FIG. 7F depicts Representative calcium trace examples from CRMP2KI (green), WT (blue), and CRMP2-KO (red) hippocampal neurons; level of CRMP2 activity appears to have a directional effect on frequency of calcium events.

Figure 7G:
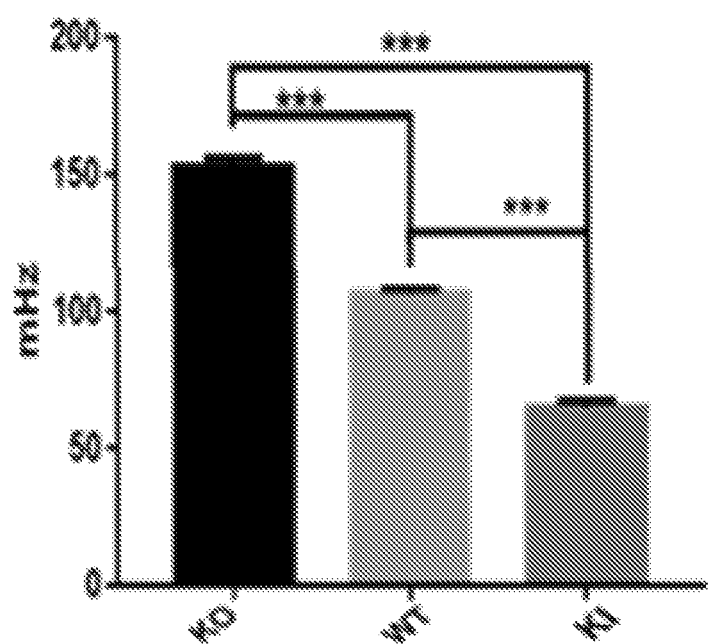
FIG. 7G depicts a histogram of calcium event frequency in hippocampal neurons.

FIG. 7G depicts a histogram of calcium event frequency in hippocampal neurons; decreasing levels of CRMP2 appears to increase calcium event frequency.

Figure 7H:
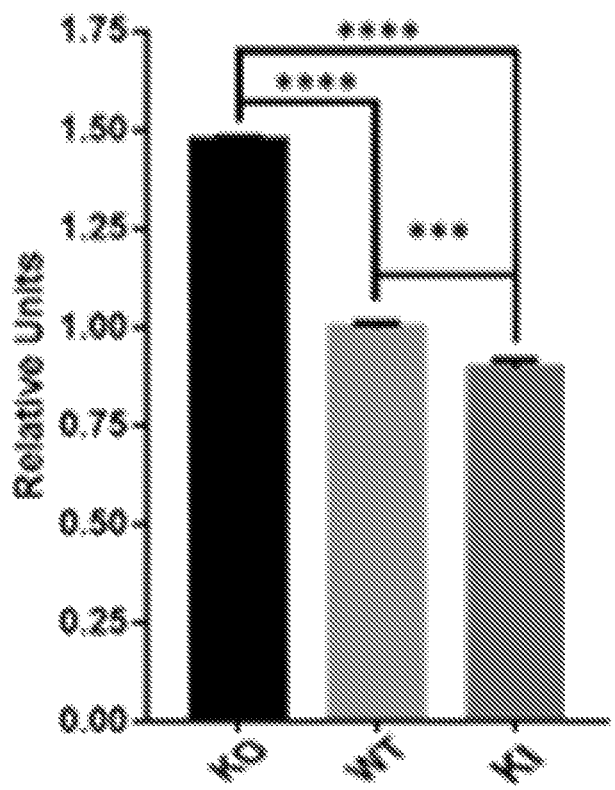
FIG. 7H depicts histogram of basal calcium levels in hippocampal neurons.

FIG. 7H depicts histogram of basal calcium levels in hippocampal neurons; decreasing levels of CRMP2 appears to increase resting calcium levels in neurons.

Figure 7I:
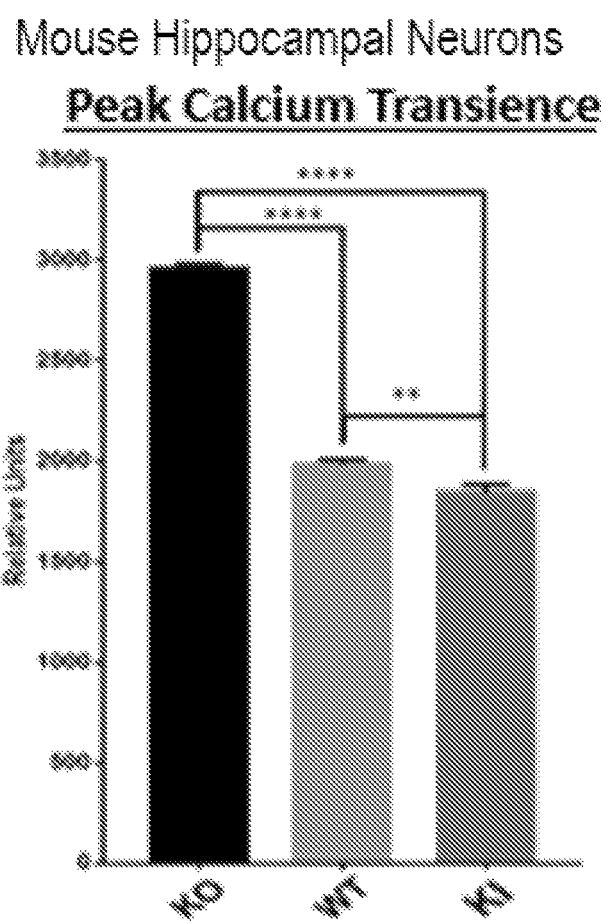
FIG. 7I histogram of peak calcium transience levels during a calcium event in hippocampal neurons.

FIG. 7I histogram of peak calcium transience levels during a calcium event in hippocampal neurons; decreasing levels of CRMP2 appears to increase peak intracellular calcium levels during an event. $N \geq 431$ neurons per group for calcium imaging.

Figure 8A:
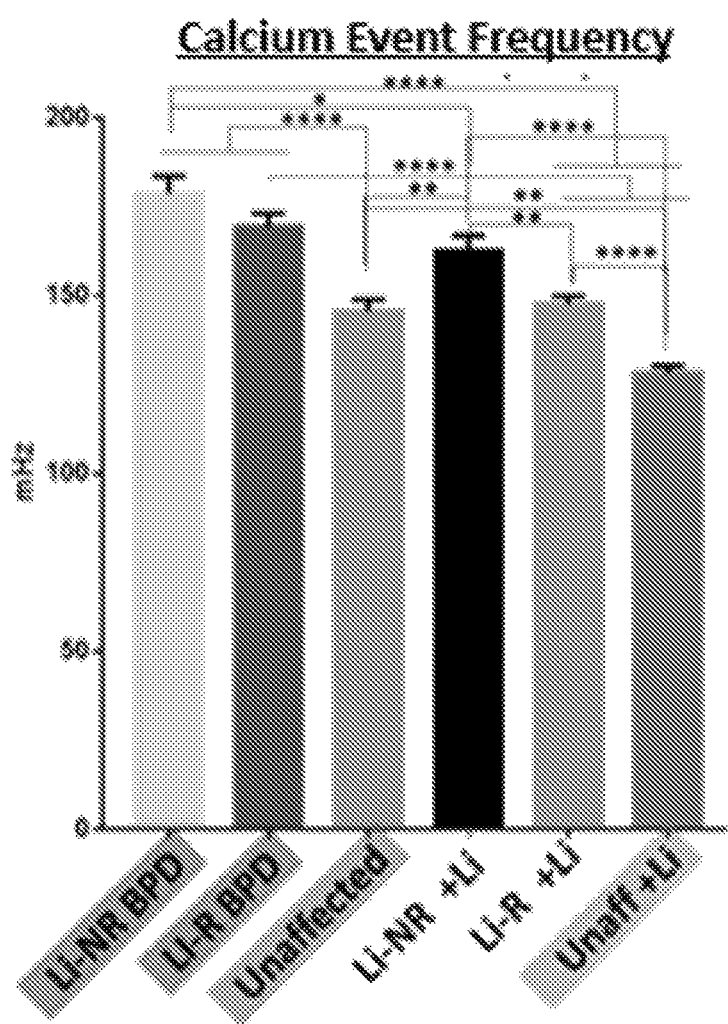
FIG. 8A-8C depict examples of Fluo-4AM calcium imaging.
Figure 8B:
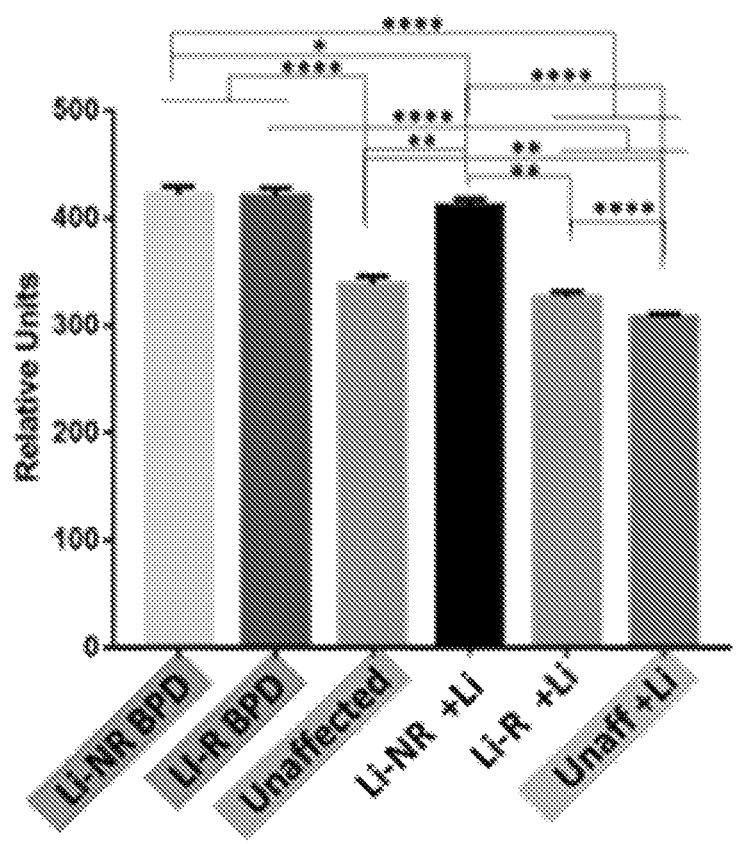
Figure 8C:
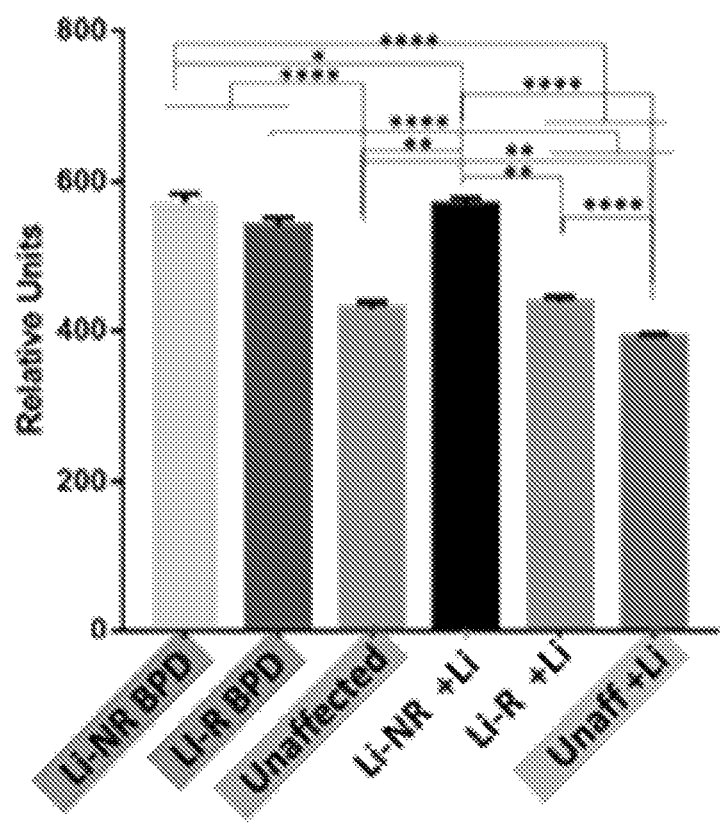

FIG. 8A-8C depict Fluo-4AM calcium imaging that was performed on iPSC derived cortical inter-neuron cultures from lithium nonresponsive BPD (Li-NR BPD) individuals, lithium responsive BPD (Li-R BPD), and unaffected individuals treated with and without 10 mM lithium for 1 week at. As it is postulated CRMP2-KO mice are models for BPD and CRMP-KI mice are analogs for lithium treatment, BPD neurons behavior should mirror CRMP2-KO mice neurons (red), unaffected neurons (blue) mirror WT mice neurons, and unaffected-lithium treated neurons (green) should recapitulate CRMP2-KI mice neurons.

FIG. 8A depicts a histogram of calcium event frequency in human iPSC derived inter-neuron cultures. In some embodiments, decreasing levels of CRMP2 (BPD neurons have decreased CRMP2 activity; lithium treated neurons have increased CRMP2 activity) correlates to increased calcium event frequency.

FIG. 8B depicts a histogram of resting calcium levels in human iPSC derived inter-neuron cultures. In some embodiments, decreasing levels of CRMP2 correlates to increased resting calcium levels in human neurons.

FIG. 8C depicts a histogram of peak calcium transience during an event in human iPSC derived inter-neuron cultures. In some embodiments, decreasing levels of CRMP2 correlates to increased peak calcium transience. One way ANOVA, error bars are SEM, n≤480 neurons analyzed per group (*p≤0.05; p≤0.01; *p≤0.001; ****p≤0.001).

Figure 8D:
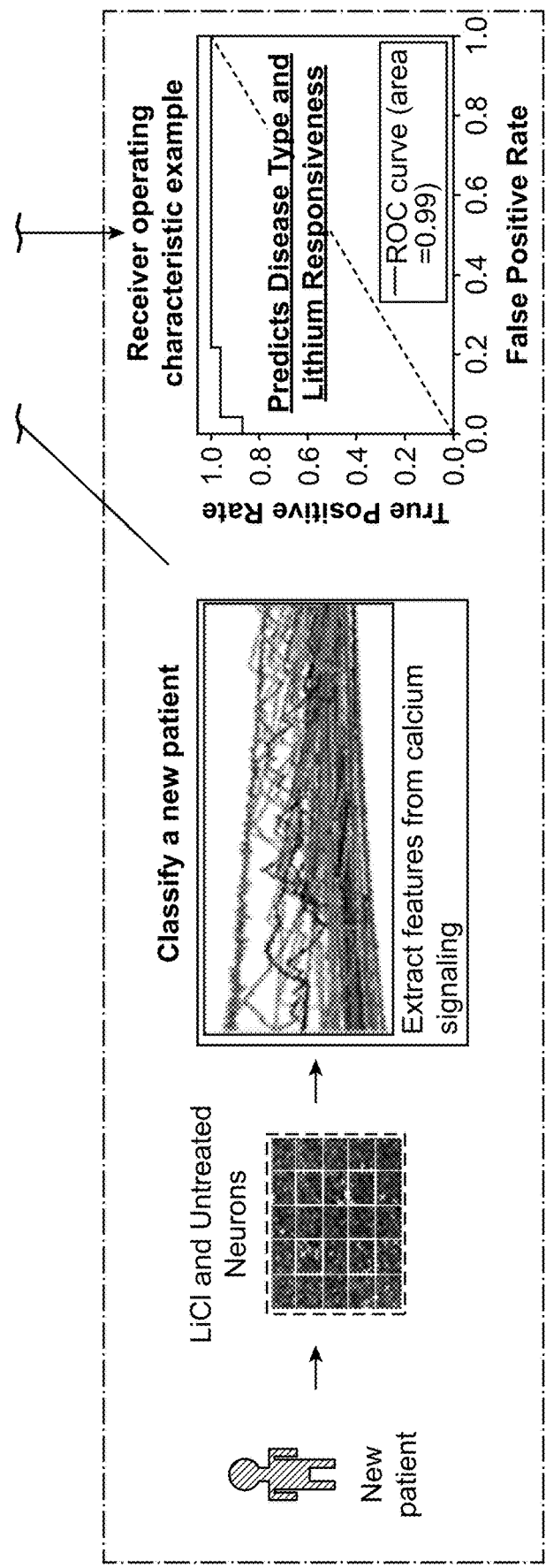
FIG. 8D depicts a histogram of calcium event frequency in human iPSC derived inter-neuron cultures.

FIG. 8D depicts a one verus all "Gradient Boosting" machine learning classifier diagram. In some embodiments, a gradient boosting decision tree was used for sorting because it has a lower affinity for over-fitting, and down sampling was performed to enhance training accuracy. In some embodiments, a receiver operating characteristic for the trained model has an accuracy rate >0.99, the features used for training are calcium event frequency, basal calcium levels, peak calcium transience, and calcium event amplitude.

FIG. 9A depicts an equation for quantifying synchrony within a network of neurons. In some embodiments, the equation quantifies the percentage of neurons in a network have calcium events simultaneously.

Figure 9B:
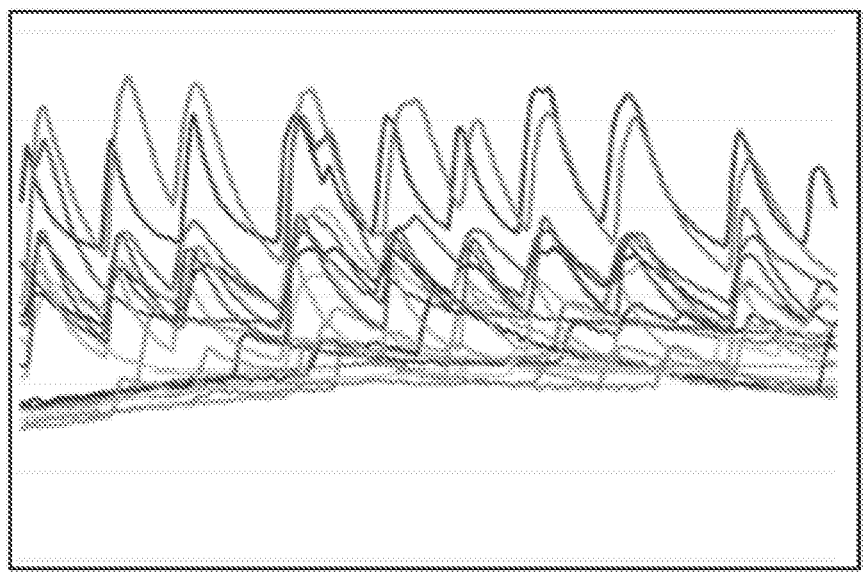
FIG. 9B depicts representative traces of network calcium signaling kinetics from a normal neuronal in vitro culture.
Figure 9C:
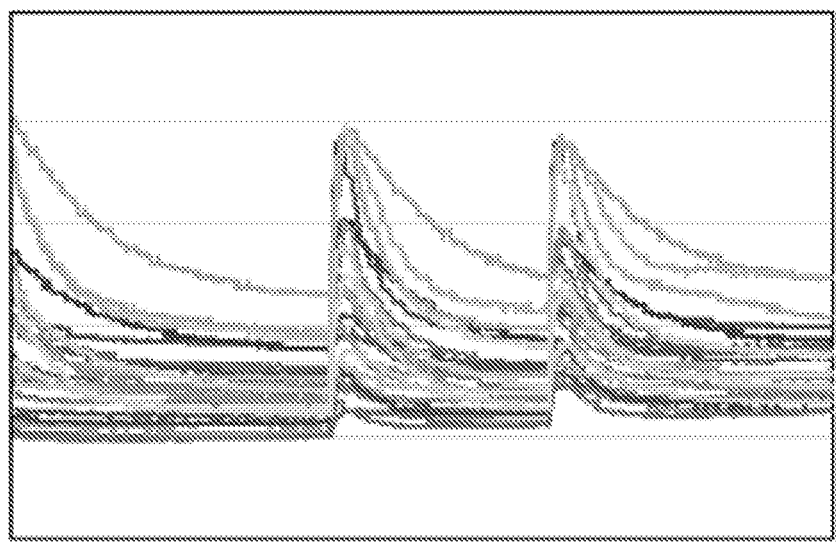
FIG. 9C depicts representative traces of network calcium signaling kinetics from a synchronous neuronal in vitro culture.

FIGS. 9B and 9C depict representative traces of network calcium signaling kinetics from a normal neuronal in vitro culture and a synchronous neuronal in vitro culture, respectively.

Figure 9D:
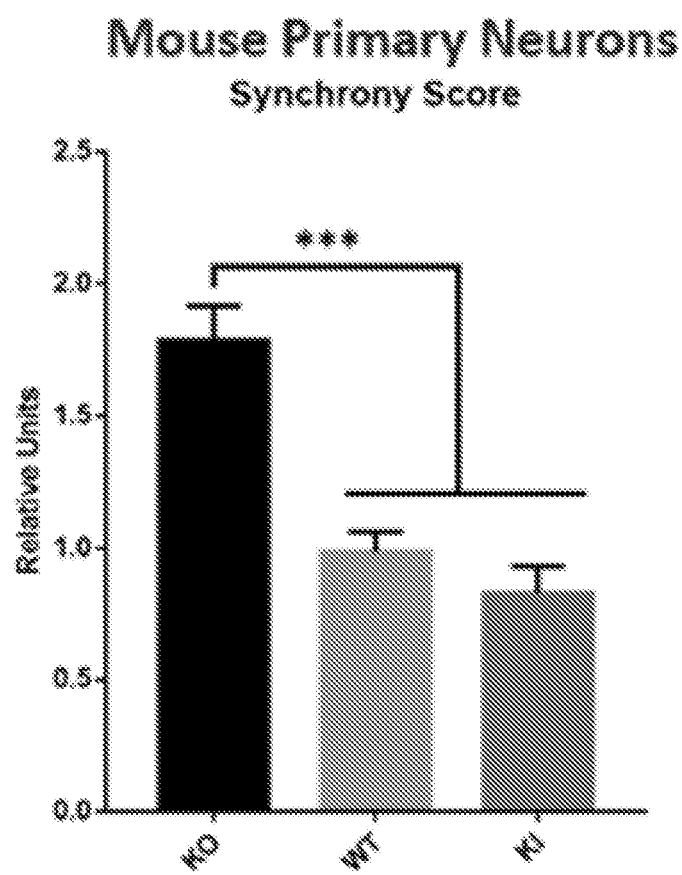
FIG. 9D depicts a histogram of average synchrony scores of primary hippocampal neuronal cultures from CRMP2-KO, WT, and CRMP2-Ki mice.

FIG. 9D depicts a histogram of average synchrony scores of primary hippocampal neuronal cultures from CRMP2-KO, WT, and CRMP2-Ki mice.

Figure 9E:
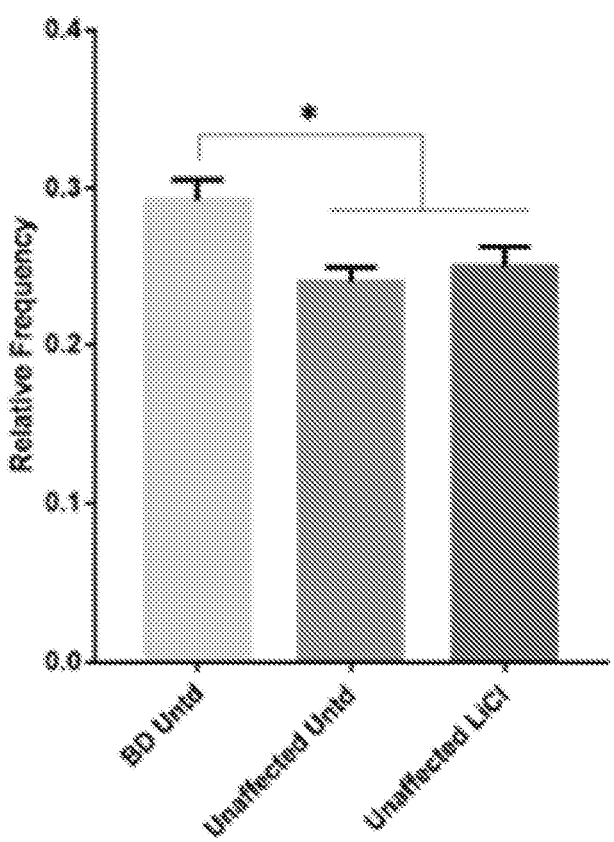
FIG. 9E depicts a Histogram of average synchrony scores of iPSC derived cortical neuron cultures from BPD, unaffected, and lithium treated unaffected human neurons.

FIG. 9E depicts a Histogram of average synchrony scores of iPSC derived cortical neuron cultures from BPD, unaffected, and lithium treated unaffected human neurons.

Figure 10A:
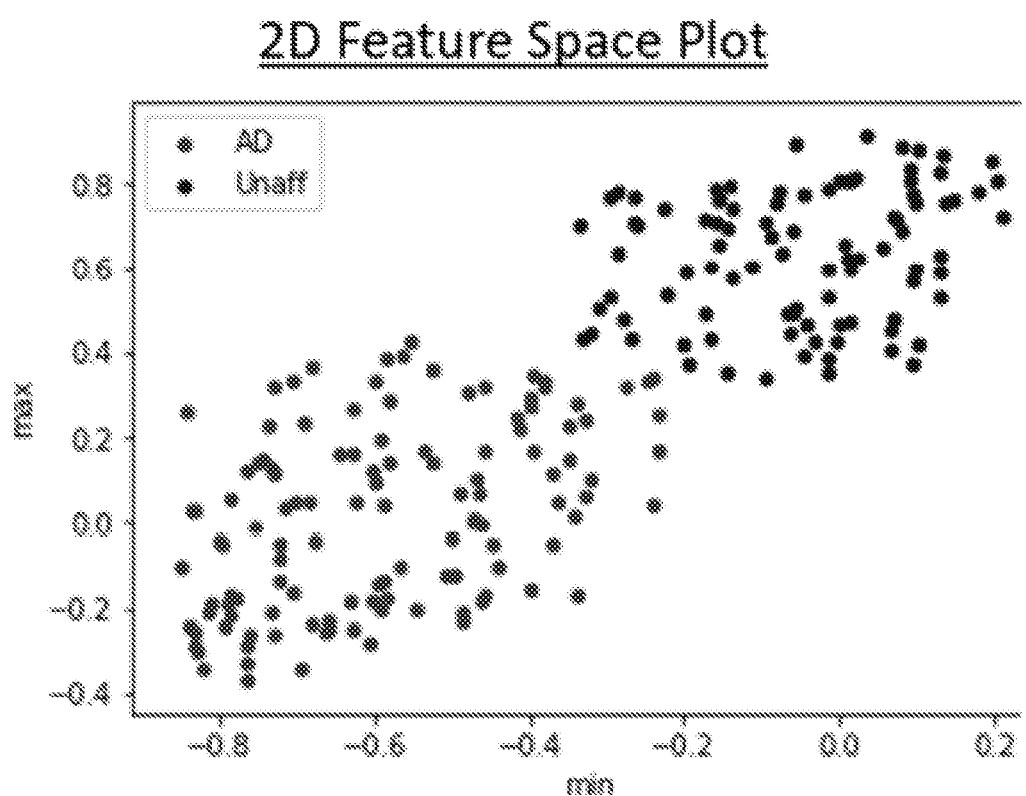
FIGS. 10A-10F depict various plot graphs of data that suggests that Alzheimer's disease and Parkinson's disease are differentiable from unaffected based on calcium dynamics.
Figure 10B:
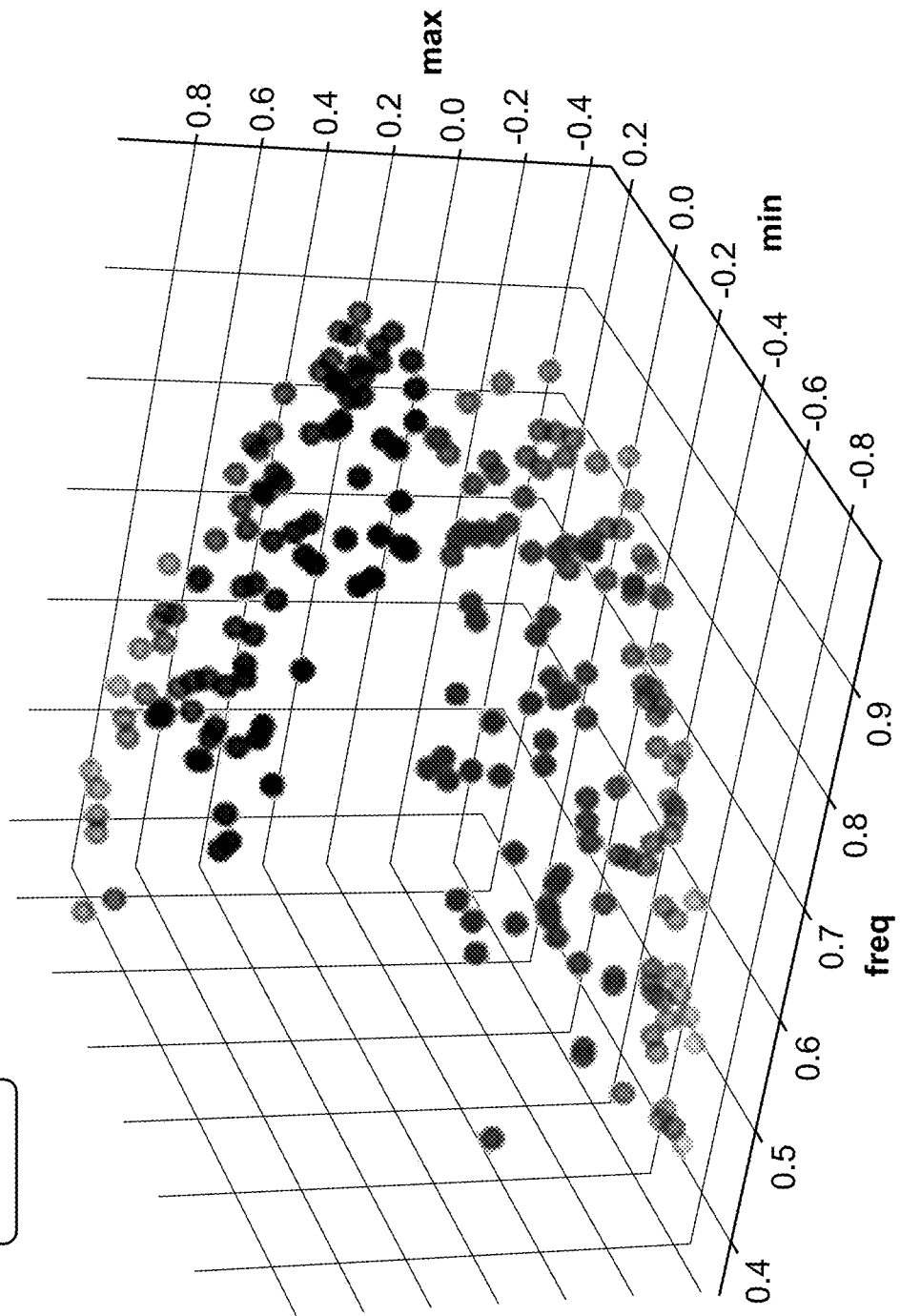
Figure 10C:
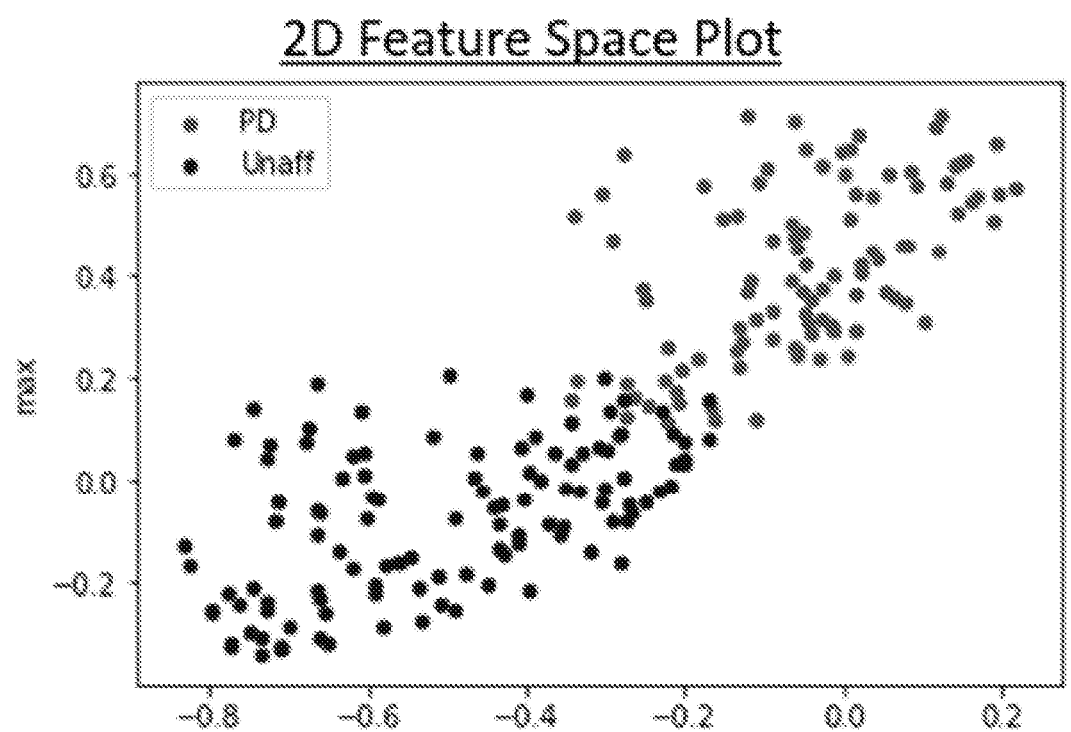
Figure 10D:
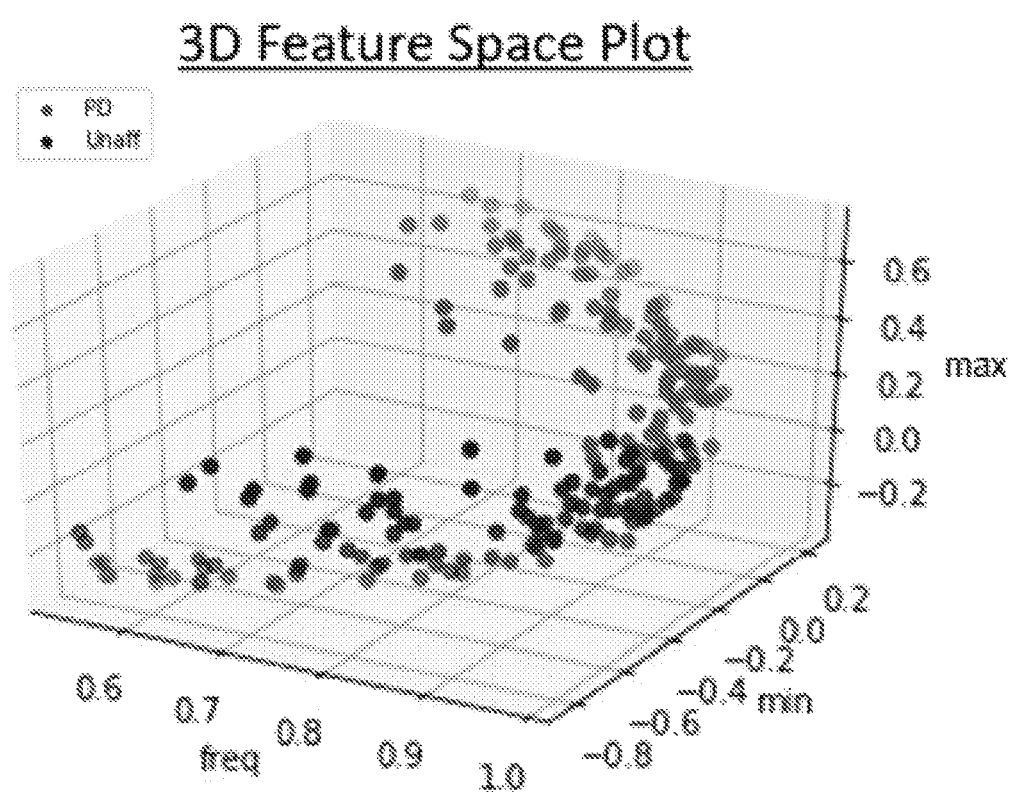
Figure 10E:
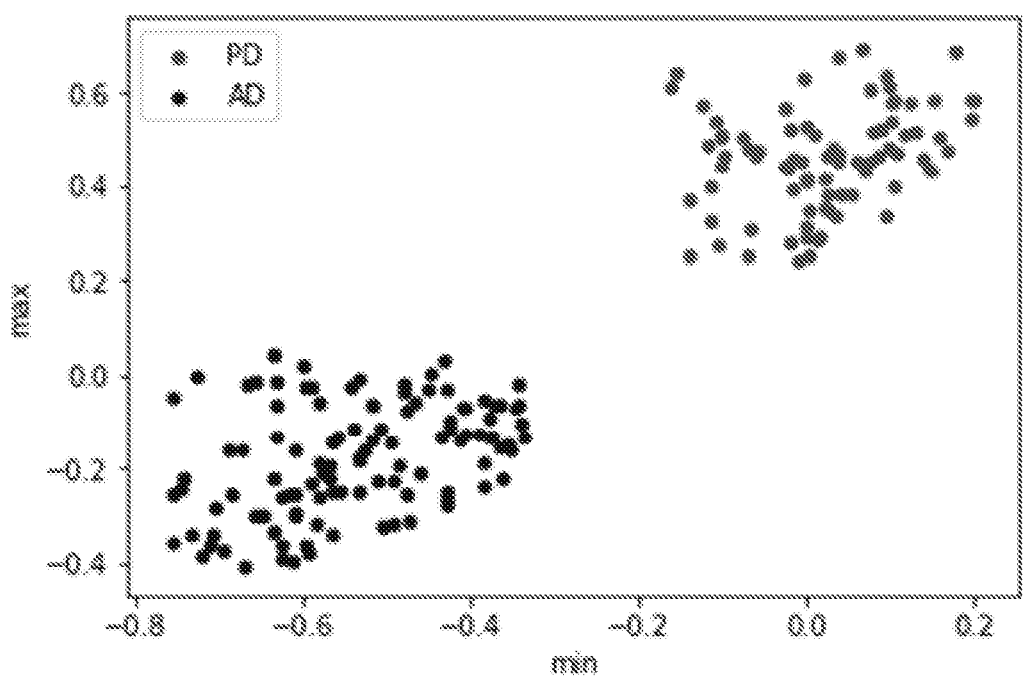
Figure 10F:
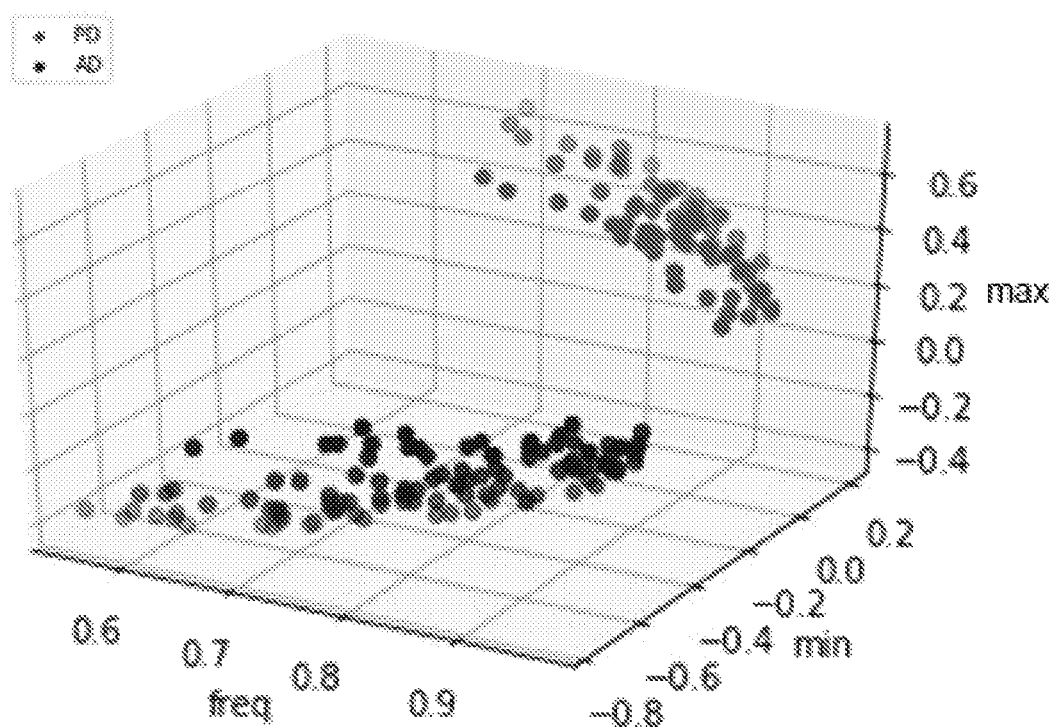

FIGS. 10A-10F depict various plot graphs of data that suggests that Alzheimer's disease (AD) and Parkinson's disease (PD) are differentiable from Unaffected (Unaff) based on Calcium dynamics. FIG. 10A depicts a 2D feature space plot and FIG. 10B depicts a 3D feature space plot of data showing Alzheimer's disease (AD; gray dots) classification with an accuracy of 98 percent and Alzheimer's disease area under the curve of 98 percent. FIG. 10C depicts a 2D feature space plot and FIG. 10D depicts a 3D feature space plot of data showing Parkinson's disease (PD; gray dots) classification with an accuracy of 97.9 percent and Parkinson's disease area under the curve of 97.8 percent. FIG. 10E depicts a 2D feature space plot and FIG. 10F depicts a 3D feature space plot of data from a preliminary run of data through the described classification system where Alzheimer's disease (AD; black dots) and Parkinson's disease (PD; gray dots) are distinguishable based off calcium signaling dynamics. The plots show an accuracy of 99 percent and an area under curve of 99 percent.

Methodology

The development of the described classification system has demonstrated post mortem brains from BPD individuals contain elevated inactive pCRMP2-T514. Moreover, human BPD neurons derived from induced pluripotent stem cells in vitro show similarly elevated pCRMP2-T514 that can be normalized with lithium treatment. Abrogation of CRMP2 activity in mice (CRMP2-KO) emulates a BPD phenotype, particularly the manic phases. And recapitulating the effect of lithium treatment by use of a transgenic mouse obstructing CRMP2-T514 phosphorylation (CRMP2-KI) prevented these manic-like BPD behaviors, the first known genetic intervention to do so.

An explanation from how reduced CRMP2 activity underlies BPD was suggested by alterations in neuronal cytostructures and their function, particularly with neurites, dendritic spines, synapses, axonal transport, and ion channel regulation (Tobe et al., *Probing the lithium-response pathway in hiPSCs implicates the phosphoregulatory set-point for a cytoskeletal modulator in bipolar pathogenesis*, PNAS 114: E4462-E4471 (2017); Yamashita et al., *Regulation of spine development by semaphorin 3A through cyclin-dependent kinase 5 phosphorylation of collapsin response mediator protein 1*, J Neurosci 27:12546-12554 (2007); Uchida et al., *Semaphorin3A signalling is mediated via sequential Cdk5 and GSK3beta phosphorylation of CRMP2: implication of common phosphorylating mechanism underlying axon guidance and Alzheimer's disease*, Genes Cells 10:165-179 (2005)). Coupled with the finding that only the active form of CRMP2 is present in spines and that CRMP2-KO mice have decreased spines density, a hypothesize was formed that CRMP2 activity plays a role in spine function, generation, and or maintenance responsible for neural network formation and function and intersects with BPD pathology.

In one study neurons from transgenic mice lacking CRMP2 or with constitutively active CRMP2 as reliable models for various states of BPD were employed. As a further test, iPSC-derived neurons from BPD individuals versus unaffected control (see FIG. 1). Using neurite proteomics, it was determined that calcium signaling is linked to CRMP2 functionality. Through observing neuronal network dynamics and development of an algorithm for classification of neuronal signaling data, a counterintuitive axis between neuronal calcium hyperactivity and quantifiably hypofunctional neuronal networks was identified. Furthermore, this approach is tractable to augment clinical BPD diagnosis and guide optimal treatment strategies.

To determine the mechanism for how CRMP2 mediates BPD mania, neuronal network signaling in CRMP2-KO primary hippocampal neurons (and genetically paired wild type neurons, WT) with multi-electrode array (MEA) can be observed (see FIG. 2). A basic purpose of a neuronal network, much like circuits in a computer, is to process and share information within itself, with action potential "spikes" acting as bytes of information relayed from one neuron to another. CRMP2-KO neuronal networks, which mimic BPD, demonstrated an impoverished signaling profile compared to wild type controls, although CRMP2-KO neurons create hypofunctional neuronal networks (see FIG. 3). If the purpose of neuronal networks is to share information between neurons, then it would be expected that more functional networks can share more information, with increased complexity, for longer periods of time. CRMP2-KO neurons have less frequent complex signaling events called "burst" compared to WT controls, implying the loss of CRMP2 activity decreases a neuron's ability to communicate with other neurons (see FIG. 4A). When CRMP2-KO neurons do exhibit complex network signaling events, called "network bursts", the duration is shorter than that of WT neurons (see FIG. 4B). CRMP2-KO networks also communicate less information or "spikes" during network signaling events. In summary, absence of CRMP2 activity reduces communication of complex information, and network signaling events contain less information over shorter periods of time (see FIG. 4C). Implementations of the described classification system provide insights into the molecular mechanism for how diminished CRMP2 activity leads to diminished neuronal networks and BPD behavior, as it could provide critical insights into the processes underlying cognitive function.

Isolation of Neurites from Transgenic CRMP2 Mice

Neurons with depleted CRMP2 activity (CRMP2-KO and LiR-BPD) have diminished neurite length and dendritic spine density. Thus, understanding how CRMP2 regulates molecular machinery in these structures, and how they relate to BPD pathology can provide insights. The development of the described classification system demonstrated that E16.5 primary hippocampal neurons from CRMP2-KO mice showed no CRMP2 protein in western blots while CRMP2-KI had levels of CRMP2 similar to that of wild type animals (see FIG. 5A). Furthermore, CRMP2-KI neurons also showed no phosphorylation at CRMP2-T514, which is the residue postulated to be integral to the lithium's mechanism of action for treating LiR-BPD but was found as expected in wild type neurons (see FIG. 5B).

A published method for neurite isolation protocol was employed to examine how CRMP2 activity impacts the proteome of neurites isolated from CRMP2-KO, CRMP2-KI, and WT hippocampal neurons (see FIG. 5C). The neurite proteome of wild type neurons differs from that of whole primary hippocampal neurons via Coomassie stained protein gels (see FIG. 5D). Furthermore, the neurite proteomes were verified to not contain detectable levels of nuclear proteins such as nuclear mitotic assembly protein (NuMA) or the neuron specific nuclear marker FOX3A/NeuN (see FIG. 5E). Although the neurites contained no nuclear proteins, they did contain the two major isoforms of CRMP2, which implies an ability to observe any protein differentially regulated by CRMP2.

Elucidating Neurite Proteomic Differences Due to CRMP2

A large-scale proteomic assay was performed to determine the different proteins and posttranslational modifications (PTMs) regulated by CRMP2 in neurites (see FIG. 5F). A 2-dimensional in gel electrophoresis (2D-DIGE) was performed comparing CRMP2-KI, CRMP2-KO, and WT neurite protein lysates stained with Cy2, Cy3, and Cy5 dyes, respectively. The whole proteomes from each of the three mouse models were separated by protein size and isoelectric point. Proteins that are differentially regulated by CRMP2 activity in neurites were visualized via fluorescence and subsequently identified with mass spectrometry (see FIG. 6A).

Bioinformatic Analysis of Proteins and Pathways Differentially Modulated by CRMP2 in Neurites 59 proteins were found to be differentially regulated by CRMP2 activity via the 2D-DIGE (see FIG. 7). To determine with an unbiased approach which pathways were most significantly regulated by CRMP2 in neurites, the 2D-DIGE results were analyzed with Ingenuity IPA canonical pathway analysis. Of the 22 pathways predicted to be most influenced by CRMP2 activity in neurites, of greatest interest was calcium signaling, as varying hallmarks of calcium signaling aberrations in BPD neurons in vitro have been identified (see FIG. 6B). CRMP2 has been shown to influence neuronal calcium signaling and neurotransmitter release by interacting with many calcium channel proteins, the most well-known being CaV2.2 (59-63). Known pathways regulated by CRMP2, such as axonal guidance signaling, actin cytoskeleton signaling, and semaphoring signaling in neurons, were also identified. These findings act as internal validation of proteomic profiling. Ephrin signaling, actin cytoskeleton signaling and rho signaling were also identified. All of which are pathways associated with synaptic function. Interestingly, these pathways—along with calcium signaling—all contain MAPK as a constituent.

MAPK Activity Regulates BPD Associated Deficits in Neuronal Network Signaling

Figure 6G:
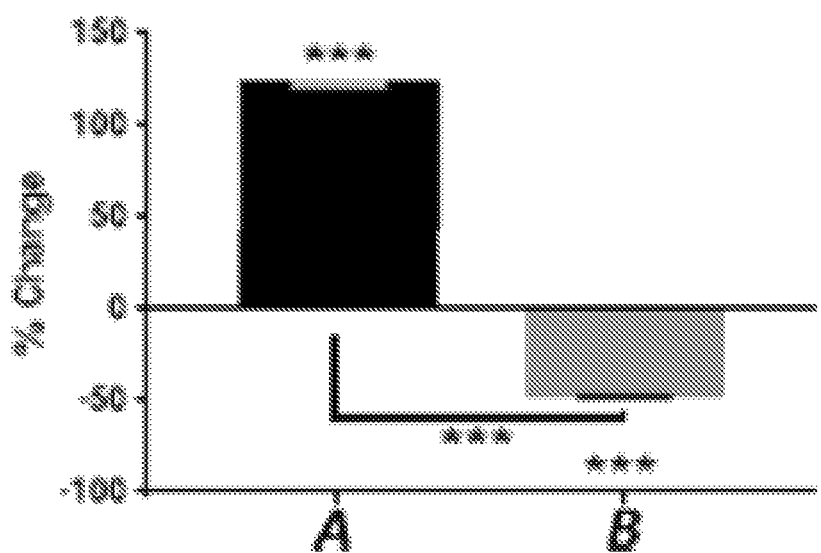
FIG. 6G depicts number of spikes per network burst.

After verifying via western blotting that MAPK level is increased in CRMP2-KI neurites and decreased in CRMP2-KO neurites, the ERK2 isoform at 42 KDa was identified as the most impacted by CRMP2 activity (see FIG. 6C). To test if MAPK/ERK2 signaling is integral to CRMP2's impact on neuronal function, ERK2 signaling was inhibited with the specific inhibitor, Pyrazolyl Pyrrole (PZP), in hiPSC derived neuronal cultures with MEA. A hypothesis that the same MEA signaling deficits observed with the CRMP2-KO neurons would occur in human neurons treated with PZP was formed (see FIG. 6D). Over a three day exposure to PZP, neuronal cultures had an increase in burst frequency, but decreases in network burst durations and number of spikes per network burst (see FIGS. 6E-G). These deficits in MEA neuronal network signaling were the same observed in CRMP2-KO neurons (see FIG. 3). To better determine if the MAPK pathway effect on network signaling is associated with BPD biology, hiPSC derived neuronal cultures was pretreated with 5 mM LiCl for a week before treatment with PZP (see FIG. 6D). Lithium appears to rescue the diminished network signaling caused by MAPK inhibition, as lithium pretreated cultures had increase in network burst duration and number of spikes per network burst (see FIGS. 6F-G). By observing how the neurite proteome is regulated by CRMP2 and by inhibiting MAPK/ERK2 signaling in human neural cultures, and rescue the signaling with the BD therapeutic lithium, the network signaling aberrations observed in CRMP2-KO (a model for BPD) mouse cultures was recreated.

CRMP2 Regulates Calcium Homeostasis and Kinetics in Neurons

CRMP2 plays various roles in calcium signaling in neurons. For example, CRMP2 physically interacts with voltage gated calcium channels and partially regulates the release of the neurotransmitter glutamate, specifically via the channel Cav2.2. Physical interaction of CRMP2 with these calcium channels is also regulated by the calcium regulated protease calpain1. As influxing calcium rushes inside a cell, it causes calpain to undergo a self-activating event, allowing the protease to cleave a wide variety of proteins, including CRMP2, which in turn prevents CRMP2 from physically interacting and regulating calcium channels such as CaV2.2.

Whether these calcium related processes are impacted in the neurites of CRMP2 transgenic mice was investigated. In some embodiments, a linear correlation was observed between CRMP2 activity and the abundance of CaV2.2 in neurites via western blotting, as CRMP2-KI neurites have an increased level of the calcium channel while the CRMP2-KO have a diminished levels compared to WT (FIG. 8A). In some embodiments, that CRMP2-KO neurites were found to have an increased ratio of activated calpain 1. It was hypothesized that this is caused by CRMP2-KO neurons having abnormally high intracellular calcium levels compared to WT controls.

To test whether these changes in calcium-associated proteins in neurites is directly caused by CRMP2 activity, or is a compensatory effect indicative of increased calcium function, in vitro calcium imaging was performed. In some embodiments, Calcium imaging was performed with an IC200 Kinetic Image Cytometer calcium sensitive dye Fluo-4 AM (see FIG. 8D). In some embodiments, the described classification system performs the calcium imaging in a high throughput manner with CRMP2-KO, CRMP2-KI, and WT E16.5 primary hippocampal neurons. In some embodiments, experiments involving transgenic primary hippocampal neurons were compared to WT neurons from littermates. In some embodiments, intracellular calcium level traces were generated in ImageJ, allowing a view of wide variety of calcium kinetic parameters such as, but not limited to, calcium event frequency, resting calcium levels, and peak calcium transience for individual neurons (see FIGS. 8A-C).

In some embodiments, the analysis revealed a clear relationship between CRMP2 activity and the frequency of calcium events in neurons (see FIGS. 8A-C). For example, CRMP2-KO neurons had a higher level of calcium events compared to control (see FIG. 8B). In some embodiments, the CRMP2-KO primary neurons contained the same calcium hyperactivity phenotype as previous reported in human BPD neurons. Furthermore, in some embodiments calcium event frequency appeared to have a linear relationship to CRMP2 activity, as the CRMP2-KI, which emulates lithium-rescued BPD, have decreased levels of calcium events compared to that in controls (see FIG. 8C).

One of the first calcium phenomena ever identified in human BPD cells in 1994 was increased intracellular resting calcium levels, which is a phenotype predicted to exist in the CRMP2-KO neurons based off of the increased levels of activated calpain1 observed. In some embodiments, whether that same phenotype existed in the CRMP2-KO neurons was checked (akin to BPD. In some embodiments, CRMP2-KO neurons were found to also have a higher resting intracellular calcium level than that of controls, while CRMP2-KI neurons have the opposite behavior (see FIG. 8F). As stated earlier, previous in vitro studies have demonstrated that CRMP2 levels can impact calcium signaling and neurotransmitter release via cav2.2, and there is a correlation between elevated peak calcium transience and increased neurotransmitter release. Just as the basal calcium levels, in some embodiments CRMP2-KO hippocampal neurons were found to exhibit higher levels of peak calcium transience, which is associated with increased neurotransmitter release and excitotoxicity, while the CRMP2-KI have a decrease in peak calcium transients which can be associated with less neurotransmitter release (see FIG. 8G).

These findings en masse demonstrate that the CRMP2-KO line have a broad calcium hyperactivity and excitotoxicity phenotype, which has been previously associated in BPD, and that these specific phenotypes have a linear relationship with CRMP2 activity levels, corroborating that the CRMP2-KO mice not only mirror BPD behaviorally, but molecularly and electrophysiologically as well. Conversely, the CRMP2-KI mutation that rescues BPD behavior analogous to lithium treatment, has the opposite phenotype than that of the CRMP2-KO, and can be used as a model for rescued BPD behavior.

Calcium Kinetics of Various Human BPD States are Distinct and Mirror Transgenic CRMP2 Neurons To verify that the calcium kinetic phenotypes, the transgenic mouse neurons was observers as indicative of BPD biology. In some embodiments, an in vitro cortical interneuron cultures was generated from human patients with Li-BPD, LiNR-BPD, and healthy controls. In some embodiments, a differentiation process that generates mature cultures for calcium kinetic analysis was performed. In some embodiments, derived neurons expressed Map2 (mature neuron cytoskeletal element), Cux1 (upper cortical marker), and the ion channel vGlut. In some embodiments, calcium kinetic analysis was performed (as described above with the mice neurons) with human iPSC derived neural cultures from Li-BPD, Li-NR BPD, healthy unaffected controls treated with and without lithium (5 mM for 7 days). It was hypothesized that BPD neurons would have similar phenotypes as that of the CRMP2-KO cultures, while the CRMP2-KI mouse neurons would have the similar calcium kinetic profile of unaffected lithium-treated neurons, and the unaffected neurons would mirror WT mice neurons (FIG. 1).

As hypothesized, in some embodiments, all of the calcium kinetics behaviors detected in the mouse neurons were observed in the human analog, where the BPD neurons had the same increase in calcium signaling as measured by calcium event frequency over that of unaffected controls, while the unaffected lithium treated cultures had the lowest rate of calcium event frequency, which suggests there is a directional relationship between CRMP2 activity and calcium signaling in human neurobiology, just as shown in the transgenic CRMP2 mice (FIG. 9A). Furthermore, in some embodiments the resting calcium levels in the human cultures match that of the mouse neurons, where BPD neurons have elevated basal intracellular calcium levels compared to controls, while the lithium treated unaffected neurons had the lowest resting calcium levels, matching that of the CRMP2-KI neurons (FIG. 9B). In some embodiments, the same directional relationship is observed with peak calcium transience levels in the human derived neural cultures, with BPD neurons exhibiting elevated peak calcium transience levels while the lithium treated unaffected neurons had the lowest levels (FIG. 9C). This indicates that human BPD neurons not only have an increased calcium activity phenotype, but also an aberrant intracellular calcium homeostasis phenotype, where the calcium kinetics are indicative of excitotoxic tendencies.

Unexpectedly and notably, in some embodiments, these same calcium kinetic parameters that were analyzed in the mouse were able to distinguish between the two separate clinical subgroups of BPD (Li-R vs Li-NR), specifically for each parameter of calcium event frequency, resting calcium levels and peak calcium transience, the aberrant levels seen in the Li-BPD individuals were normalized to that of healthy levels when treated with lithium, while the elevated levels seen in the Li-NR BPD levels were never reduced to that of unaffected levels with lithium exposure, and maintained a statistically significant increase over controls (FIGS. 9A-9C). In some embodiments, lithium treatment had no statistical effect on resting calcium levels and peak calcium transience in the Li-NR BPD cultures (FIGS. 9B-9C). So, while Li-R and Li-NR BPD phenocopy one another in elevated calcium kinetics, their response to lithium treatment demonstrates their molecular pathogenesis are distinct.

Predicting BPD and Lithium Responsiveness According to Calcium Kinetics

In some embodiments, the results indicated that Li-NR BPD, Li-R BPD, and unaffected neurons have distinct calcium signaling features. BPD and lithium responsiveness prediction from the findings was tested. In some embodiments, a KNN machine learning classifier with basal calcium levels, peak calcium transience, and calcium event frequency as the training features was developed. In some embodiments, a KNN approach was used because correlation analysis showed the features were not independent, and a k-nearest neighbor value of 5 to prevent over fitting. To optimize the accuracy of the model, in some embodiments down sampling was utilized during training (n=10). After training, the model had a ROC of 0.996, meaning a false positive rate below 1%, with a validation accuracy rate of 99.7% (FIG. 9D). In some embodiments, if the model predicted BPD, it would next determine if they were Li-R or Li-NR, with 98.5% accuracy and a false positive rate below 1% (ROC=0.993) at a down sample size of 10 neurons. In some embodiments, the model can highly accurately diagnose if a patient has BPD, and if so, will they respond to lithium with only 20 neurons (10 untreated neurons and 10 lithium treated neurons). In some embodiments, the classifier was designed to have clinical relevance by separating data points by cell line, and training the classifier with 80% of the data. In some embodiments, when predicting, the model pulled LiCl treated and untreated data points from the remaining 20% of unseen data. In some embodiments, the data for training and predicting were chosen randomly from the calcium recordings being classified, and this procedure was repeated randomly 2000 times to get a statistical estimate of the accuracy and false positive rates.

BPD and CRMP2-KO Neurons Share Aberrant Neuronal Network Calcium Signaling Synchrony In some embodiments, the MEA data demonstrating that action potential signaling, which is predominantly driven by sodium and potassium channels, is impacted by CRMP2 activity with regards to network signaling. One of the main calcium signaling characteristics that has been associated clinically with BPD is epilepsy. Epilepsy and seizures are one of the major comorbidities associated with BPD and there is a strong epidemiological history relating the two conditions. A main off-target therapeutic prescribed to BPD patients and other psychiatric patients to deal with anxiety is valproic acid which is the quintessential anti-epileptic drug. In some embodiments, the calcium kinetics data with a focus on calcium network signaling was interrogated to measure network health. To quantify this, in some embodiments, an algorithm to quantify calcium events synchrony in vitro, which is indicative of an in vitro epileptic phenotype, was developed. In some embodiments, the algorithm takes into account all neurons in a network and their calcium events, assigns individual calcium events into time bins, performs a summation calculation for each time bin, and then provides a synchrony score based off the highest bin value normalized to the number of neurons in the network (FIG. 10A).

In cultures from WT mouse hippocampal neurons, neuronal networks that had stochastic and predominantly randomized calcium signaling where there seemed to be no discernable pattern of calcium events but contained small groups of neurons that were synchronized (but no pattern that held true to the entire culture) were employed. While in the CRMP2-KO primary neuronal cultures 100% synchrony of calcium events over time where every neuron had a calcium event at the same moment in time was often observed (FIGS. 10B and 10C). This observable difference was quantified and found that the CRMP2-KO primary cultures had a statistically increased level of calcium synchrony compared to that of wild type and CRMP2-KI. While the CRMP2-KI cultures were not statistically significantly lower than that of the wild type cultures, it appears that CRMP2 activity, and the lack thereof in the CRMP2-KO neurons, has an impact on calcium network dynamics (FIG. 10D). To verify if this phenomenon held true in human BPD biology, a calcium synchrony in BPD neurons, healthy unaffected neurons, and unaffected neurons treated with lithium was quantified. In some embodiments, those groups most accurately correspond to CRMP2-KO, WT, and CRMP2-KI neurons respectively. In some embodiments, the same directional increase in synchrony score in the BPD neurons as is seen in the CRMP2-KO neurons, where the BPD neurons have elevated levels of calcium synchrony in their networks over that of unaffected neurons and unaffected neurons treated with lithium was observed (FIG. 10E). In some embodiments, although the level of increased synchrony is not as high as that of CRMP2-KO neurons, the synchrony phenotype caused by diminished CRMP2 activity is still present in the human BPD biology.

In some embodiments, in combination with the earlier MEA data, this calcium network analysis provides a holistic picture of how the calcium hyperactivity observed in the CRMP2-KO and BPD neurons translates to hypofunctional networks, where less information is being relayed and the health of the neuronal network signaling is indicative of an epileptic disease state. A biological analogy for conveying how this increase in neural activity has negative health impacts is tachycardia in heart health, where an abnormally high heart rate can lead to less overall cardiac output, thus providing a deficit to the patient.

Discussion

BPD has historically been an intractable disease with little known regarding its pathophysiology and with few clinical breakthroughs in recent decades, just as with many other polygenic neurological disorders such schizophrenia (SCZ) and autism spectrum disorders (ASD). An independent group generated a brain specific CRMP2-KO mouse and observed a variety of behavioral and cognitive phenotypes reminiscent of SCZ, further corroborating the finding that CRMP2 plays a powerful role in multiple neurocognitive function. Moreover, the inactive pCRMP2-T514:active CRMP2 ratio is uniquely elevated in LiR BPD patients, and lithium normalizes this ratio to the levels observed in unaffected individuals. This is consistent with post mortem BPD brain tissue studies that reported shorter neurites and a lower dendritic spine density in BPD individuals, both phenomena that would be expected due to prolonged loss of CRMP2 activity. This suggests that the molecular lithium-response pathway in BPD acts through CRMP2 to alter neuronal cytoskeletal dynamics, most particularly dendrite and dendritic spine formation, and therefore neural network development and function.

In some embodiments, a combination of transgenic mice models, "disease in a dish" hiPSC modelling, and patient data from the clinic demonstrate BPD is a network'opathy driven by imbalanced regulation of the neuronal cytoskeletal modulator CRMP2. By unbiasedly elucidating the proteins and pathways impacted by CRMP2 activity in neurites, a previously unexplored cellular structure with regards to BPD molecular pathogenesis, inter-neuronal communication, calcium signaling in particular, is dysregulated due to loss of CRMP2 activity. A possible explanation for how decreased CRMP2 activity in spines coalesces into behavioral and cognitive dysfunction is through CRMP2's role in calcium signaling. As such, there is a counterintuitive juxtaposition between how neuronal hyperactivity across models of BPD leads to hypofunctional neuronal networks. In neurons with decreased CRMP2 activity, from LiR BPD patients to the CRMP2-KO mouse, there is a profile of electrophysiological characteristics that paint a picture of hyperexcitability. An increase in calcium event frequency was observed in both mouse and human neurons with known CRMP2 deficiencies. In some embodiments, CRMP2 has been shown to influence neuronal calcium signaling and neurotransmitter release by interacting with many calcium channel proteins, the most studied being CaV2.2. On a more practical note, these data provide robust evidence that the transgenic CRMP2 mice can be utilized as highly faithful animal models for lithium responsive BPD, as both their behavior, proteomics, neuronal structure and signaling profiles recapitulate observations in human BPD.

The specific calcium analysis parameters can also differentiate between the clinical subgroups of BPD and could immediately be developed as a diagnostic tool for all neurological disorders when paired with a personalized medicine approach. A previous report has suggested patch clamping as a method for BPD diagnosis, but diagnosis via patch clamping lacks feasibility in the clinic do to slow and laborious nature of the technique. High throughput calcium imaging for diagnosing and predicting drug responsiveness has tremendous promise clinically. The possibility exists for patients at any age to give blood samples that can produce neural cultures with defined protocols, then subsequently have their calcium kinetics screened in a high throughput manner, to not only reach a possible diagnosis, but to identify the most efficacious therapeutics for their neurobiology. A small, but not insignificant aspect of diagnosing, is how the neuropsychiatric field historically views BPD. BPD is still categorized in the DSM-V as a mood disorder, like depression, but this label is based off phenotypical characteristics versus similar biology. In some embodiments, the described classification system, provide a novel molecular basis for classifying BPD.

Materials and Methods
Primary Tissue and Cell Isolation

In some embodiments, primary hippocampal and cortex tissue was isolated from E16 mice embryos and placed in 100 mm dish containing Hanks medium on ice. Cortex tissue was frozen in liquid nitrogen for later use in western blot or co-immunoprecipitation assays. Hippocampal tissue was washed once with HBSS and was transferred to conical containing fresh EBSS at room temperature. Hippocampal tissue was disassociated using titration with fire polished glass pipette until no cell conglomerates were visible. Cells were the counted and plated at target density accordingly. Every experiment requiring primary neurons from CRMP2-KO or CRMP2-KI mice, always had wild type neurons isolated from a genetically paired litter mate. Primary neural cultures were grown at 37 C at 7% CO2.

Human Induced Pluripotent Stem Cells Culturing and Differentiation

In some embodiments, hiPSCs were cultured in mouse embryonic fibroblast conditioned medium (MEF-CM) with 20 ng/μl recombinant human basic Fibroblast Growth Factor (bFGF) (Research and Development (R&D) Systems, 233-FB), as other defined medias contained lithium which could skew future results. Other hiPSCs were cultured in defined mTeSR1 medium (Stem Cell Technologies) with indistinguishable results. Stem cells were mechanically passaged every 5-7 days using 1 ml serological pipettes (Falcon), and grown at 37 C. hiPSCs were differentiated to cortical intern neurons in a step wise fashion as previously reported, but briefly: hiPSCs were differentiated by changing medium to a neural Induction medium (DMEM/F12+Glutamax (Life Tech, 10565-018) N2, B27 (Gibco, 17502-048; 17504-044), 5 mg/ml BSA (Sigma, A1933-5G), Pen/Strep (Life Technology, PS-20) three days after passaging or when cells were 30-40% confluent. Medium was changed and supplemented daily with small molecules as described: 3 μM CHIR99021 (Stemgent, 04-0004) 2 μM SB431542 (Stemgent, 04-0010), μM Compound-E (Millipore, 565790-500UG) with 10 ng/ml hLIF (Millipore, LIF1010) for 7 days. hNSCs were switched to Differentiation Medium (Neurobasal Medium (Life Technology, 21103049), B27, Glutamax (Gibco, 35050061), Pen/Strep (Life Technology, PS-20). On day 8, adherent cells were scraped using a 10 ul tip to obtain small sections. The medium was supplemented with ROCK Inhibitor (Tocris, 1254). Cells were then cultured on ultra-low attachment plates (Corning, 3471) to create floating neurospheres which were cultured for 10 days in Differentiation Medium. Medium was changed every other day and spheres were agitated with each medium change to prevent aggregation. After 10 days incubation, aggregates were separated with accutase (Millipore, SCR0005) for 16-20 minutes at 37° C. with agitation, counted and plated on Matrigel coated plates density 50,000-60,000 cells/cm$^2$. Cells were cultured the following 10 days (with medium changed every other day) in Differentiation Medium supplemented with 20 ng/ml BDNF (R&D, 248BD), 20 ng/ml GDNF (R&D, 212-GD), 10 μM DAPT (Cayman Chemicals, 13197), 0.2M L-Ascorbic Acid (Sigma, A4403), 1 ng/ml TGF3Beta (R&D, 243-B3-002) and 0.5 mM dbCAMP (Sigma, D0627). Over 90% of the hiPSCs become TUJ1+ cells, virtually all of which become MAP2+; of those, most of these cells co-expressed CUX1, a marker for upper cortical neurons, as previously described (26). Neurons were cultured for a least an additional 12 weeks before calcium imaging. A subset of neurons were treated with 5 mM LiCl for 7 days in Differentiation media before calcium imaging.

Immunohistochemistry

In some embodiments, adherent cells were washed in PBS, fixed with 4% paraformaldehyde (PF) in PBS (Wako, 163-20145) for 20 minutes, washed with PBS and blocked in 3% BSA, 3% donkey serum (Jackson Immuno, 017-000-121), and 0.1% Triton-X (Sigma, T9284-100 ml) in PBS for 1 hour or overnight at 4° C. Cells were then incubated with primary antibody for 2 hours or overnight at 4° C. at a concentration of 1:100 in PBS with 5% donkey serum (Jackson Immuno, 017-000-121) and 0.3% Triton X (Sigma, T9284-100 ml).

Calcium Imaging

In some embodiments, plates were coated with Poly-Ornithine (10 μg/mL) overnight followed by laminin (5 μg/mL) overnight. Primary hippocampal cells (E16) were plated (20,000 cells/well) on black edge 96 well, clear bottom plate (Greiner Bio-One 655090). Cells were maintained for 17 days before being at Vala Biosciences, La Jolla, CA A 5 mM stock solution of Fluo-4 AM (Life Technologies, F14201) was prepared by dissolving the calcium indicator in a 20% w/v solution of Pluronic F-127 (Life Technologies, P3000) in DMSO. A dye cocktail of 0.2 μg/mL Hoechst 33342 (Life Technologies, H3570), and 1:4 Fluo-4 AM stock in Tyrode's solution with sodium bicarbonate (Sigma-Aldrich, T2397) was added to each well. Cells were then incubated for 20 min in a 37° C. incubator. The cells were then washed twice in Tyrode's solution. After the second wash, Tyrode's buffer was added to each well, and the cells were incubated once more for 20 min at 37° C./5% CO2 prior to imaging. Wells were then imaged on the IC200 Kinetic Image Cytometer (Vala Sciences, Inc.) for 30 s producing 900 images.

In some embodiments, calcium imaging data was analyzed and quantified in ImageJ by a blinded observer. Neurons were only observed from the same four regions of interest for every well, to control for any confounds that could arise from spatial differences between wells and replicates. Individual neurons that fired and resolved at least once within a 30 s period were identified. Calcium frequency was calculated by counting the number of events for individual neurons identified by a blinded observer and divided by 30 seconds. Resting calcium values are based off minimum calcium levels for an individual neuron minus the background signal from the culture dish. Peak calcium transience levels are based off maximum calcium levels for an individual neuron minus the background signal from the culture dish. Due to the use of Fluo-4-AM as the calcium indicator, these levels are relative and not specific to a known intracellular calcium concentration. Amplitudes were taken using the delta from minimum to maximum values for each neuron.

In some embodiments, synchrony scores were derived using an algorithm developed in this study. Intensity datasets were transformed into a 500 ms moving average to reduce false peaks. Peaks were identified if intensity readouts 33 mss before or after were smaller at any given time point. The 5-point time span filtered out artificial peaks produced by noise. Peaks for each neuron were then filtered, counting only those that were at least above 50% of the amplitude of the largest calcium event. Peaks across a culture were binned in time frames of 800 ms, only cultures with network behavior, the ability to have a at least 20 active neurons, were used to quantify a synchrony score. Synchrony scores were assigned by taking the bin with the highest peak count within a culture of neurons, divided by the total number of neurons in the network.

Multi Electrode Array

In some embodiments, 12-well MEA plates (Axion Biosystems, M768-GL1-30Pt200) were coated with Poly-Ornithine (10 µg/mL) overnight followed by Laminin (5 µg/mL) overnight. Cell solution of 120,000 cells in 50 µL droplet were placed directly in the center area containing the electrodes, 3 wells per cell line. Plates were incubated at 37° C. for 2 hours to allow adhesion followed by application of 1.5 mL fresh media. Plates were maintained and measured after 17 days. MEA measurement was made was using Axion Axis software v.2.3.4 for 10 minutes using neural-real-time-spontaneous configuration, spike threshold was set to 6 standard deviations. Data analysis was performed using Neural Metrics Tool software v2.2 and Neural Axis Plotting Tool v1.1.1.

Neurite Isolation

In some embodiments, primary hippocampal cells were plated (500,000 cells/well) on trans-well inserts, 3.0 µm-pour polycarbonate membrane (Corning, 3414). The underside of the inserts were coated with laminin (5 µg/mL overnight), to chemoattract outgrowing neurites through the pours to physically separate from somas (64). Cells were maintained for 17 days before neurite isolation. Inserts were rinsed once with PBS. A thio-based lysis buffer (provided by Applied Biomics) was used to lyse the neurites, and flash frozen with liquid nitrogen and stored at −80 C. Neurite lysates were also prepped for western blot using with RIPA buffer (Thermo, 89901) and protease and phosphatase inhibitor cocktail ("Halt"; Thermo Scientific Cat, 1861280).

Neurite Proteomics

In some embodiments, protein lysate were stored at −80 C before sending to Applied Biomics on dry ice for 2D-DIGE proteomics analysis. Protein lysate were stored at −80 C before sending to Applied Biomics on dry ice for proteomics analysis. CyDye labeled 2D-DIGE sample gel required 30 ug of protein lysate per group. 1.0 ul of diluted Cy2, Cy3, or Cy5 was added (1:5 diluted with DMF from 1 nmol/ul stock) to wild type, CRMP2-KI and CRMP2-KO lysates respectively, followed by vortex, and then 4 C in the dark for 30 min. 1.0 ul of 10 mM Lysine was added to each of the samples, vortexed and kept under dark on ice for additional 15 min. Cy2, Cy3 and Cy5 labeled samples were mixed and 2×2-D Sample buffer (8 M urea, 4% CHAPS, 20 mg/ml DTT, 2% pharmalytes and trace amount of bromophenol blue) was added, and 100 ul of destreak solution and Rehydration buffer (7 M urea, 2 M thiourea, 4% CHAPS, 20 mg/ml DTT, 1% pharmalytes and trace amount of bromophenol blue) to 250 ul afterwards. The combined solution was mixed well and spun before loading to isoelectric focusing strip (IEF) strip holder.

In some embodiments, after loading the labeled samples onto the pH 3-10 strip holder, 1 ml of mineral oil was added on top of strip. Following the protocol provided (Amersham BioSciences), the IEF was run under dark at 20 C. Upon finishing the IEF, the IPG strips were incubated in the fresh made equilibration buffer 1 (50 mM Tris-HCl, pH 8.8, containing 6 M urea, 30% glycerol, 2% SDS, trace amount of bromophenol blue and 10 mg/ml DTT) for 15 minutes with slow shaking. Then the strips were rinsed in the fresh made equilibration buffer 2 (50 mM Tris-HCl, pH 8.8, containing 6 M urea, 30% glycerol, 2% SDS, trace amount of bromophenol blue and 45 mg/ml Iodoacetamide) for 10 minutes with slow shaking. The IPG strips were then rinsed once in the SDS-gel running buffer before transferred into the SDS-Gel (12% SDS-gel prepared using low florescent glass plates) and sealed with 0.5% (w/v) agarose solution (in SDS-gel running buffer). The SDS-gels were run at 15 C and stopped until the dye front running out of the gels.

In some embodiments, image scans were carried out immediately following the SDS-PAGE using the Typhoon TRIO (GE Healthcare) protocols. The scanned images were then analyzed by Image QuantTL software (GE-Healthcare), and then subjected to in-gel analysis and cross-gel analysis using DeCyder software version 6.5 (GE-Healthcare). The ratio change of the protein differential levels was obtained from in-gel DeCyder software analysis. An additional 300 µg of unlabeled protein was run in a prep gel parallel with the labeled samples gel (described above) to provide sufficient quantities of protein species for identification via mass spectrometry as described below.

In some embodiments, the spots of interest were picked up from the prep-gel based on the in-gel analysis and spot picking design by DeCyder software. The gel spots were washed a few times, and digested in-gel with modified porcine trypsin protease. The digested tryptic peptides were desalted by Zip-tip C18 (Millipore). Peptides were eluted from the Zip-tip with 0.5 ul of matrix solution (cyano-4-hydroxycinnamic acid, 5 mg/ml in 50% acetonitrile, 0.1% trifluoroacetic acid, 25 mM ammonium bicarbonate) and spotted on the MALDI plate.

In some embodiments, MALDI-TOF mass spectrometry (MS) and TOF/TOF (tandem MS/MS) were performed on a 5800 mass spectrometer (AB Sciex). MALDI-TOF mass spectra were acquired in reflectron positive ion mode, averaging 2000 laser shots per spectrum. TOF/TOF tandem MS fragmentation spectra were acquired for each sample, averaging 2000 laser shots per fragmentation spectrum on each of the 10 most abundant ions present in each sample (excluding trypsin autolytic peptides and other known background ions).

In some embodiments, both the resulting peptide mass and the associated fragmentation spectra were submitted to GPS Explorer version 3.5 equipped with MASCOT search engine (Matrix science) to search the database of National Center for Biotechnology Information non-redundant (NCBInr) or Swiss Protein database. Searches were performed without constraining protein molecular weight or isoelectric point, with variable carbamidomethylation of cysteine and oxidation of methionine residues, and with one missed cleavage allowed in the search parameters. Candidates with either protein score C.I. % or Ion C.I. % greater than 95 were considered significant.

Western Blotting

In some embodiments, after thaw from −80 C, the protein lysates were subjected to sonicate on ice, then followed by keeping the tubes on the shaker for 30 minutes at room temperature. Protein concentration assay was carried out using Bio-Rad BCA protein assay method. 25 µl of 4×LDS loading dye (Life Tech, NP0007) and 10 µl of DTT (Acros, 32719) are added to 65 ul of sample. Typically 6-10 ug of protein were loaded per well of a 4-12% NuPage gradient gel (Life Tech, NP0322BOX). Gels were run at 160V for 70 minutes and transferred at 30V for 80 minutes using the NuPage Western Blotting system by Life Technologies (Running Buffer: NP0002; Transfer Buffer: NP0006-01). Blots were blocked in TBS (Tirzma Acid (Sigma, T3253) plus Trizma base (Fisher, BP152-1), with 5% nonfat dry milk (Apex, 20-241)) for 1 hour or overnight at 4° C. Blots were then incubated with primary antibody at 1:500 in TBST (TBS with Tween 20 (Acros, 23336-2500) and 5% BSA (Fisher, BP1600-100) either overnight at 4° C. or room temperature for 2 hours.

Machine Learning Classifier

In some embodiments, the data set used for training the model was calcium signaling kinetics from hiPSC derived interneuron cultures as previously described (REF). In some embodiments, the model was trained with features extracted from the calcium imaging of nine iPSC cell lines. In some embodiments, features included calcium event frequency, basal calcium level, and peak calcium transience. In some embodiments, a one vs all classifier was used as does not assume independence between feature variables. In some embodiments, a gradient boosting classifier was added to prevent over fitting and not to over bias the classifier. In some embodiments, for training and predicting, down sampling was used to optimize accuracy. In some embodiments, performance was assessed pulling together classification of whole data set using a receiver-operating characteristics (ROC) curve. In some embodiments, the model was trained using 80% of the data set and the remaining 20% was portioned for testing prediction accuracy.

Bioinformatics

In some embodiments, analysis was performed to unbiasedly identify which cellular pathways in neurites are most impacted by CRMP2 activity. In some embodiments, the 2D-DIGE results were uploaded and an analysis was performed. In some embodiments, the analysis reference set utilized was a knowledge base (genes only), relationships included were direct and indirect, endogenous chemicals were included, and all molecules and/or relationships were considered. In some embodiments, a canonical pathways map was created via the analysis. In some embodiments, the canonical pathway map was manually gated to the top 22 pathways, which were determined by the most significant p-values calculated in the analysis.

Figure 11:
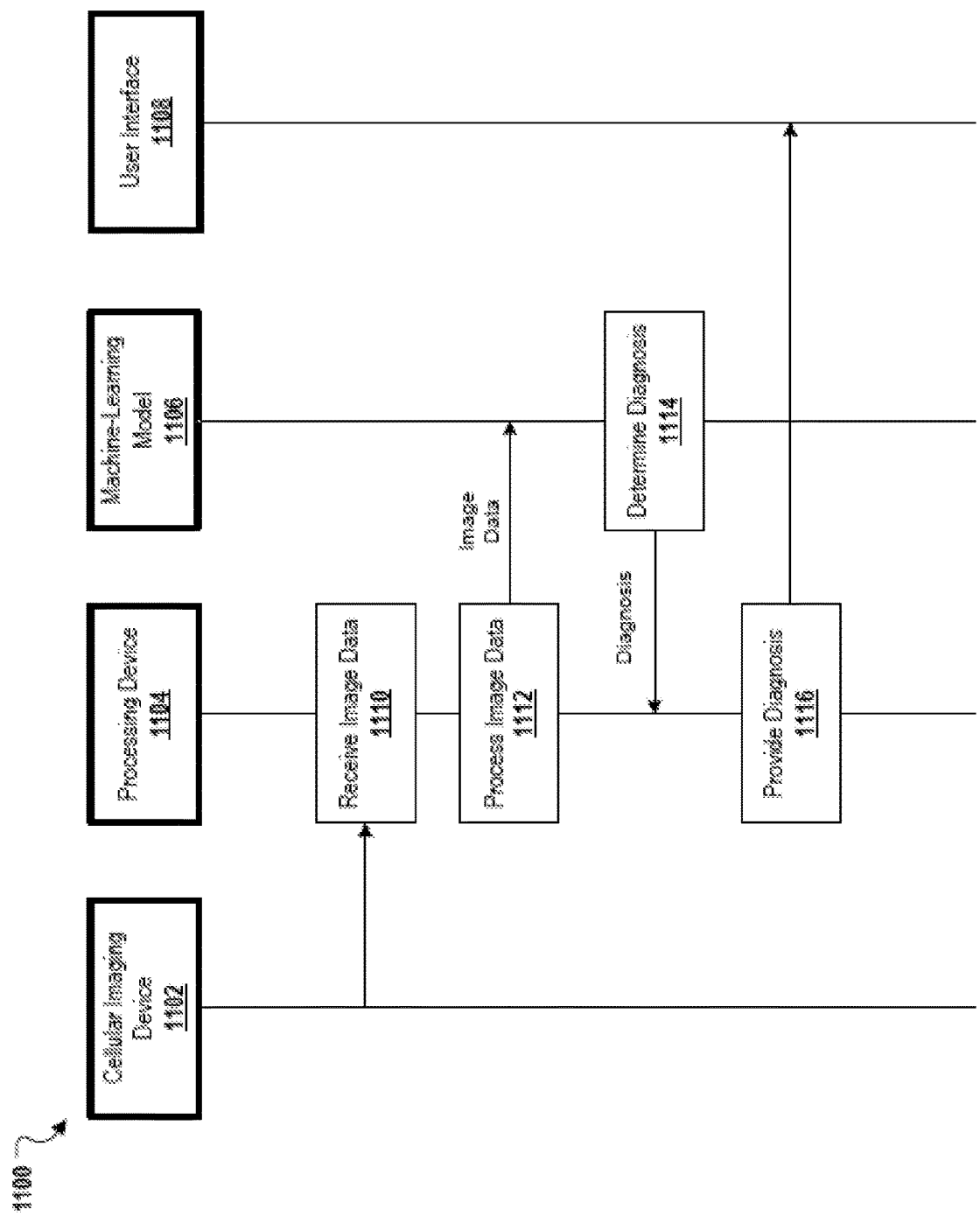
FIG. 11 depicts a flowchart of a non-limiting example process that can be implementation by embodiments of the present disclosure.

FIG. 11 depicts a flowchart of an example process 1100. The example process 1100 can be implemented by the various elements of the described classification system. As depicted, the example process shows in more detail that communication as well as the separation of work between a cellular imaging device 1102, a processing device 1104, a machine-learning model 1106, and a user interface 1108. The flowchart generally shows how imaged data is processed to determine a diagnosis for BPD. For clarity of presentation, the description that follows generally describes the example process 1100 in the context of FIGS. 1-10, and 12-13B. However, it will be understood that the process 1100 may be performed, for example, by any other suitable system, environment, software, and hardware, or a combination of systems, environments, software, and hardware as appropriate. In some embodiments, various operations of the process 1100 can be run in parallel, in combination, in loops, or in any order.

At 1110, processing device 1104 receives image data from the cellular imaging device 1102. In some embodiments, the image data includes calcium kinetic features of neuronal cultures derived from a patient. In some embodiments, the cellular imaging device 1102 is an IC200 Kinetic Image Cytometer. In some embodiments, the image data is generated through calcium imaging performed with the IC200 Kinetic Image Cytometer and a calcium sensitive dye Fluo-4 AM. In some embodiments, the image data includes intracellular calcium level traces. In some embodiments, the neuronal calcium data is acquired from in vitro neural cultures. In some embodiments, the in vitro neural cultures are derived from hiPSC isolated from BPD individuals and unaffected healthy human controls. In some embodiments, the neuronal calcium data includes calcium kinetic features. In some embodiments, the calcium kinetic features include basal calcium level, peak calcium transience, and calcium event frequency. In some embodiments, the calcium kinetic features include at least one of calcium event influx, calcium event efflux, or calcium event amplitude. In some embodiments, the neuronal cultures are derived from blood samples from the patient.

At 1112, the processing device 1104 processes the image data through a machine-learning model 1106. In some embodiments, the image data is processed through the machine-learning model 1106 to determine if the patient will respond to a treatment for BPD. In some embodiments, the image data is processed through the machine-learning model to determine a drug responsiveness of patient. In some embodiments, the machine-learning model 1106 comprises at least one of a linear regression, a naive bayes, a random forest, a one versus all, support vector classifier module, or a KNN algorithm. In some embodiments, the machine-learning model 1106 comprises a gradient boosting classifier to prevent over fitting and not to over bias the machine-learning model 1106. In some embodiments, down sampling is employed during training of the machine-learning model 1106.

At 1114, the machine-learning model 1106 determines a diagnosis for the patient based on the calcium kinetic features. In some embodiments, the machine-learning model 1106 is trained using neuronal calcium data. In some embodiments, the neuronal calcium data includes data points, and training the machine-learning model 1106 includes separating the data points by cell line and disease type. In some embodiments, a portion of the neuronal calcium data is employed to train the machine-learning model 1106 and a remaining portion of the neuronal calcium data is employed to test the machine-learning model once trained 1106. In some embodiments, testing the trained machine-learning 1106 comprises pulling LiCl treated and untreated data points from the remaining portion of the neuronal calcium data. In some embodiments, the portion of the neuronal calcium data includes 70 percent of the data for training, and the remaining portion of the neuronal calcium data includes 30 percent of the data for validation. In some embodiments, the portion of the neuronal calcium data includes 80 percent of the data for training, and the remaining portion of the neuronal calcium data includes 20 percent of the data for validation. In some embodiments, the neuronal cultures comprise CRMP2-KO, CRMP2-KI, and WT E16.5 primary hippocampal neurons.

At 1116, the processing device provides the diagnosis is to the user interface 1108. In some embodiments, the treatment comprises Lithium carbonate for BPD. In some embodiments, the diagnosis includes whether the patient is lithium responsive or lithium non-responsive.

In some embodiments, the described classification systems can successfully diagnose if an individual has bipolar disorder (BPD), and can determine if the individual will respond clinically to a bipolar disorder (BPD) treatment. In some embodiments, the BPD treatment is selected from the group consisting of mood stabilizers, antipsychotics, antidepressants, antidepressant-antipsychotics, anti-anxiety medications, and combinations thereof. In some embodiments, the described classification systems can successfully diagnose if an individual has bipolar disorder (BPD), and can determine if the individual will respond clinically to a mood stabilizer. In some embodiments, the mood stabilizer is selected from the group consisting of lithium (e.g., Lithobid), valproic acid (e.g., Depakene), divalproex sodium (e.g., Depakote), carbamazepine (e.g., Tegretol, Equetro, and Carbatrol), lamotrigine (e.g., Lamictal), topiramate (Topamax), and combinations thereof. In some embodiments, the described classification systems can successfully diagnose if an individual has bipolar disorder (BPD), and can determine if the individual will respond clinically to an antipsychotic medication. In some embodiments, the antipsychotic medication is selected from the group consisting of olanzapine (e.g., Zyprexa), risperidone (e.g., Risperdal), quetiapine (e.g., Seroquel), aripiprazole (e.g., Abilify), ziprasidone (e.g., Geodon), clozapine (e.g., Clozaril), lurasidone (e.g., Latuda), asenapine (e.g., Saphris), and combinations thereof. In some embodiments, the described classification systems can successfully diagnose if an individual has bipolar disorder (BPD), and can determine if the individual will respond clinically to an antidepressant medication. In some embodiments, the antidepressant medication is selected from the group consisting of citalopram (e.g., Celexa), escitalopram (e.g., Lexapro), fluoxetine (e.g., Prozac, Sarafem, Selfemra, and Prozac Weekly), fluvoxamine (e.g., Luvox), paroxetine (e.g., Paxil, Paxil CR, and Pexeva), sertraline (e.g., Zoloft), vortioxetine (e.g., Trintellix and Brintellix), vilazodone (e.g., Viibryd). In some embodiments, the described classification systems can successfully diagnose if an individual has bipolar disorder (BPD), and can determine if the individual will respond clinically to an antidepressant-antipsychotic medication. In some embodiments, the antidepressant-antipsychotic medication is selected from the group consisting of olanzapine/fluoxetine (e.g., Symbyax), amitriptyline/perphenazine (e.g., Duo-Vil, Etrafon, Triavil, or Triptafen), aripiprazole/sertraline (e.g., ASC-01), flupentixol/melitracen (e.g., Deanxit, Placida, Franxit, Anxidreg, and Danxipress), tranylcypromine/trifluoperazine (e.g., Parstelin, Parmodalin, Jatrosom N, and Stelapar), and combinations thereof. In some embodiments, the described classification systems can successfully diagnose if an individual has bipolar disorder (BPD), and can determine if the individual will respond clinically to an anti-anxiety medication. In some embodiments, the anti-anxiety medication is selected from the group consisting of benzodiazepines (e.g., alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof), beta-blockers (e.g., Acebutolol (Sectral), Atenolol (Tenormin), Betaxolol (Kerlone), Bisoprolol (Zebeta, Ziac), Carteolol (Cartrol), Carvedilol (Coreg), Labetalol (Normodyne, Trandate), Metoprolol (Lopressor, Toprol-XL), Nadolol (Corgard), Nebivolol (Bystolic), Penbutolol (Levatol), Pindolol (Visken), Propanolol (Inderal), Sotalol (Betapace), and Timolol (Blocadren)), buspirone (e.g., BuSpar), selective serotonin reuptake inhibitors (SSRIs) (e.g., Paxil (paroxetine), Prozac (fluoxetine), Zoloft (sertraline) and Lexapro (escitalopram)), serotonin-norepinephrine reuptake inhibitors (SNRIs) (e.g., Effexor (venlafaxine), Cymbalta (duloxetine), and Pristiq (desvenlafaxine)), and tricyclic antidepressants (e.g., Tofranil (imipramine), Elavil (amitriptyline), Pamelor (nortriptyline) and Anafranil (clomipramine)). In some embodiments, the BPD treatment further comprises calcium channel blockers (e.g., verapamil, nimodipine, diltiazem, and isradipine).

In some embodiments, the described classification systems can successfully diagnose if an individual has Alzheimer's disease (AD), and can determine if the individual will respond clinically to an Alzheimer's disease (AD) treatment. In some embodiments, the Alzheimer's disease (AD) treatment is selected from the group consisting of cholinesterase inhibitors (e.g., donepezil (Aricept), rivastigmine (Exelon), and galantamine (Razadyne)), memantine (e.g., Namenda), and combinations thereof.

In some embodiments, the described classification systems can successfully diagnose if an individual has Parkinson's disease (PD), and can determine if the individual will respond clinically to a Parkinson's disease (PD) treatment. In some embodiments, the PD treatment is selected from the group consisting of carbidopa-levodopa (e.g., Lodosyn), carbidopa-levodopa infusion (e.g., Duopa), dopamine agonists (e.g, pramipexole (Mirapex), ropinirole (Requip), rotigotine (Neupro), and apomorphine (Apokyn)), MAO B inhibitors (e.g., selegiline (Eldepryl and Zelapar), rasagiline (Azilect) and safinamide (Xadago)), catechol O-methyltransferase (COMT) inhibitors (e.g., entacapone (Comtan) and tolcapone (Tasmar)), anticholinergics (e.g., benztropine (Cogentin) and trihexyphenidyl), amantadine, and combinations thereof.

Processing Devices and Processors

In some embodiments, the platforms, systems, media, and methods described herein include a computer, or use of the same. In further embodiments, the computer includes one or more hardware central processing units (CPUs) or general purpose graphics processing units (GPGPUs) that carry out the device's functions. In still further embodiments, the computer comprises an operating system configured to perform executable instructions. In some embodiments, the computer is optionally connected a computer network. In further embodiments, the computer is optionally connected to the Internet such that it accesses the World Wide Web. In still further embodiments, the computer is optionally connected to a cloud computing infrastructure. In other embodiments, the computer is optionally connected to an intranet. In other embodiments, the computer is optionally connected to a data storage device.

In accordance with the description herein, suitable computers include, by way of non-limiting examples, server computers, desktop computers, laptop computers, notebook computers, sub-notebook computers, netbook computers, netpad computers, handheld computers, Internet appliances, mobile smartphones, tablet computers, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the computer includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the computer is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, compact disc (CD)-Read only Memories (ROMs), Digital Versatile Disks (DVDs), flash memory devices, magnetic disk drives, magnetic tapes drives, optical disk drives, and cloud computing based storage. In further embodiments, the storage and/or memory device is a combination of devices such as those disclosed herein.

In some embodiments, the computer includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the computer, such as a virtual reality (VR) or mixed reality (MR) headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the computer includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 12:
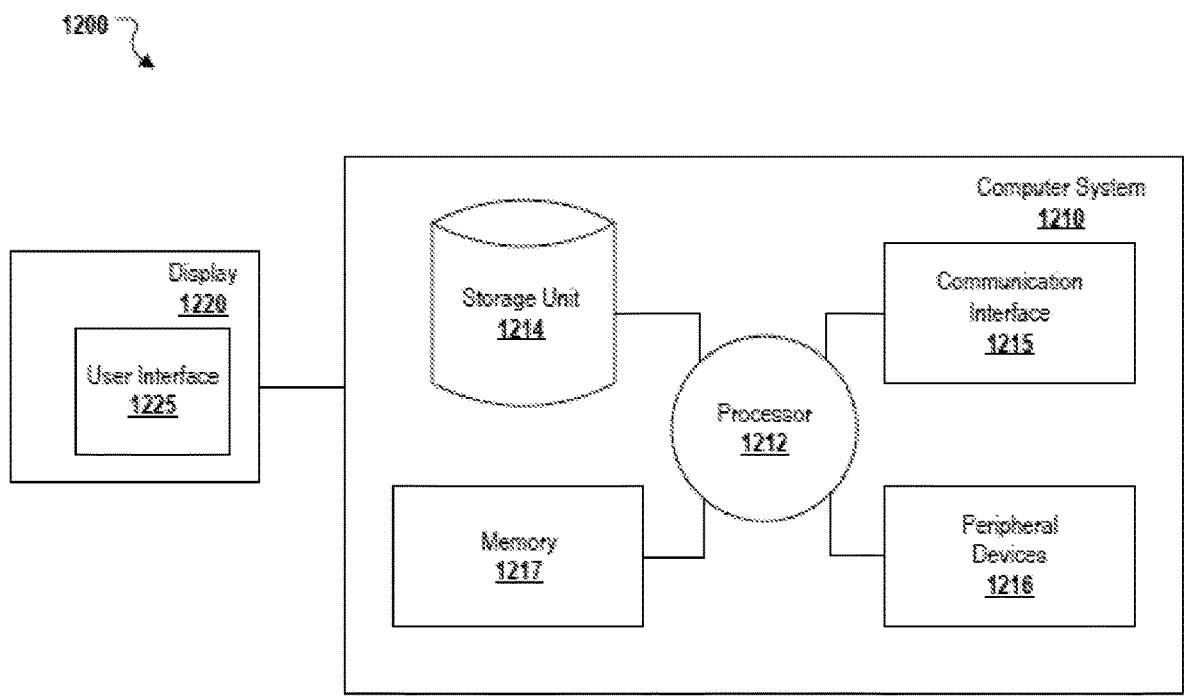
FIG. 12 depicts a non-limiting example a computer system that can be programmed or otherwise configured to implement methods or systems of the present disclosure.

Computer systems are provided herein that can be used to implement methods or systems of the disclosure. FIG. 12 depicts an example a computer system 1210 that can be programmed or otherwise configured to implement methods or systems of the present disclosure. For example, the computing device 1210 can be programmed or otherwise configured to provide a diagnosis based on received image data.

In the depicted embodiment, the computing device 1210 includes a CPU (also "processor" and "computer processor" herein) 1212, which is optionally a single core, a multi core processor, or a plurality of processors for parallel processing. The computing device 1210 also includes memory or memory location 1217 (e.g., random-access memory, read-only memory, flash memory), electronic storage unit 1214 (e.g., hard disk), communication interface 1215 (e.g., network adapter) for communicating with one or more other systems, and peripheral devices 1216, such as cache, other memory, data storage and/or electronic display adapters. The memory 1217, storage unit 1214, interface 1215 and peripheral devices 1216 are in communication with the CPU 1212 through a communication bus (solid lines), such as a motherboard. The storage unit 1214 comprises a data storage unit (or data repository) for storing data. The computing device 1210 is optionally operatively coupled to a computer network, such as the network 1210 depicted and described in FIG. 12A, with the aid of the communication interface 1215. In some embodiments, the computing device 1210 is configured as a node within a peer-to-peer network.

In some embodiments, the CPU 1212 can execute a sequence of machine-readable instructions, which can be embodied in a program or software. The instructions may be stored in a memory location, such as the memory 1217. The instructions can be directed to the CPU 1212, which can subsequently program or otherwise configure the CPU 1212 to implement methods of the present disclosure. Examples of operations performed by the CPU 1212 can include fetch, decode, execute, and write back. In some embodiments, the CPU 1212 is part of a circuit, such as an integrated circuit. One or more other components of the computing device 1210 can be optionally included in the circuit. In some embodiments, the circuit is an application specific integrated circuit (ASIC) or a FPGA.

In some embodiments, the storage unit 1214 stores files, such as drivers, libraries, images, and saved programs. In some embodiments, the storage unit 1214 stores user data, e.g., user preferences and user programs. In some embodiments, the computing device 1210 includes one or more additional data storage units that are external, such as located on a remote server that is in communication through an intranet or the internet.

In some embodiments, the computing device 1210 communicates with one or more remote computer systems through a network. For instance, the computing device 1210 can communicate with a remote computer system. Examples of remote computer systems include personal computers (e.g., portable PC), slate or tablet PCs (e.g., Apple® iPad, Samsung® Galaxy Tab, etc.), smartphones (e.g., Apple® iPhone, Android-enabled device, Blackberry®, etc.), or personal digital assistants. In some embodiments, a user can access the computing device 1210 via a network.

In some embodiments, methods as described herein are implemented by way of machine (e.g., computer processor) executable code stored on an electronic storage location of the computing device 1210, such as, for example, on the memory 1217 or the electronic storage unit 1214. In some embodiments, the CPU 1212 is adapted to execute the code. In some embodiments, the machine executable or machine readable code is provided in the form of software. In some embodiments, during use, the code is executed by the CPU 1212. In some embodiments, the code is retrieved from the storage unit 1214 and stored on the memory 1217 for ready access by the CPU 1212. In some situations, the electronic storage unit 1214 is precluded, and machine-executable instructions are stored on the memory 1217. In some embodiments, the code is pre-compiled. In some embodiments, the code is compiled during runtime. The code can be supplied in a programming language that can be selected to enable the code to execute in a pre-compiled or as-compiled fashion.

In some embodiments, the computing device 1210 can include or be in communication with an electronic display 1220. In some embodiments, the electronic display 1220 provides a user interface (UI) 1225.

Figure 13A:
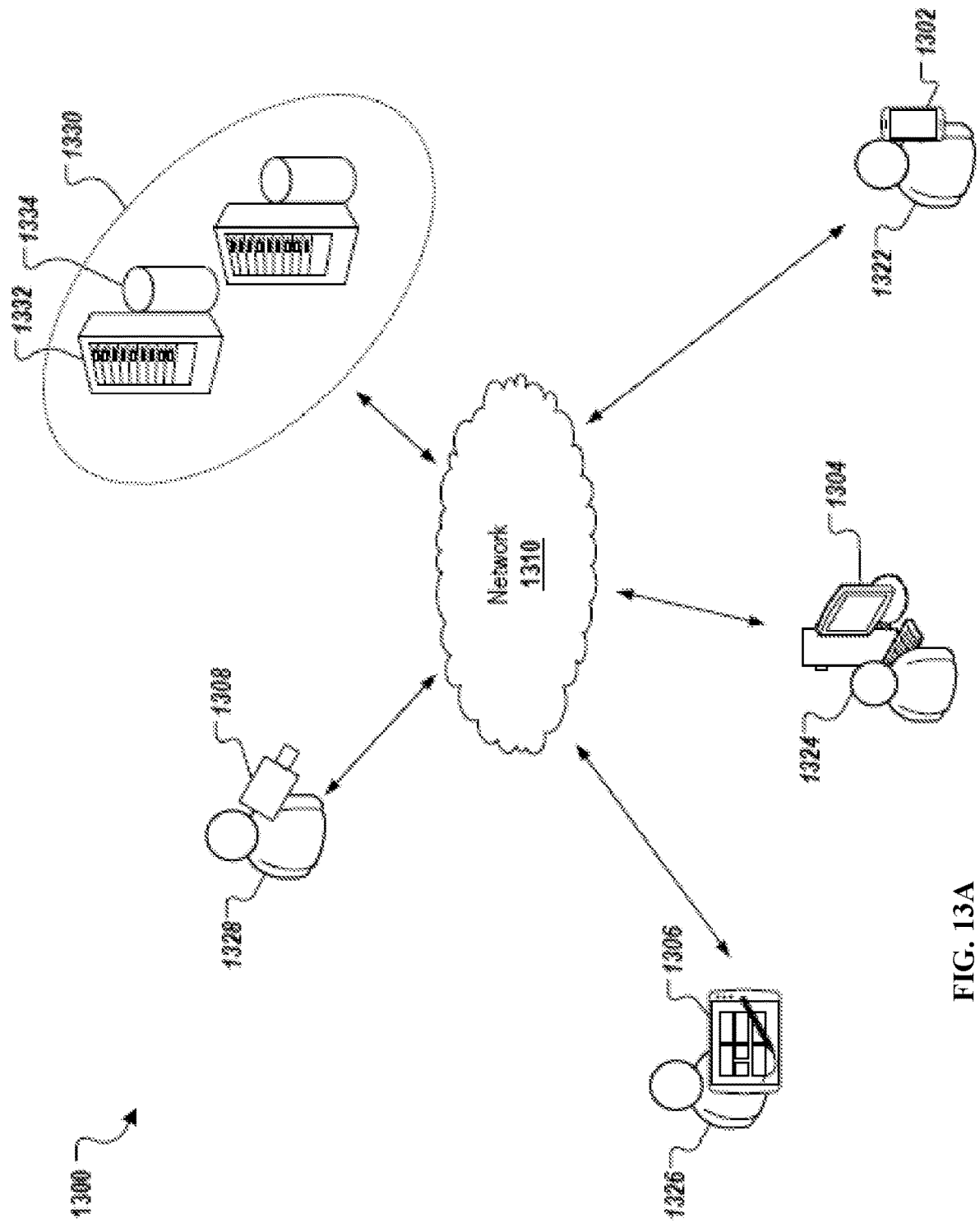
FIG. 13A depicts a non-limiting example environment that can be employed to execute implementations of the present disclosure.

FIG. 13A depicts an example environment 1300 that can be employed to execute implementations of the present disclosure. The example system 1300 includes computing devices 1302, 1304, 1306, an imaging device 1308, a back-end system 1330, and a network 1310. In some embodiments, the network 1310 includes a local area network (LAN), wide area network (WAN), the Internet, or a combination thereof, and connects web sites, devices (e.g., the computing devices 1302, 1304, and 1306, and the imaging device 1308) and back-end systems (e.g., the back-end system 1330). In some embodiments, the network 1310 includes the Internet, an internet, and/or extranet, or an intranet and/or extranet that is in communication with the Internet. In some embodiments, the network 1310 includes a telecommunication and/or data network. In some embodiments, the network 1310 can be accessed over a wired and/or a wireless communications link. For example, mobile computing devices (e.g., the smartphone device 1302 and the tablet device 1306), can use a cellular network to access the network 1310.

In some embodiments, the example environment 1300 is within a cellular imaging laboratory. The described classification system may be employed within the example environment 1300 to, for example, employ machine learning/AI techniques to determine a diagnosis for a patient based on image data collected by the imaging device 1308.

In some examples, the user 1228 interacts with the cellular imaging device 1328. In some embodiments, the cellular imaging device 1328 can be employed to capture a diverse range of samples, such as, image live cells, stem cells, plants, tissue slices, whole organisms, and complex 3D matrices. In some embodiments, the cellular imaging device 1328 is an IC200 Kinetic Image Cytometer.

In some examples, the users 1322, 1324, and 1326 interact with the described classification system through a GUI or application that is installed and executing on their respective computing devices 1302, 1304, and 1306. In some examples, the computing devices 1302, 1304, and 1306 provide viewing data to screens within a cellular imaging laboratory with which the users 1322, 1324, and 1326, can interact. In some embodiments, the computing devices 1302, 1304, 1306 are sustainably similar to computing device 1210 depicted in FIG. 12. The computing devices 1302, 1304, 1306 may each include any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices. In the depicted example, the computing device 1302 is a smartphone, the computing device 1304 is a tablet-computing device, and the computing device 1206 is a desktop computing device. Three user computing devices 1302, 1304, and 1306, are depicted in FIG. 13A for simplicity. It is contemplated, however, that implementations of the present disclosure can be realized with any of the appropriate computing devices, such as those mentioned previously. Moreover, implementations of the present disclosure can employ any number of devices as required.

In the depicted example environment 1300, the back-end system 1330 includes at least one server device 1332 and at least one data store 1334. In some embodiments, the device 1332 is sustainably similar to computing device 1210 depicted in FIG. 12. In some embodiments, back-end system 1330 may include server-class hardware type devices. In some embodiments, the server device 1332 is a server-class hardware type device. In some embodiments, back-end system 1330 includes computer systems using clustered computers and components to act as a single pool of seamless resources when accessed through the network 1310. For example, such implementations may be used in data center, cloud computing, storage area network (SAN), and network attached storage (NAS) applications. In some embodiments, back-end system 1330 is deployed using a virtual machine(s). In some embodiments, the data store 1334 is a repository for persistently storing and managing collections of data. Example data store that may be employed within the described classification system include data repositories, such as a database as well as simpler store types, such as files, emails, and so forth. In some embodiments, the data store 1334 includes a database. In some embodiments, a database is a series of bytes or an organized collection of data that is managed by a database management system (DBMS).

In some embodiments, the at least one server system 1332 hosts one or more computer-implemented services, such as described above, provided by the described classification system that users 1322, 1324, 1326, and 1328 can interact with using the respective computing devices 1302, 1304, and 1306 and the imaging device 1328.

Figure 13B:
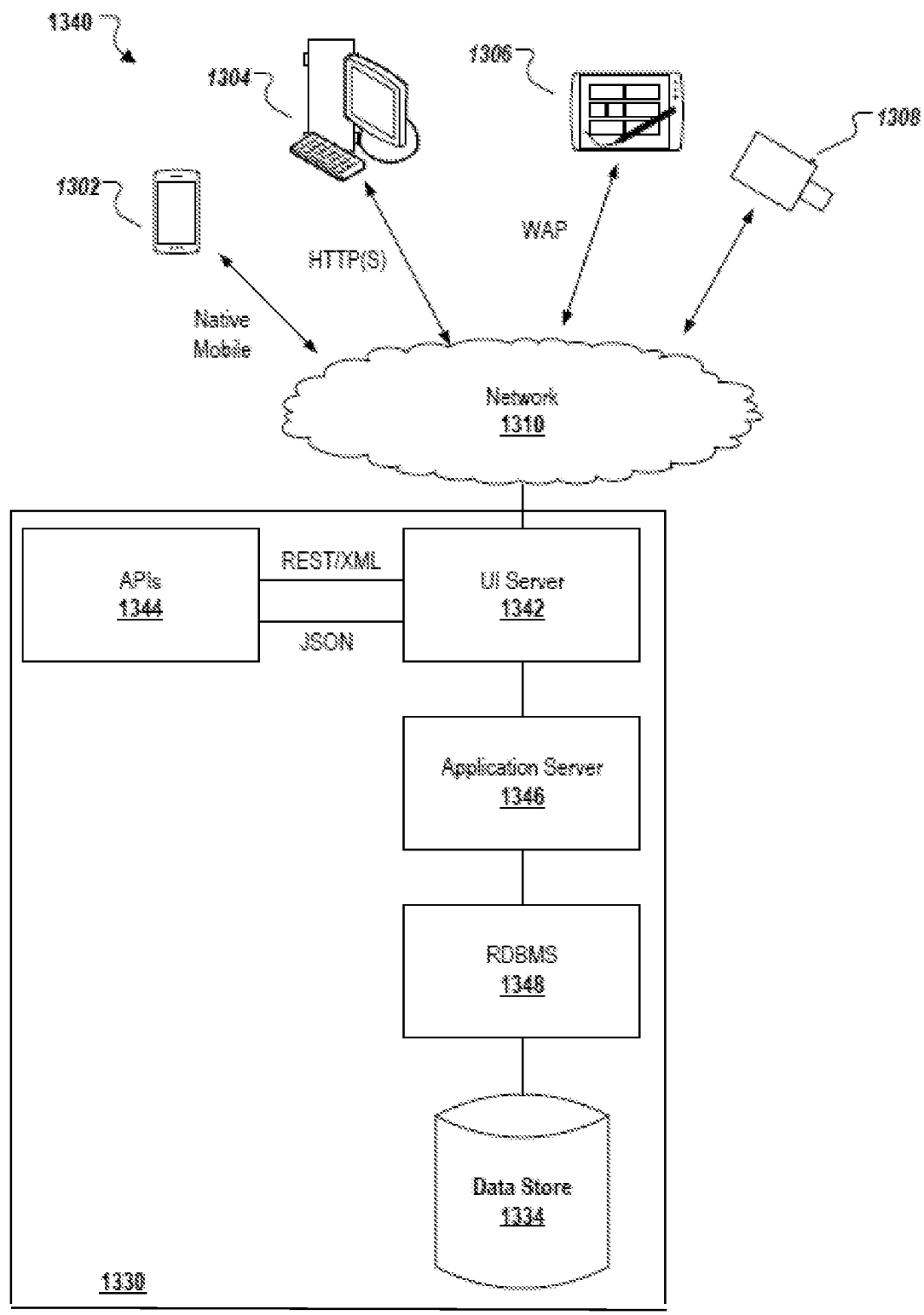
FIG. 13B depicts a non-limiting example application provision system that can be provided through an environment and employed to execute implementations of the present disclosure.

FIG. 13B depicts an example classification system 1340 that can be provided through an environment, such as the example environment 1300 and employed to execute implementations of the present disclosure. As depicted, the example classification system 1340 includes the back-end system 1330 configured to include one or more data stores 1334 accessed by a relational database management system (RDBMS) 1348. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. As depicted, the example application provision system 1340 includes the back-end system 1330 configured to include one or more application severs 1346 (such as Java servers, .NET servers, PHP servers, and the like) and one or more UI servers 1342 (e.g., a web server, such as Apache, IIS, GWS and the like). The UI server(s) 1342 optionally expose one or more web services via an API 1344 via the network 1310. In some embodiments, the example application provision system 1340 provides browser-based or mobile native user interfaces to the computing devices 1302, 1304, 1306, 1308. In some embodiments, the computing devices 1302, 1304, 1306, 1308 may connect to the back-end system 1330 via a cable, such as a Universal Serial Bus (USB) cable. For example, the cellular imaging device 1328 may provide captured images to the back-end system 1330 via the USB cable, and the diagnosis may be provided to the computing devices 1302, 1304, 1306 through the UI server 1342.

Non-transitory Computer Readable Storage Medium

In some embodiments, the platforms, systems, media, and methods disclosed herein include one or more non-transitory computer readable storage media encoded with a program including instructions executable by the operating system of an optionally networked computer. In further embodiments, a computer readable storage medium is a tangible component of a computer. In still further embodiments, a computer readable storage medium is optionally removable from a computer. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. In some embodiments, a computer program includes a sequence of instructions, executable in the computer's CPU, written to perform a specified task. Computer readable instructions may be implemented as program modules, such as functions, objects, API, data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Machine Learning

In some embodiments, machine learning algorithms are employed to determine a diagnosis for the patient. For example, a machine-learning model trained using neuronal calcium data to determine a diagnosis based on the calcium kinetic features of collected image data. Examples of machine learning algorithms may include a support vector machine (SVM), a naïve Bayes classification, a random forest, a neural network, deep learning, or other supervised learning algorithm or unsupervised learning algorithm for classification and regression. The machine learning algorithms may be trained using one or more training datasets (e.g., using neuronal calcium data). For example, neuronal calcium data may be employed to train various algorithms. Moreover, as described above, these algorithms can be continuous trained/retrained using BPD diagnosis determined by the described classification system. In some embodiments, the machine learning algorithm employs regression modelling where relationships between variables are determined and weighted.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile computer. In some embodiments, the mobile application is provided to a mobile computer at the time it is manufactured. In other embodiments, the mobile application is provided to a mobile computer via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and Visual Basic (VB) .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for receiving weather, maritime, environmental, civil, governmental or military data. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A classification system, comprising:
a user interface;
a cellular imaging device;
one or more processors; and
a non-transitory computer-readable storage device coupled to the one or more processors and having instructions stored thereon which, when executed by the one or more processors, cause the one or more processors to perform operations comprising:
receiving, from the cellular imaging device, image data comprising calcium kinetic features of neuronal cultures derived from a patient;
processing the image data through a machine-learning model to determine a diagnosis for the patient based on the calcium kinetic features, wherein the machine-learning model is trained using neuronal calcium data; and
wherein the neuronal calcium data comprises (i) basal calcium level, peak calcium transience, calcium event frequency, and calcium event amplitude, and (ii) at least one of calcium event influx and calcium event efflux; and providing the diagnosis to the user interface, wherein the diagnosis is for bipolar disorder (BPD), Alzheimer's disease or Parkinson's disease.

2. The classification system of claim 1, wherein the operations comprise:
processing the image data through the machine-learning model to determine if the patient will respond to a treatment.

3. The classification system of claim 2, wherein the treatment comprises lithium carbonate for bipolar disorder (BPD).

4. The classification system of claim 1, wherein the diagnosis comprises whether the patient is lithium responsive or lithium non-responsive.

5. The classification system of claim 1, wherein the neuronal calcium data is acquired from in vitro neural cultures.

6. A computer-implemented method for patient screening, the method being executed by one or more processors and comprising:
receiving, from a cellular imaging device, image data comprising calcium kinetic features of neuronal cultures derived from a patient;
processing the image data through a machine-learning model to determine a diagnosis for the patient based on the calcium kinetic features, wherein the machine-learning model is trained using neuronal calcium data and wherein the neuronal calcium data comprises (i) basal calcium level, peak calcium transience, calcium event frequency, and calcium event amplitude, and (ii) at least one of calcium event influx and calcium event efflux; and
providing the diagnosis to a user interface, wherein the diagnosis is for bipolar disorder (BPD), Alzheimer's disease or Parkinson's disease.

7. The method of claim 6, comprising:
processing the image data through the machine-learning model to determine if the patient will respond to a treatment.

8. The method of claim 6, comprising:
processing the image data through the machine-learning model to determine a drug responsiveness of the patient.

9. The method of claim 6, wherein the diagnosis comprises whether the patient is lithium responsive or lithium non-responsive.

10. The method of claim 6, wherein the machine-learning model comprises a gradient boosting classifier to prevent over fitting and not to over bias the machine-learning model.

11. The method of claim 6, wherein the neuronal calcium data is acquired from in vitro neural cultures.

12. The method of claim 6, wherein a portion of the neuronal calcium data is employed to train the machine-learning model and a remaining portion of the neuronal calcium data is employed to test the machine-learning model once trained, and wherein i) the portion of the neuronal calcium data comprises 70 percent of the data for training, and wherein the remaining portion of the neuronal calcium data comprises 30 percent of the data for validation, or ii) the portion of the neuronal calcium data comprises 80 percent of the data for training, and wherein the remaining portion of the neuronal calcium data comprises 20 percent of the data for validation.

13. The method of claim 6, wherein the image data comprises intracellular calcium level traces.

14. The method of claim 6, wherein the neuronal cultures comprise Collapsin Response Mediator Protein-2 (CRMP2)-knock out (KO), CRMP2-knock in (KI), and WT E16.5 primary hippocampal neurons.

15. The method of claim 6, wherein the neuronal cultures are derived from blood samples from the patient.

* * * * *